US011889811B2

(12) United States Patent
de Godoy Lusso et al.

(10) Patent No.: US 11,889,811 B2
(45) Date of Patent: *Feb. 6, 2024

(54) DARK TOBACCO INBREDS AND HYBRIDS COMPRISING REDUCED NICOTINE DEMETHYLATION AND NORNICOTINE

(71) Applicant: Altria Client Services LLC, Richmond, VA (US)

(72) Inventors: Marcos Fernando de Godoy Lusso, Chesterfield, VA (US); Andrew Carl Adams, Midlothian, VA (US)

(73) Assignee: Altria Client Services LLC, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/528,926

(22) Filed: Nov. 17, 2021

(65) Prior Publication Data

US 2022/0061259 A1 Mar. 3, 2022

Related U.S. Application Data

(63) Continuation of application No. 16/774,831, filed on Jan. 28, 2020, now Pat. No. 11,206,778, which is a continuation of application No. 15/808,202, filed on Nov. 9, 2017, now Pat. No. 10,582,680.

(60) Provisional application No. 62/558,072, filed on Sep. 13, 2017, provisional application No. 62/441,855, filed on Jan. 3, 2017, provisional application No. 62/420,527, filed on Nov. 10, 2016.

(51) Int. Cl.
| | |
|---|---|
| *A01H 6/82* | (2018.01) |
| *A24B 15/20* | (2006.01) |
| *A01H 5/00* | (2018.01) |
| *A01H 5/12* | (2018.01) |
| *A24B 13/00* | (2006.01) |
| *A24B 15/10* | (2006.01) |

(52) U.S. Cl.
CPC .............. *A01H 6/823* (2018.05); *A01H 5/00* (2013.01); *A01H 5/12* (2013.01); *A24B 13/00* (2013.01); *A24B 15/10* (2013.01); *A24B 15/20* (2013.01)

(58) Field of Classification Search
CPC .................................. A01H 6/823; A01H 5/00
See application file for complete search history.

(56) References Cited

U.S. PATENT DOCUMENTS

| | | | |
|---|---|---|---|
| 10,582,680 B2 * | 3/2020 | de Godoy Lusso | A01H 6/823 |
| 2008/0245377 A1 | 10/2008 | Marshall et al. | |
| 2014/0251353 A1 | 9/2014 | Lewis et al. | |
| 2015/0245584 A1 | 9/2015 | Lewis et al. | |

OTHER PUBLICATIONS

Bailey et al., "Evaluation of Dark Fire-Cured SRC (Stable Reduced Converter) Lines with Zyvert TM Technology in Kentucky and Tennessee Field Trails," Jan. 16, 2018 XP55459194, www.coresta.org/sites/default/files/abstracts/2018_TWC15_Bailey.pdf.
Bush et al., "Formation of Tobacco-Specific Nitrosamines in Air-Cured Tobacco," *Rec. Adv. Tob. Sci.* 27:23-46 (2001).
Boyette et al., "Recent Advances in Tobacco Science," *Rec. Adv. Tob. Sci.* 27:17-22 (2001).
Gavilano et al., "Genetic Engineering of Nicotiana tobacum for Reduced Nornicotine Content," *Journal of Agricultural and Food Chemistry, American Chemical Society, Books and Journals Division*, 54(24):9071-9078 (2006).
Hall et al., "Supping with the Devil? The role of law in promoting tobacco harm reduction using low nitrosamine smokeless tobacco products," *Public Health* Jan. 1, 2017 (Jan. 1, 2017), pp. 287-291, XP55459185, Netherlands DOI: 10.1016/j.puhe.2008.12.018 retrieved from the Internet: URL: https://www.coresta.org/sites/default/files/abstract/20172017.
Hecht et al., "The Relevance of Tobacco-specific Nitrosamines to Human Cancer," *Cancer Surveys*, 8:273-294 (1989).
Hoffman et al., "Tobacco-Specific N-Nitrosamines and Arecaderived N-Nitrosames: Chemistry, Biochemistry, Carcinogenicity, and Relevance to Humans," *Journal of Toxicology and Environmental Health*, 41:1-52 (1994).
International Search Report and Written Opinion dated Apr. 9, 2018 in corresponding International Application PCT/US2017/060814.
Julio et al., "Reducing the Content of Nornicotine in Tobacco via Targeted Mutation Breeding," *Mol. Breeding*, 21:369-381 (2008).
Lewis et al., Three Nicotine Demethylase Genes Mediate Nornicotine Biosynthesis in *Nicotiana tabacum* L.: Functional Characterization of the *Cyp82E10* Gene, *Phytochemistry*, 71:1988-1998 (2010).
Lusso et al., "N-nitrosonornicotine Reduction in Dark Tobacco Varieties and Smokeless Product Prototypes," *Research, Development & Reg Affairs*, 601 East Jackson Street, Sep. 18, 2017.
Morton et al., "Variability of NNN in Tobacco and NNN Levels in Smokeless Tobacco Products," *Journal of Agricultural and Food Chemistry*, p. 4400 (2017) XP55459212 www.coresta.org/sites/default/files/abstract/2017_IG01_lusso.pdf.
Peels et al., "Formation of Tobacco Specific Nitrosamines in Flue-Cured Tobacco," *Coresta Agronomy and Phytopathology Meeting*, pp. 4628-4651 (1999) http://legacy.library.ucsf.edu/tid/jug33a00/pdf.
University of Kentucky Cooperative Extension Service; Agriculture and Natural Resources Publication 2013-2014 Kentucky and Tennessee Tobacco Production Guide, pp. 1-71 (2013).

(Continued)

*Primary Examiner* — Russell Kallis
(74) *Attorney, Agent, or Firm* — Arnold & Porter Kaye Scholer LLP

(57) ABSTRACT

The present disclosure provides tobacco inbred plants TND950 (phph) SRC, Narrow Leaf Madole (phph) SRC, Narrow Leaf Madole SRC, CMS TND950 SRC, CMS Narrow Leaf Madole SRC, and CMS KY171 SRC, and hybrids PD7305 SRC, PD7309 SRC, PD7312 SRC, PD7318 SRC, and PD7319 SRC. The present disclosure also provides parts of such plants and products made from those parts. The present disclosure also includes progeny of the provided plants including hybrids.

18 Claims, 9 Drawing Sheets

Specification includes a Sequence Listing.

(56) References Cited

OTHER PUBLICATIONS

Wernsman et al., "Time and Site of Nicotine Conversation in Tobacco," *Tobacco Science*, 167(22):58-60 (1968).

Wernsman et al., "Principles of Cultivar Development: Crop Species," *MacMillan Publishing Go.*, 2(17):669-698 (1987).

Wernsman et al., "Relative Stability of Alleles at the Nicotine Conversion Locus of Tobacco," Agriculture Experiment Station, University of North Carolina, Raleigh, N.C. USA, *Tobacco Science*, 14:34-36 (1970).

Hecht "Invited Review: Biochemistry, Biology, and Carcinogenicity of Tobacco-Specific N-Nitrosamines," *Chemical Research in Toxicology*, vol. 11, No. 6, pp. 559-603 (Jun. 1998) (Washington, DC).

Jack et al., "Implications of reducing nornicotine accumulation in burley tobacco: appendix A—the LC protocol," *Rec. Adv. Tab. Sci.* vol. 33, pp. 58-79 (2007) available online: www.uky.edu/Ag/Tobacco/Pdf/LC-Protocol.pdf.

\* cited by examiner

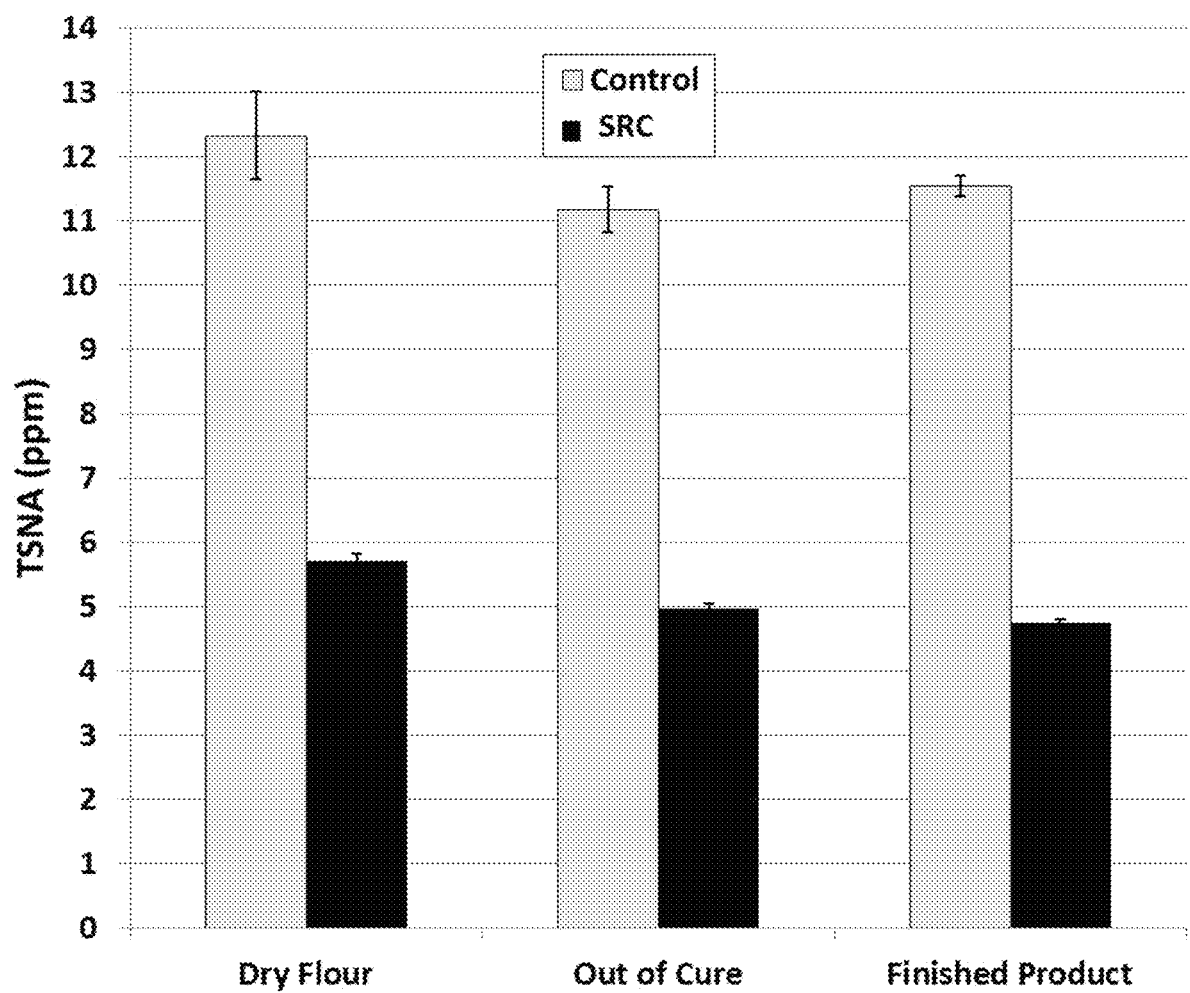

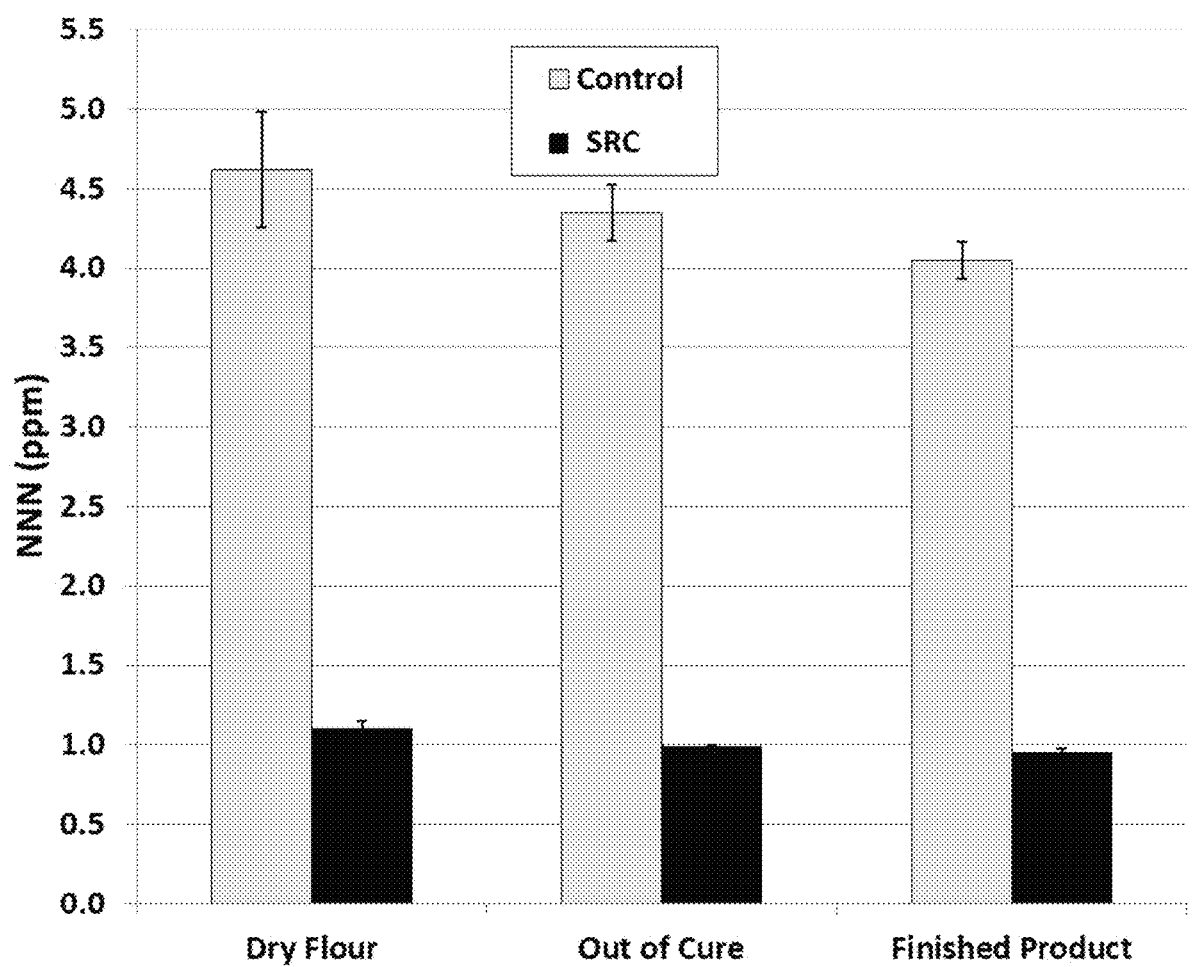

SEQUENCE LISTING

```
<160> NUMBER OF SEQ ID NOS: 12

<210> SEQ ID NO 1
<211> LENGTH: 1554
<212> TYPE: DNA
<213> ORGANISM: Nicotiana tabacum
<220> FEATURE:
<221> NAME/KEY: Mutation
<222> LOCATION: (986)..(986)
<223> OTHER INFORMATION: G to A

<400> SEQUENCE: 1
atgctttctc ccatagaagc cattgtagga ctagtaacct tcacatttct cttcttcttc      60
ctatggacaa aaaatctca aaaaccttca aaacccttac caccgaaaat ccccggagga     120
tggccggtaa tcggccatct tttccacttc aatgacgacg gcgacgaccg tccattagct     180
cgaaaactcg gagacttagc tgacaaatac ggccccgttt tcacttttcg gctaggcctt     240 cccttgtct tagttgtaag cagttacgaa gctgtaaaag actgtttctc tacaaatgac      300 gccattttt ccaatcgtcc agcttttctt tacggcgatt accttggcta caataatgcc      360
atgctatttt tggccaatta cggaccttac tggcgaaaaa atcgaaaatt agttattcag     420
gaagttctct ccgctagtcg tctcgaaaaa ttcaaacacg tgagatttgc aagaattcaa     480
gcgagcatta agaatttata tactcgaatt gatggaaatt cgagtacgat aaatttaact     540
gattggttag aagaattgaa ttttggtctg atcgtgaaga tgatcgctgg aaaaaattat     600
gaatccggta aaggagatga acaagtggag agatttaaga aagcgtttaa ggattttatg     660
```

```
attttatcaa tggagtttgt gttatgggat gcatttccaa ttccattatt taaatgggtg    720
gattttcaag ggcatgttaa ggctatgaaa aggacttttta aagatataga ttctgttttt    780
cagaattggt tagaggaaca tattaataaa agagaaaaaa tggaggttaa tgcagaaggg    840
aatgaacaag atttcattga tgtggtgctt tcaaaaatga gtaatgaata tcttggtgaa    900
ggttactctc gtgatactgt cattaaagca acggtgttta gtttggtctt ggatgcagca    960
gacacagttg ctcttcacat aaattaggga atggcattat tgataaacaa tcaaaaggcc   1020
ttgacgaaag cacaagaaga gatagacaca aaagttggta aggacagatg ggtagaagag   1080
agtgatatta aggatttggt ataccctcca gctattgtta aagaagtgtt acgattatat   1140
ccaccaggac ctttgttagt accacacgaa aatgtagaag attgtgttgt tagtggatat   1200
cacattccta aagggacaag attattcgca acgtcatga aactgcaacg tgatcctaaa    1260
ctctggtctg atcctgatac tttcgatcca gagagattca ttgctactga tattgacttt   1320
cgtggtcagt actataagta tatcccgttt ggttctggaa gacgatcttg tccagggatg   1380
acttatgcat tgcaagtgga acacttaaca atggcacatt tgatccaagg tttcaattac   1440
agaactccaa atgacgagcc cttggatatg aaggaaggtg caggcataac tatacgtaag   1500
gtaaatcctg tggaactgat aatagcgcct cgcctggcac ctgagctttta ttaa         1554

<210> SEQ ID NO 2
<211> LENGTH: 1554
<212> TYPE: DNA
<213> ORGANISM: Nicotiana tabacum
<220> FEATURE:
<221> NAME/KEY: Mutation
<222> LOCATION: (1266)..(1266)
<223> OTHER INFORMATION: G to A

<400> SEQUENCE: 2
atggtttctc ccgtagaagc cattgtagga ctagtaaccc ttacacttct cttctacttc     60
ctatggccca aaaatttca aataccttca aaccattac caccgaaaat tcccggaggg    120
tggccggtaa tcggccatct tttctacttc gatgatgacg gcgacgaccg tccattagct    180
cgaaaactcg gagacttagc tgacaaatac ggcccggttt tcactttccg gctaggcctt    240
ccgcttgtgt tagttgtaag cagttacgaa gctgtaaaag actgcttctc tacaaatgac    300
gccattttct ccaatcgtcc agcttttctt tacggtgaat accttggcta cagtaatgcc    360
atgctatttt tgacaaaata cggaccttat tggcgaaaaa atagaaaatt agtcattcag    420
gaagttctct ctgctagtcg tctcgaaaaa ttgaagcacg tgagatttgg taaaattcaa    480
acgagcatta agagtttata cactcgaatt gatggaaatt cgagtacgat aaatctaact    540
gattggttag aagaattgaa ttttggtctg atcgtgaaaa tgatcgctgg gaaaaattat    600
gaatccggta aggagatga acaagtggag agatttagga aagcgtttaa ggattttata    660
attttatcaa tggagtttgt gttatgggat gcttttccaa ttccattgtt caaatgggtg    720
gattttcaag gccatgttaa ggccatgaaa aggacattta aggatataga ttctgttttt    780
cagaattggt tagaggaaca tgtcaagaaa agagaaaaaa tggaggttaa tgcacaaggg    840
aatgaacaag atttcattga tgtggtgctt tcaaaaatga gtaatgaata tcttgatgaa    900
ggttactctc gtgatactgt cataaaagca acagtgttta gtttggtctt ggatgctgcg    960
gacacagttg ctcttcacat gaattgggga atggcattac tgataaacaa tcaacatgcc   1020
ttgaagaaag cacaagaaga gatcgataaa aaagttggta aggaaagatg ggtagaagag   1080
agtgatatta aggatttggt ctacctccaa gctattgtta aagaagtgtt acgattatat   1140
```

-continued

```
ccaccaggac ctttattagt acctcatgaa aatgtagagg attgtgttgt tagtggatat   1200
cacattccta aagggactag actattcgcg aacgttatga aattgcagcg cgatcctaaa   1260
ctctgatcaa atcctgataa gtttgatcca gagagattct tcgctgatga tattgactac   1320
cgtggtcagc actatgagtt tatcccattt ggttctggaa gacgatcttg tccggggatg   1380
acttatgcat tacaagtgga acacctaaca atagcacatt tgatccaggg tttcaattac   1440
aaaactccaa atgacgagcc cttggatatg aaggaaggtg caggattaac tatacgtaaa   1500
gtaaatcctg tagaagtgac aattacggct cgcctggcac ctgagcttta ttaa         1554
```

<210> SEQ ID NO 3
<211> LENGTH: 328
<212> TYPE: PRT
<213> ORGANISM: Nicotiana tabacum

<400> SEQUENCE: 3

```
Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
            20                  25                  30

Leu Pro Pro Lys Ile Pro Gly Gly Trp Pro Val Ile Gly His Leu Phe
        35                  40                  45

His Phe Asn Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
            100                 105                 110

Asp Tyr Leu Gly Tyr Asn Asn Ala Met Leu Phe Leu Ala Asn Tyr Gly
        115                 120                 125

Pro Tyr Trp Arg Lys Asn Arg Lys Leu Val Ile Gln Glu Val Leu Ser
    130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Lys Lys Ala Phe Lys Asp Phe Met Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Ile Asn Lys Arg Glu
            260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Gly Glu Gly Tyr Ser Arg
    290                 295                 300
```

Asp Thr Val Ile Lys Ala Thr Val Phe Ser Leu Val Leu Asp Ala Ala
305                 310                 315                 320

Asp Thr Val Ala Leu His Ile Asn
                325

<210> SEQ ID NO 4
<211> LENGTH: 421
<212> TYPE: PRT
<213> ORGANISM: Nicotiana tabacum

<400> SEQUENCE: 4

Met Val Ser Pro Val Glu Ala Ile Val Gly Leu Val Thr Leu Thr Leu
1               5                   10                  15

Leu Phe Tyr Phe Leu Trp Pro Lys Lys Phe Gln Ile Pro Ser Lys Pro
                20                  25                  30

Leu Pro Pro Lys Ile Pro Gly Gly Trp Pro Val Ile Gly His Leu Phe
            35                  40                  45

Tyr Phe Asp Asp Asp Gly Asp Asp Arg Pro Leu Ala Arg Lys Leu Gly
        50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
                100                 105                 110

Glu Tyr Leu Gly Tyr Ser Asn Ala Met Leu Phe Leu Thr Lys Tyr Gly
            115                 120                 125

Pro Tyr Trp Arg Lys Asn Arg Lys Leu Val Ile Gln Glu Val Leu Ser
        130                 135                 140

Ala Ser Arg Leu Glu Lys Leu Lys His Val Arg Phe Gly Lys Ile Gln
145                 150                 155                 160

Thr Ser Ile Lys Ser Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
                180                 185                 190

Lys Met Ile Ala Gly Lys Asn Tyr Glu Ser Gly Lys Gly Asp Glu Gln
            195                 200                 205

Val Glu Arg Phe Arg Lys Ala Phe Lys Asp Phe Ile Ile Leu Ser Met
        210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Val Lys Lys Arg Glu
                260                 265                 270

Lys Met Glu Val Asn Ala Gln Gly Asn Glu Gln Asp Phe Ile Asp Val
            275                 280                 285

Val Leu Ser Lys Met Ser Asn Glu Tyr Leu Asp Glu Gly Tyr Ser Arg
        290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Glu Ile Asp Lys Lys Val

```
            340                 345                 350
Gly Lys Glu Arg Trp Val Glu Glu Ser Asp Ile Lys Asp Leu Val Tyr
            355                 360                 365

Leu Gln Ala Ile Val Lys Glu Val Leu Arg Leu Tyr Pro Pro Gly Pro
        370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu
            420

<210> SEQ ID NO 5
<211> LENGTH: 1554
<212> TYPE: DNA
<213> ORGANISM: Nicotiana tabacum

<400> SEQUENCE: 5
atgctttctc ccatagaagc cattgtagga ctagtaacct tcacatttct cttcttcttc      60
ctatggacaa aaaatctca aaaaccttca aaacccttac caccgaaaat ccccggagga     120
tggccggtaa tcggccatct tttccacttc aatgacgacg gcgacgaccg tccattagct     180
cgaaaactcg gagacttagc tgacaaatac ggccccgttt tcacttttcg gctaggcctt     240 cccctt gtct tagttgtaag cagttacgaa gctgtaaaag actgtttctc tacaaatgac     300
gccatttttt ccaatcgtcc agcttttctt tacggcgatt accttggcta caataatgcc     360
atgctatttt tggccaatta cggaccttac tggcgaaaaa atcgaaaatt agttattcag     420
gaagttctct ccgctagtcg tctcgaaaaa ttcaaacacg tgagatttgc aagaattcaa     480
gcgagcatta agaatttata tactcgaatt gatggaaatt cgagtacgat aaatttaact     540
gattggttag aagaattgaa ttttggtctg atcgtgaaga tgatcgctgg aaaaaattat     600
gaatccggta aggagatgaa acaagtggag agatttaaga aagcgtttaa ggattttatg     660
attttatcaa tggagtttgt gttatgggat gcatttccaa ttccattatt taaatgggtg     720
gattttcaag gcatgttaa ggctatgaaa aggacttttta agatataga ttctgttttt     780 cagaattggt tagaggaaca tattaataaa agagaaaaaa tggaggttaa tgcagaaggg     840
aatgaacaag atttcattga tgtggtgctt tcaaaaatga gtaatgaata tcttggtgaa     900
ggttactctc gtgatactgt cattaaagca acggtgttta gtttggtctt ggatgcagca     960
gacacagttg ctcttcacat aaattgggga atggcattat tgataaacaa tcaaaaggcc    1020
ttgacgaaag cacaagaaga gatagacaca aaagttggta aggacagatg ggtagaagag    1080
agtgatatta aggatttggt atacctccaa gctattgtta agaagtgtt acgattatat    1140 ccaccaggac ctttgttagt accacacgaa aatgtagaag attgtgttgt tagtggatat    1200
cacattccta aagggacaag attattcgca aacgtcatga aactgcaacg tgatcctaaa    1260
ctctggtctg atcctgatac tttcgatcca gagagattca ttgctactga tattgacttt    1320
cgtggtcagt actataagta tatcccgttt ggttctggaa gacgatcttg tccagggatg    1380
acttatgcat tgcaagtgga acacttaaca atggcacatt tgatccaagg tttcaattac    1440
agaactccaa atgacgagcc cttggatatg aaggaaggtg caggcataac tatacgtaag    1500
gtaaatcctg tggaactgat aatagcgcct cgcctggcac ctgagcttta ttaa          1554

<210> SEQ ID NO 6
```

<211> LENGTH: 1554
<212> TYPE: DNA
<213> ORGANISM: Nicotiana tabacum

<400> SEQUENCE: 6

```
atggtttctc ccgtagaagc cattgtagga ctagtaaccc ttacacttct cttctacttc    60
ctatggccca aaaaatttca ataccttca aaaccattac caccgaaaat tcccggaggg   120
tggccggtaa tcggccatct tttctacttc gatgatgacg gcgacgaccg tccattagct   180
cgaaaactcg gagacttagc tgacaaatac ggcccggttt tcactttccg gctaggcctt   240
ccgcttgtgt tagttgtaag cagttacgaa gctgtaaaag actgcttctc tacaaatgac   300
gccatttttct ccaatcgtcc agcttttctt tacggtgaat accttggcta cagtaatgcc   360
atgctatttt tgacaaaata cggaccttat tggcgaaaaa atagaaaatt agtcattcag   420
gaagttctct ctgctagtcg tctcgaaaaa ttgaagcacg tgagatttgg taaaattcaa   480
acgagcatta agagtttata cactcgaatt gatggaaatt cgagtacgat aaatctaact   540
gattggttag aagaattgaa ttttggtctg atcgtgaaaa tgatcgctgg gaaaaattat   600
gaatccggta aggagatga acaagtggag agatttagga aagcgtttaa ggatttata   660
attttatcaa tggagtttgt gttatgggat gcttttccaa ttccattgtt caaatgggtg   720
gattttcaag gccatgttaa ggccatgaaa aggacattta aggatataga ttctgttttt   780
cagaattggt tagaggaaca tgtcaagaaa agagaaaaaa tggaggttaa tgcacaaggg   840
aatgaacaag atttcattga tgtggtgctt tcaaaaatga gtaatgaata tcttgatgaa   900
ggttactctc gtgatactgt cataaaagca acagtgttta gtttggtctt ggatgctgcg   960
gacacagttg ctcttcacat gaattgggga atggcattac tgataaacaa tcaacatgcc  1020
ttgaagaaag cacaagaaga gatcgataaa aaagttggta aggaaagatg ggtagaagag  1080
agtgatatta aggatttggt ctacctccaa gctattgtta agaagtgtt acgattatat  1140
ccaccaggac ctttattagt acctcatgaa aatgtagagg attgtgttgt tagtggatat  1200
cacattccta aagggactag actattcgcg aacgttatga aattgcagcg cgatcctaaa  1260
ctctggtcaa atcctgataa gttgatcca gagagattct tcgctgatga tattgactac  1320
cgtggtcagc actatgagtt tatcccatt ggttctggaa gacgatcttg tccggggatg  1380
acttatgcat tacaagtgga acacctaaca atagcacatt tgatccaggg tttcaattac  1440
aaaactccaa atgacgagcc cttggatatg aaggaaggtg caggattaac tatacgtaaa  1500
gtaaatcctg tagaagtgac aattacggct cgcctggcac ctgagctta ttaa         1554
```

<210> SEQ ID NO 7
<211> LENGTH: 517
<212> TYPE: PRT
<213> ORGANISM: Nicotiana tabacum

<400> SEQUENCE: 7

```
Met Leu Ser Pro Ile Glu Ala Ile Val Gly Leu Val Thr Phe Thr Phe
 1               5                  10                  15

Leu Phe Phe Phe Leu Trp Thr Lys Lys Ser Gln Lys Pro Ser Lys Pro
            20                  25                  30

Leu Pro Pro Lys Ile Pro Gly Gly Trp Pro Val Ile Gly His Leu Phe
        35                  40                  45

His Phe Asn Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
```

-continued

```
                65                  70                  75                  80
        Pro Leu Val Leu Val Ser Ser Tyr Glu Ala Val Lys Asp Cys Phe
                        85                  90                  95

Ser Thr Asn Asp Ala Ile Phe Ser Asn Arg Pro Ala Phe Leu Tyr Gly
                        100                 105                 110

Asp Tyr Leu Gly Tyr Asn Asn Ala Met Leu Phe Leu Ala Asn Tyr Gly
                        115                 120                 125

Pro Tyr Trp Arg Lys Asn Arg Lys Leu Val Ile Gln Glu Val Leu Ser
                        130                 135                 140

Ala Ser Arg Leu Glu Lys Phe Lys His Val Arg Phe Ala Arg Ile Gln
        145                 150                 155                 160

Ala Ser Ile Lys Asn Leu Tyr Thr Arg Ile Asp Gly Asn Ser Ser Thr
                        165                 170                 175

Ile Asn Leu Thr Asp Trp Leu Glu Glu Leu Asn Phe Gly Leu Ile Val
                        180                 185                 190

Lys Met Ile Ala Gly Lys Asn Tyr Glu Ser Gly Lys Gly Asp Glu Gln
                        195                 200                 205

Val Glu Arg Phe Lys Lys Ala Phe Lys Asp Phe Met Ile Leu Ser Met
        210                 215                 220

Glu Phe Val Leu Trp Asp Ala Phe Pro Ile Pro Leu Phe Lys Trp Val
        225                 230                 235                 240

Asp Phe Gln Gly His Val Lys Ala Met Lys Arg Thr Phe Lys Asp Ile
                        245                 250                 255

Asp Ser Val Phe Gln Asn Trp Leu Glu Glu His Ile Asn Lys Arg Glu
                        260                 265                 270

Lys Met Glu Val Asn Ala Glu Gly Asn Glu Gln Asp Phe Ile Asp Val
                        275                 280                 285

Val Leu Ser Lys Met Ser Asn Glu Tyr Leu Gly Glu Gly Tyr Ser Arg
                        290                 295                 300

Asp Thr Val Ile Lys Ala Thr Val Phe Ser Leu Val Leu Asp Ala Ala
        305                 310                 315                 320

Asp Thr Val Ala Leu His Ile Asn Trp Gly Met Ala Leu Leu Ile Asn
                        325                 330                 335

Asn Gln Lys Ala Leu Thr Lys Ala Gln Glu Glu Ile Asp Thr Lys Val
                        340                 345                 350

Gly Lys Asp Arg Trp Val Glu Glu Ser Asp Ile Lys Asp Leu Val Tyr
                        355                 360                 365

Leu Gln Ala Ile Val Lys Glu Val Leu Arg Leu Tyr Pro Pro Gly Pro
                        370                 375                 380

Leu Leu Val Pro His Glu Asn Val Glu Asp Cys Val Val Ser Gly Tyr
        385                 390                 395                 400

His Ile Pro Lys Gly Thr Arg Leu Phe Ala Asn Val Met Lys Leu Gln
                        405                 410                 415

Arg Asp Pro Lys Leu Trp Ser Asp Pro Asp Thr Phe Asp Pro Glu Arg
                        420                 425                 430

Phe Ile Ala Thr Asp Ile Asp Phe Arg Gly Gln Tyr Tyr Lys Tyr Ile
                        435                 440                 445

Pro Phe Gly Ser Gly Arg Arg Ser Cys Pro Gly Met Thr Tyr Ala Leu
                        450                 455                 460

Gln Val Glu His Leu Thr Met Ala His Leu Ile Gln Gly Phe Asn Tyr
        465                 470                 475                 480

Arg Thr Pro Asn Asp Glu Pro Leu Asp Met Lys Glu Gly Ala Gly Ile
                        485                 490                 495
```

```
Thr Ile Arg Lys Val Asn Pro Val Glu Leu Ile Ile Ala Pro Arg Leu
                500                 505                 510

Ala Pro Glu Leu Tyr
            515

<210> SEQ ID NO 8
<211> LENGTH: 517
<212> TYPE: PRT
<213> ORGANISM: Nicotiana tabacum

<400> SEQUENCE: 8

Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
                20                  25                  30

Leu Pro Pro Lys Ile Pro Gly Gly Trp Pro Val Ile Gly His Leu Phe
                35                  40                  45

His Phe Asn Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
                100                 105                 110

Asp Tyr Leu Gly Tyr Asn Asn Ala Met Leu Phe Leu Ala Asn Tyr Gly
            115                 120                 125

Pro Tyr Trp Arg Lys Asn Arg Lys Leu Val Ile Gln Glu Val Leu Ser
    130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
                180                 185                 190

Lys Met Ile Ala Gly Lys Asn Tyr Glu Ser Gly Lys Gly Asp Glu Gln
            195                 200                 205

Val Glu Arg Phe Lys Lys Ala Phe Lys Asp Phe Met Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Ile Asn Lys Arg Glu
                260                 265                 270

Lys Met Glu Val Asn Ala Glu Gly Asn Glu Gln Asp Phe Ile Asp Val
            275                 280                 285

Val Leu Ser Lys Met Ser Asn Glu Tyr Leu Gly Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
                325                 330                 335

Asn Gln Lys Ala Leu Thr Lys Ala Gln Glu Glu Ile Asp Thr Lys Val
```

340             345             350
Gly Lys Asp Arg Trp Val Glu Glu Ser Asp Ile Lys Asp Leu Val Tyr
            355                 360                 365

Leu Gln Ala Ile Val Lys Glu Val Leu Arg Leu Tyr Pro Pro Gly Pro
        370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asp Pro Asp Thr Phe Asp Pro Glu Arg
            420                 425                 430

Phe Ile Ala Thr Asp Ile Asp Phe Arg Gly Gln Tyr Tyr Lys Tyr Ile
        435                 440                 445

Pro Phe Gly Ser Gly Arg Arg Ser Cys Pro Gly Met Thr Tyr Ala Leu
    450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
                485                 490                 495

Thr Ile Arg Lys Val Asn Pro Val Glu Leu Ile Ile Ala Pro Arg Leu
            500                 505                 510

Ala Pro Glu Leu Tyr
        515

<210> SEQ ID NO 9
<211> LENGTH: 1554
<212> TYPE: DNA
<213> ORGANISM: Nicotiana tabacum

<400> SEQUENCE: 9
atggtttctc ccgtagaagc catcgtagga ctagtaactc ttacacttct cttctacttc      60
atacggacca aaaatctca aaaccttca aaaccattac caccgaaaat ccccggaggg     120
tggccggtaa tcggccatct tttctatttc gatgacgaca gcgacgaccg tccattagca     180
cgaaaactcg gagacttagc tgacaaatac ggcccggttt tcacttttcg gctaggcctt     240
ccgcttgtgt tagttgtaag cagttacgaa gctataaaag actgcttctc tacaaatgat     300 gccatttct ccaatcgtcc agcttttctt tatggcgaat accttggcta caataatgcc      360
atgctatttt tgacaaaata cggaccttac tggcgaaaaa atagaaaatt agtcattcag     420
gaagttctct gtgctagtcg tctcgaaaaa ttgaagcacg tgagatttgg tgaaattcag     480
acgagcatta gaatttata cactcgaatt gatggaaatt cgagtacgat aaatctaacc      540
gattggttag aagaattgaa ttttggtctg atcgtgaaaa tgatcgctgg aaaaattat      600 gaatccggta aaggagatga acaagtggag agatttagga aagcgtttaa ggatttata      660 attttatcaa tggagtttgt gttatgggat gcttttccaa ttccattgtt caatgggtg      720 gattttcaag gccatgttaa ggccatgaaa aggacattta aggatataga ttctgttttt     780
cagaattggt tagaggaaca tgtcaagaaa aagaaaaaa tggaggttaa tgcagaagga     840
aatgaacaag atttcattga tgtggtgctt tcaaaaatga gtaatgaata tcttgatgaa     900
ggctactctc gtgatactgt cataaaagca acagtgttta gtttagtctt ggatgctgcg     960
gacacagttg ctcttcacat tgaattgggga atggcattat tgataaacaa tcaacatgcc    1020
ttgaagaaag cgcaagaaga gatagataaa aaagttggta aggatagatg ggtagaagag    1080

-continued

```
agtgatatta aggatttggt atacctccaa actattgtta agaagtgtt acgattatat    1140 ccaccgggac ctttattagt accccatgaa aatgtagagg attgtgttgt tagtggatat    1200
cacattccta aagggactag actattcgcg aacgttatga aattacagcg cgatcctaaa    1260
ctctggtcaa atcctgataa gttcgatcca gagagatttt tcgctgctga tattgacttt    1320
cgtggtcaac actatgagtt tatcccattt ggttctggaa gacgatcttg tccggggatg    1380
acttatgcaa tgcaagtgga acacctaaca atcgcacact tgatccaggg tttcaattac    1440
aaaactccaa atgacgagcc cttggatatg aaggaaggtg caggattaac tatacgtaag    1500
gtaaatccta tagaagtggt aattacgcct cgcctgacac ctgagcttta ttaa          1554
```

<210> SEQ ID NO 10
<211> LENGTH: 517
<212> TYPE: PRT
<213> ORGANISM: Nicotiana tabacum

<400> SEQUENCE: 10

```
Met Val Ser Pro Val Glu Ala Ile Val Gly Leu Val Thr Leu Thr Leu
 1               5                  10                  15

Leu Phe Tyr Phe Ile Arg Thr Lys Lys Ser Gln Lys Pro Ser Lys Pro
            20                  25                  30

Leu Pro Pro Lys Ile Pro Gly Gly Trp Pro Val Ile Gly His Leu Phe
        35                  40                  45

Tyr Phe Asp Asp Asp Ser Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Ile Lys Asp Cys Phe
                85                  90                  95

Ser Thr Asn Asp Ala Ile Phe Ser Asn Arg Pro Ala Phe Leu Tyr Gly
            100                 105                 110

Glu Tyr Leu Gly Tyr Asn Asn Ala Met Leu Phe Leu Thr Lys Tyr Gly
        115                 120                 125

Pro Tyr Trp Arg Lys Asn Arg Lys Leu Val Ile Gln Glu Val Leu Cys
    130                 135                 140

Ala Ser Arg Leu Glu Lys Leu Lys His Val Arg Phe Gly Glu Ile Gln
145                 150                 155                 160

Thr Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Arg Lys Ala Phe Lys Asp Phe Ile Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu His Val Lys Lys Glu
            260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Asp Glu Gly Tyr Ser Arg
```

```
              290                 295                 300
Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Ile Asp Lys Lys Val
            340                 345                 350

Gly Lys Asp Arg Trp Val Glu Glu Ser Asp Ile Lys Asp Leu Val Tyr
        355                 360                 365

Leu Gln Thr Ile Val Lys Glu Val Leu Arg Leu Tyr Pro Pro Gly Pro
370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asn Pro Asp Lys Phe Asp Pro Glu Arg
            420                 425                 430

Phe Phe Ala Ala Asp Ile Asp Phe Arg Gly Gln His Tyr Glu Phe Ile
        435                 440                 445

Pro Phe Gly Ser Gly Arg Arg Ser Cys Pro Gly Met Thr Tyr Ala Met
    450                 455                 460

Gln Val Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
                485                 490                 495

Thr Ile Arg Lys Val Asn Pro Ile Glu Val Val Ile Thr Pro Arg Leu
            500                 505                 510

Thr Pro Glu Leu Tyr
        515

<210> SEQ ID NO 11
<211> LENGTH: 1554
<212> TYPE: DNA
<213> ORGANISM: Nicotiana tabacum
<220> FEATURE:
<221> NAME/KEY: Mutation
<222> LOCATION: (1141)..(1141)
<223> OTHER INFORMATION: C to T

<400> SEQUENCE: 11
atggtttctc ccgtagaagc catcgtagga ctagtaactc ttacacttct cttctacttc      60
atacggacca aaaatctca  aaaaccttca aaaccattac caccgaaaat ccccggaggg     120
tggccggtaa tcggccatct tttctatttc gatgacgaca cgacgaccg tccattagca      180 cgaaaactcg gagcttagc  tgacaaatac ggcccggttt tcacttttcg gctaggcctt     240
ccgcttgtgt tagttgtaag cagttacgaa gctataaaag actgcttctc tacaaatgat    300 gccatttttct ccaatcgtcc agcttttctt tatggcgaat accttggcta caataatgcc    360
atgctatttt tgacaaaata cggaccttac tggcgaaaaa atagaaaatt agtcattcag    420
gaagttctct gtgctagtcg tctcgaaaaa ttgaagcacg tgagatttgg tgaaattcag     480
acgagcatta agaatttata cactcgaatt gatggaaatt cgagtacgat aaatctaacc     540
gattggttag aagaattgaa ttttggtctg atcgtgaaaa tgatcgctgg gaaaaattat     600
gaatccggta aggagatga  acaagtggag agatttagga aagcgtttaa ggattttata    660
attttatcaa tggagtttgt gttatgggat gcttttccaa ttccattgtt caaatgggtg    720
```

```
gattttcaag gccatgttaa ggccatgaaa aggacattta aggatataga ttctgttttt    780
cagaattggt tagaggaaca tgtcaagaaa aagaaaaaa tggaggttaa tgcagaagga    840
aatgaacaag atttcattga tgtggtgctt tcaaaaatga gtaatgaata tcttgatgaa    900
ggctactctc gtgatactgt cataaaagca acagtgttta gtttagtctt ggatgctgcg    960
gacacagttg ctcttcacat gaattgggga atggcattat tgataaacaa tcaacatgcc   1020
ttgaagaaag cgcaagaaga gatagataaa aaagttggta aggatagatg ggtagaagag   1080
agtgatatta aggatttggt atacctccaa actattgtta agaagtgtt acgattatat    1140 tcaccgggac ctttattagt accccatgaa aatgtagagg attgtgttgt tagtggatat   1200
cacattccta aagggactag actattcgcg aacgttatga aattacagcg cgatcctaaa   1260
ctctggtcaa atcctgataa gttcgatcca gagagatttt tcgctgctga tattgacttt   1320
cgtggtcaac actatgagtt tatcccattt ggttctggaa gacgatcttg tccggggatg   1380
acttatgcaa tgcaagtgga acacctaaca atcgcacact tgatccaggg tttcaattac   1440
aaaactccaa atgacgagcc cttggatatg aaggaaggtg caggattaac tatacgtaag   1500
gtaaatccta tagaagtggt aattacgcct cgcctgacac ctgagcttta ttaa          1554
```

<210> SEQ ID NO 12
<211> LENGTH: 571
<212> TYPE: PRT
<213> ORGANISM: Nicotiana tabacum

<400> SEQUENCE: 12

```
Met Val Ser Pro Val Glu Ala Ile Val Gly Leu Val Thr Leu Thr Leu
1               5                   10                  15

Leu Phe Tyr Phe Ile Arg Thr Lys Lys Ser Gln Lys Pro Ser Lys Pro
            20                  25                  30

Leu Pro Pro Lys Ile Pro Gly Gly Trp Pro Val Ile Gly His Leu Phe
        35                  40                  45

Tyr Phe Asp Asp Asp Ser Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Ile Lys Asp Cys Phe
                85                  90                  95

Ser Thr Asn Asp Ala Ile Phe Ser Asn Arg Pro Ala Phe Leu Tyr Gly
            100                 105                 110

Glu Tyr Leu Gly Tyr Asn Asn Ala Met Leu Phe Leu Thr Lys Tyr Gly
        115                 120                 125

Pro Tyr Trp Arg Lys Asn Arg Lys Leu Val Ile Gln Glu Val Leu Cys
    130                 135                 140

Ala Ser Arg Leu Glu Lys Leu Lys His Val Arg Phe Gly Glu Ile Gln
145                 150                 155                 160

Thr Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Arg Lys Ala Phe Lys Asp Phe Ile Ile Leu Ser Met
    210                 215                 220
```

-continued

```
Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
            245                 250                 255

Asp Ser Val Phe Gln Asn Trp Leu Glu Glu His Val Lys Lys Lys Glu
            260                 265                 270

Lys Met Glu Val Asn Ala Glu Gly Asn Glu Gln Asp Phe Ile Asp Val
            275                 280                 285

Val Leu Ser Lys Met Ser Asn Glu Tyr Leu Asp Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Glu Ile Asp Lys Lys Val
            340                 345                 350

Gly Lys Asp Arg Trp Val Glu Glu Ser Asp Ile Lys Asp Leu Val Tyr
            355                 360                 365

Leu Gln Thr Ile Val Lys Glu Val Leu Arg Leu Tyr Ser Pro Gly Pro
    370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asn Pro Asp Lys Phe Asp Pro Glu Arg
            420                 425                 430

Phe Phe Ala Ala Asp Ile Asp Phe Arg Gly Gln His Tyr Glu Phe Ile
            435                 440                 445

Pro Phe Gly Ser Gly Arg Arg Ser Cys Pro Gly Met Thr Tyr Ala Met
    450                 455                 460

Gln Val Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
            485                 490                 495

Thr Ile Arg Lys Val Asn Pro Ile Glu Val Val Ile Thr Pro Arg Leu
            500                 505                 510

Thr Pro Glu Leu Tyr Gly Thr Ala Ala Thr Cys Cys Thr Ala Thr
    515                 520                 525

Ala Gly Ala Ala Gly Thr Gly Gly Thr Ala Ala Thr Thr Ala Cys Gly
530                 535                 540

Cys Cys Thr Cys Gly Cys Cys Thr Gly Ala Cys Ala Cys Cys Thr Gly
545                 550                 555                 560

Ala Gly Cys Thr Thr Thr Ala Thr Thr Ala Ala
                565                 570
```

DARK TOBACCO INBREDS AND HYBRIDS COMPRISING REDUCED NICOTINE DEMETHYLATION AND NORNICOTINE

CROSS-REFERENCE TO RELATED APPLICATIONS

This application is a continuation of U.S. patent application Ser. No. 16/774,831, filed Jan. 28, 2020, which is a continuation of U.S. patent application Ser. No. 15/808,202, filed Nov. 9, 2017 (now U.S. Pat. No. 10,582,680, issued Mar. 10, 2020), which claims priority to U.S. Provisional Application No. 62/420,527, filed Nov. 10, 2016, U.S. Provisional Application No. 62/441,855, filed Jan. 3, 2017 and U.S. Provisional Application No. 62/558,072, filed Sep. 13, 2017. Each of these U.S. Applications are incorporated by reference herein in their entireties.

INCORPORATION OF SEQUENCE LISTING

A sequence listing contained in the file name "P34475US05_SEQ.txt" which is 38,262 bytes (measured in MS-Windows®) and created on Nov. 17, 2021, is filed electronically herewith and incorporated by reference in its entirety.

FIELD

The present disclosure provides tobacco inbred plants TND950 (phph) SRC, Narrow Leaf Madole (phph) SRC, Narrow Leaf Madole SRC, CMS TND950 SRC, CMS Narrow Leaf Madole SRC, CMS KY171 SRC and hybrid cultivars PD7305 SRC, PD7309 SRC, PD7312 SRC, PD7318 SRC, and PD7319 SRC. The present disclosure also provides parts of such plants and products made from those parts. The present disclosure also includes progeny of the provided plants including hybrids.

BACKGROUND

Tobacco (*Nicotiana tabacum* L.) is an important commercial crop in the United States as well as in other countries. In tobacco plants, N-demethylation of nicotine results in nornicotine, a secondary alkaloid known to be a precursor for formation of N-Nitrosonornicotine ("NNN") in cured leaves. At high levels, NNN is an undesired component of cured leaves.

The predominant alkaloid found in commercial tobacco varieties is nicotine, typically accounting for 90-95% of the total alkaloid pool. The remaining alkaloid fraction is comprised primarily of three additional pyridine alkaloids: nornicotine, anabasine, and anatabine. Nornicotine is generated directly from nicotine through the activity of the enzyme nicotine N-demethylase. Nornicotine usually represents less than 5% of the total pyridine alkaloid pool, but through a process termed "conversion," tobacco plants that initially produce very low amounts of nornicotine give rise to progeny that metabolically "convert" a large percentage of leaf nicotine to nornicotine. In tobacco plants that have genetically converted (termed "converters"), the great majority of nornicotine production occurs during the senescence and curing of the mature leaf (Wernsman and Matzinger (1968), *Tob. Sci.,* 12:226-228). Burley tobaccos are particularly prone to genetic conversion, with rates as high as 20% per generation observed in some cultivars.

During the curing and processing of the tobacco leaf, a portion of the nornicotine is metabolized to the compound NNN, a tobacco-specific nitrosamine (TSNA) that has been reported to be carcinogenic in laboratory animals (Hecht and Hoffmann (1990), *Cancer Surveys,* 8:273-294; Hoffmann et al. (1994), *J. Toxicol. Environ. Health,* 41:1-52; Hecht (1998), *Chem. Res. Toxicol.,* 11:559-603). In flue-cured tobaccos, TSNAs are found to be predominantly formed through the reaction of alkaloids with the minute amounts of nitrogen oxides present in combustion gases formed by the direct-fired heating systems found in traditional curing barns (Peele and Gentry (1999), "Formation of Tobacco-specific Nitrosamines in Flue-cured Tobacco," CORESTA Meeting, Agro-Phyto Groups, Suzhou, China). Retrofitting these curing barns with heat-exchangers virtually eliminated the mixing of combustion gases with the curing air and dramatically reduced the formation of TSNAs in tobaccos cured in this manner (Boyette and Hamm (2001), *Rec. Adv. Tob. Sci.,* 27:17-22). In contrast, in the air-cured Burley tobaccos, TSNA formation proceeds primarily through reaction of tobacco alkaloids with nitrite, a process catalyzed by leaf-borne microbes (Bush et al. (2001), *Rec. Adv. Tob. Sci.,* 27:23-46). Thus far, attempts to reduce TSNAs through modification of curing conditions while maintaining acceptable quality standards continue to be challenging for the air-cured tobaccos.

SUMMARY

In an aspect, the present disclosure includes a seed of tobacco cultivar TND950 (phph) SRC, a representative sample seed of the cultivar having been deposited with the American Type Culture Collection (ATCC) under ATCC Accession No. PTA-123665.

In another aspect, the present disclosure includes a tobacco plant, or part thereof, produced by growing the seed of tobacco cultivar TND950 (phph) SRC.

In a further aspect, the present disclosure includes a harvested leaf, or part thereof, of a tobacco plant, or part thereof, produced by growing the seed of tobacco cultivar TND950 (phph) SRC.

In an aspect, the present disclosure includes a harvested leaf, or part thereof, of a tobacco plant, produced by growing the seed of tobacco cultivar TND950 (phph) SRC, where the leaf has a reduced amount of nornicotine and/or N'-nitrosonornicotine (NNN).

In an aspect, the present disclosure includes a harvested leaf, or part thereof, produced by growing the seed of tobacco cultivar TND950 (phph) SRC, where the leaf has a reduced amount of nornicotine and/or N'-nitrosonornicotine (NNN), where the reduced amount of nornicotine and/or N'-nitrosonornicotine (NNN) is reduced in a smoke stream produced from the leaf.

In a further aspect, the present disclosure includes a tobacco product, prepared from a tobacco plant, or part thereof, produced by growing the seed of tobacco cultivar TND950 (phph) SRC, where the product is selected from the group consisting of pipe tobacco, cigar tobacco, cigarette tobacco, chewing tobacco, leaf tobacco, shredded tobacco, cut tobacco, and any combination thereof.

In an aspect, the present disclosure includes a tobacco product, prepared from a tobacco plant, or part thereof, produced by growing the seed of tobacco cultivar TND950 (phph) SRC, where the product is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, cut tobacco, loose leaf chewing tobacco, plug chewing tobacco, moist snuff, and nasal snuff.

In another aspect, the present disclosure includes a tobacco product, prepared from a tobacco plant, or part thereof, produced by growing the seed of tobacco cultivar TND950 (phph) SRC, where the product is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, cut tobacco, loose leaf chewing tobacco, and further where the product has a reduced amount of nornicotine and/or N'-nitrosonornicotine (NNN).

In a further aspect, the present disclosure includes a second tobacco product prepared or produced from a first tobacco product prepared from a tobacco plant, or part thereof, produced by growing the seed of tobacco cultivar TND950 (phph) SRC, where first product is selected from the group consisting of pipe tobacco, cigar tobacco, cigarette tobacco, chewing tobacco, leaf tobacco, shredded tobacco, cut tobacco and any combination thereof, and the second tobacco product is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, cut tobacco, loose leaf chewing tobacco, plug chewing tobacco, moist snuff, and nasal snuff. In some aspects, the first and/or second product comprises a reduced amount of nornicotine and/or N'-nitrosonornicotine (NNN).

In an aspect, the present disclosure includes a part of a tobacco plant, produced by growing the seed of tobacco cultivar TND950 (phph) SRC, where the part is selected from the group consisting of leaf, pollen, ovule, embryo, cotyledon, hypocotyl, meristematic cell, protoplast, root, root tip, pistil, anther, flower, shoot, stem, pod and petiole.

In another aspect, the present disclosure includes a tissue culture produced from a protoplast or cell from a tobacco plant, or part thereof, produced by growing the seed of tobacco cultivar TND950 (phph) SRC, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole.

In an aspect, the present disclosure includes a tobacco plant regenerated from a tissue culture produced from a protoplast or cell from a tobacco plant, or part thereof, produced by growing the seed of tobacco cultivar TND950 (phph) SRC, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole where the regenerated plant has all, or essentially all of the morphological and physiological characteristics of cultivar TND950 (phph) SRC.

In an aspect, the present disclosure includes an $F_1$ progeny plant of tobacco cultivar TND950 (phph) SRC.

In another aspect, the present disclosure includes an $F_1$ progeny plant of tobacco cultivar TND950 (phph) SRC, where the $F_1$ plant is cytoplasmic male sterile (CMS).

In another aspect, the present disclosure includes an $F_1$ progeny seed produced crossing two tobacco plants and harvesting the resultant tobacco seed, where at least one tobacco plant is a tobacco plant produced by growing the seed of tobacco cultivar TND950 (phph) SRC, where at least one tobacco plant is cytoplasmic male sterile (CMS).

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar TND950 (phph) SRC.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar TND950 (phph) SRC, where the plant of tobacco cultivar TND950 (phph) SRC is the male parent.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar TND950 (phph) SRC, where the plant of tobacco cultivar TND950 (phph) SRC is the female parent.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar TND950 (phph) SRC, where at least one tobacco plant is cytoplasmic male sterile (CMS).

In an aspect, the present disclosure also includes a container of $F_1$ progeny seeds produced by crossing two tobacco plants and harvesting the resultant tobacco seed, where at least one tobacco plant is a tobacco plant produced by growing the seed of tobacco cultivar TND950 (phph) SRC, where at least one tobacco plant is cytoplasmic male sterile (CMS).

In an aspect, the present disclosure includes an $F_1$ progeny plant produced by growing a seed produced by crossing two tobacco plants and harvesting the resultant tobacco seed, where at least one tobacco plant is a tobacco plant produced by growing the seed of tobacco cultivar TND950 (phph) SRC, and where at least one tobacco plant is cytoplasmic male sterile (CMS).

In an aspect, the present disclosure also includes a harvested leaf of an $F_1$ progeny plant produced by growing a seed produced by a method of comprising crossing two tobacco plants and harvesting the resultant tobacco seed, where at least one tobacco plant is a tobacco plant produced by growing the seed of tobacco cultivar TND950 (phph) SRC, where at least one tobacco plant is cytoplasmic male sterile (CMS).

In another aspect, the present disclosure further includes a harvested leaf of an $F_1$ progeny plant having a reduced amount of nornicotine and/or N'-nitrosonornicotine (NNN) produced by growing a seed produced by a method of comprising crossing two tobacco plants and harvesting the resultant tobacco seed, where at least one tobacco plant is a tobacco plant produced by growing the seed of tobacco cultivar TND950 (phph) SRC, where at least one tobacco plant is cytoplasmic male sterile (CMS).

In an aspect, the present disclosure also includes a harvested leaf of an $F_1$ progeny plant having a reduced amount of nornicotine and/or N'-nitrosonornicotine (NNN) in a smoke stream produced from the leaf, where the plant is produced by growing a seed produced by crossing two tobacco plants and harvesting the resultant tobacco seed, where at least one tobacco plant is a tobacco plant produced by growing the seed of tobacco cultivar TND950 (phph) SRC, where at least one tobacco plant is cytoplasmic male sterile (CMS).

In an aspect, the present disclosure includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar TND950 (phph) SRC, where at least one tobacco plant is cytoplasmic male sterile, and where the tobacco product is selected from the group consisting of pipe tobacco, cigar tobacco, cigarette tobacco, chewing tobacco, leaf tobacco, shredded tobacco, cut tobacco and any combination thereof.

In an aspect, the present disclosure further includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar TND950 (phph) SRC, where at least one tobacco plant is cytoplasmic male sterile, and where the tobacco product is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, cut tobacco, loose leaf chewing tobacco, plug chewing tobacco, moist snuff, and nasal snuff.

In an aspect, the present disclosure further includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar TND950 (phph) SRC, where at least one tobacco plant is cytoplasmic male sterile, and where the tobacco product is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, cut tobacco, loose leaf chewing tobacco, and further where the product has a reduced amount of nornicotine and/or N'-nitrosonornicotine (NNN).

In an aspect, the present disclosure includes a seed of tobacco cultivar Narrow Leaf Madole (phph) SRC, a representative sample seed of the cultivar having been deposited with the American Type Culture Collection (ATCC) under ATCC Accession No. PTA-123664.

In another aspect, the present disclosure includes a tobacco plant, or part thereof, produced by growing the seed of tobacco cultivar Narrow Leaf Madole (phph) SRC.

In a further aspect, the present disclosure includes a harvested leaf, or part thereof, of a tobacco plant, or part thereof, produced by growing the seed of tobacco cultivar Narrow Leaf Madole (phph) SRC.

In an aspect, the present disclosure includes a harvested leaf, or part thereof, of a tobacco plant, produced by growing the seed of tobacco cultivar Narrow Leaf Madole (phph) SRC, where the leaf has a reduced amount of nornicotine and/or N'-nitrosonornicotine (NNN).

In an aspect, the present disclosure includes a harvested leaf, or part thereof, produced by growing the seed of tobacco cultivar Narrow Leaf Madole (phph) SRC, where the leaf has a reduced amount of nornicotine and/or N'-nitrosonornicotine (NNN), where the reduced amount of nornicotine and/or N'-nitrosonornicotine (NNN) is reduced in a smoke stream produced from the leaf.

In a further aspect, the present disclosure includes a tobacco product, prepared from a tobacco plant, or part thereof, produced by growing the seed of tobacco cultivar Narrow Leaf Madole (phph) SRC, where the product is selected from the group consisting of pipe tobacco, cigar tobacco, cigarette tobacco, chewing tobacco, leaf tobacco, shredded tobacco, cut tobacco, and any combination thereof.

In an aspect, the present disclosure includes a tobacco product, prepared from a tobacco plant, or part thereof, produced by growing the seed of tobacco cultivar Narrow Leaf Madole (phph) SRC, where the product is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, cut tobacco, loose leaf chewing tobacco, plug chewing tobacco, moist snuff, and nasal snuff.

In another aspect, the present disclosure includes a tobacco product, prepared from a tobacco plant, or part thereof, produced by growing the seed of tobacco cultivar Narrow Leaf Madole (phph) SRC, where the product is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, cut tobacco, loose leaf chewing tobacco, and further where the product has a reduced amount of nornicotine and/or N'-nitrosonornicotine (NNN).

In a further aspect, the present disclosure includes a second tobacco product prepared or produced from a first tobacco product prepared from a tobacco plant, or part thereof, produced by growing the seed of tobacco cultivar Narrow Leaf Madole (phph) SRC, where first product is selected from the group consisting of pipe tobacco, cigar tobacco, cigarette tobacco, chewing tobacco, leaf tobacco, shredded tobacco, cut tobacco and any combination thereof, and the second tobacco product is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, cut tobacco, loose leaf chewing tobacco, plug chewing tobacco, moist snuff, and nasal snuff. In some aspects, the first and/or second product comprises a reduced amount of nornicotine and/or N'-nitrosonornicotine (NNN).

In an aspect, the present disclosure includes a part of a tobacco plant, produced by growing the seed of tobacco cultivar Narrow Leaf Madole (phph) SRC, where the part is selected from the group consisting of leaf, pollen, ovule, embryo, cotyledon, hypocotyl, meristematic cell, protoplast, root, root tip, pistil, anther, flower, shoot, stem, pod and petiole.

In another aspect, the present disclosure includes a tissue culture produced from a protoplast or cell from a tobacco plant, or part thereof, produced by growing the seed of tobacco cultivar Narrow Leaf Madole (phph) SRC, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole.

In an aspect, the present disclosure includes a tobacco plant regenerated from a tissue culture produced from a protoplast or cell from a tobacco plant, or part thereof, produced by growing the seed of tobacco cultivar Narrow Leaf Madole (phph) SRC, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole where the regenerated plant has all, or essentially all of the morphological and physiological characteristics of cultivar Narrow Leaf Madole (phph) SRC.

In an aspect, the present disclosure includes an $F_1$ progeny plant of tobacco cultivar Narrow Leaf Madole (phph) SRC.

In another aspect, the present disclosure includes an $F_1$ progeny plant of tobacco cultivar Narrow Leaf Madole (phph) SRC, where the $F_1$ plant is cytoplasmic male sterile (CMS).

In another aspect, the present disclosure includes an $F_1$ progeny seed produced crossing two tobacco plants and harvesting the resultant tobacco seed, where at least one tobacco plant is a tobacco plant produced by growing the seed of tobacco cultivar Narrow Leaf Madole (phph) SRC, where at least one tobacco plant is cytoplasmic male sterile (CMS).

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar Narrow Leaf Madole (phph) SRC.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar Narrow Leaf Madole (phph) SRC, where the plant of tobacco cultivar Narrow Leaf Madole (phph) SRC is the male parent.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar Narrow Leaf Madole (phph) SRC, where the plant of tobacco cultivar Narrow Leaf Madole (phph) SRC is the female parent.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar Narrow Leaf Madole (phph) SRC, where at least one tobacco plant is cytoplasmic male sterile (CMS).

In an aspect, the present disclosure also includes a container of $F_1$ progeny seeds produced by crossing two tobacco plants and harvesting the resultant tobacco seed, where at least one tobacco plant is a tobacco plant produced by growing the seed of tobacco cultivar Narrow Leaf Madole (phph) SRC, where at least one tobacco plant is cytoplasmic male sterile (CMS).

In an aspect, the present disclosure includes an $F_1$ progeny plant produced by growing a seed produced by crossing two tobacco plants and harvesting the resultant tobacco seed, where at least one tobacco plant is a tobacco plant produced by growing the seed of tobacco cultivar Narrow Leaf Madole (phph) SRC, and where at least one tobacco plant is cytoplasmic male sterile (CMS).

In an aspect, the present disclosure also includes a harvested leaf of an $F_1$ progeny plant produced by growing a seed produced by a method of comprising crossing two tobacco plants and harvesting the resultant tobacco seed, where at least one tobacco plant is a tobacco plant produced by growing the seed of tobacco cultivar Narrow Leaf Madole (phph) SRC, where at least one tobacco plant is cytoplasmic male sterile (CMS).

In another aspect, the present disclosure further includes a harvested leaf of an $F_1$ progeny plant having a reduced amount of nornicotine and/or N'-nitrosonornicotine (NNN) produced by growing a seed produced by a method of comprising crossing two tobacco plants and harvesting the resultant tobacco seed, where at least one tobacco plant is a tobacco plant produced by growing the seed of tobacco cultivar Narrow Leaf Madole (phph) SRC, where at least one tobacco plant is cytoplasmic male sterile (CMS).

In an aspect, the present disclosure also includes a harvested leaf of an $F_1$ progeny plant having a reduced amount of nornicotine and/or N'-nitrosonornicotine (NNN) in a smoke stream produced from the leaf, where the plant is produced by growing a seed produced by crossing two tobacco plants and harvesting the resultant tobacco seed, where at least one tobacco plant is a tobacco plant produced by growing the seed of tobacco cultivar Narrow Leaf Madole (phph) SRC, where at least one tobacco plant is cytoplasmic male sterile (CMS).

In an aspect, the present disclosure includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar Narrow Leaf Madole (phph) SRC, where at least one tobacco plant is cytoplasmic male sterile, and where the tobacco product is selected from the group consisting of pipe tobacco, cigar tobacco, cigarette tobacco, chewing tobacco, leaf tobacco, shredded tobacco, cut tobacco and any combination thereof.

In an aspect, the present disclosure further includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar Narrow Leaf Madole (phph) SRC, where at least one tobacco plant is cytoplasmic male sterile, and where the tobacco product is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, cut tobacco, loose leaf chewing tobacco, plug chewing tobacco, moist snuff, and nasal snuff.

In an aspect, the present disclosure further includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar Narrow Leaf Madole (phph) SRC, where at least one tobacco plant is cytoplasmic male sterile, and where the tobacco product is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, cut tobacco, loose leaf chewing tobacco, and further where the product has a reduced amount of nornicotine and/or N'-nitrosonornicotine (NNN).

In an aspect, the present disclosure includes a seed of tobacco cultivar Narrow Leaf Madole SRC, a representative sample seed of the cultivar having been deposited with the American Type Culture Collection (ATCC) under ATCC Accession No. PTA-123663.

In another aspect, the present disclosure includes a tobacco plant, or part thereof, produced by growing the seed of tobacco cultivar Narrow Leaf Madole SRC.

In a further aspect, the present disclosure includes a harvested leaf, or part thereof, of a tobacco plant, or part thereof, produced by growing the seed of tobacco cultivar Narrow Leaf Madole SRC.

In an aspect, the present disclosure includes a harvested leaf, or part thereof, of a tobacco plant, produced by growing the seed of tobacco cultivar Narrow Leaf Madole SRC, where the leaf has a reduced amount of nornicotine and/or N'-nitrosonornicotine (NNN).

In an aspect, the present disclosure includes a harvested leaf, or part thereof, produced by growing the seed of tobacco cultivar Narrow Leaf Madole SRC, where the leaf has a reduced amount of nornicotine and/or N'-nitrosonornicotine (NNN), where the reduced amount of nornicotine and/or N'-nitrosonornicotine (NNN) is reduced in a smoke stream produced from the leaf.

In a further aspect, the present disclosure includes a tobacco product, prepared from a tobacco plant, or part thereof, produced by growing the seed of tobacco cultivar Narrow Leaf Madole SRC, where the product is selected from the group consisting of pipe tobacco, cigar tobacco, cigarette tobacco, chewing tobacco, leaf tobacco, shredded tobacco, cut tobacco, and any combination thereof.

In an aspect, the present disclosure includes a tobacco product, prepared from a tobacco plant, or part thereof, produced by growing the seed of tobacco cultivar Narrow Leaf Madole SRC, where the product is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, cut tobacco, loose leaf chewing tobacco, plug chewing tobacco, moist snuff, and nasal snuff.

In another aspect, the present disclosure includes a tobacco product, prepared from a tobacco plant, or part thereof, produced by growing the seed of tobacco cultivar Narrow Leaf Madole SRC, where the product is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, cut tobacco, loose leaf chewing tobacco, and further where the product has a reduced amount of nornicotine and/or N'-nitrosonornicotine (NNN).

In a further aspect, the present disclosure includes a second tobacco product prepared or produced from a first tobacco product prepared from a tobacco plant, or part thereof, produced by growing the seed of tobacco cultivar Narrow Leaf Madole SRC, where first product is selected from the group consisting of pipe tobacco, cigar tobacco, cigarette tobacco, chewing tobacco, leaf tobacco, shredded tobacco, cut tobacco and any combination thereof, and the second tobacco product is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, cut tobacco, loose leaf chewing tobacco, plug chewing tobacco, moist snuff, and nasal snuff. In some aspects, the first and/or second product comprises a reduced amount of nornicotine and/or N'-nitrosonornicotine (NNN).

In an aspect, the present disclosure includes a part of a tobacco plant, produced by growing the seed of tobacco cultivar Narrow Leaf Madole SRC, where the part is selected from the group consisting of leaf, pollen, ovule, embryo, cotyledon, hypocotyl, meristematic cell, protoplast, root, root tip, pistil, anther, flower, shoot, stem, pod and petiole.

In another aspect, the present disclosure includes a tissue culture produced from a protoplast or cell from a tobacco plant, or part thereof, produced by growing the seed of tobacco cultivar Narrow Leaf Madole SRC, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole.

In an aspect, the present disclosure includes a tobacco plant regenerated from a tissue culture produced from a protoplast or cell from a tobacco plant, or part thereof, produced by growing the seed of tobacco cultivar Narrow Leaf Madole SRC, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole where the regenerated plant has all, or essentially all of the morphological and physiological characteristics of cultivar Narrow Leaf Madole SRC.

In an aspect, the present disclosure includes an $F_1$ progeny plant of tobacco cultivar Narrow Leaf Madole SRC.

In another aspect, the present disclosure includes an $F_1$ progeny plant of tobacco cultivar Narrow Leaf Madole SRC, where the $F_1$ plant is cytoplasmic male sterile (CMS).

In another aspect, the present disclosure includes an $F_1$ progeny seed produced crossing two tobacco plants and harvesting the resultant tobacco seed, where at least one tobacco plant is a tobacco plant produced by growing the seed of tobacco cultivar Narrow Leaf Madole SRC, where at least one tobacco plant is cytoplasmic male sterile (CMS).

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar Narrow Leaf Madole SRC.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar Narrow Leaf Madole SRC, where the plant of tobacco cultivar Narrow Leaf Madole SRC is the male parent.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar Narrow Leaf Madole SRC, where the plant of tobacco cultivar Narrow Leaf Madole SRC is the female parent.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar Narrow Leaf Madole SRC, where at least one tobacco plant is cytoplasmic male sterile (CMS).

In an aspect, the present disclosure also includes a container of $F_1$ progeny seeds produced by crossing two tobacco plants and harvesting the resultant tobacco seed, where at least one tobacco plant is a tobacco plant produced by growing the seed of tobacco cultivar Narrow Leaf Madole SRC, where at least one tobacco plant is cytoplasmic male sterile (CMS).

In an aspect, the present disclosure includes an $F_1$ progeny plant produced by growing a seed produced by crossing two tobacco plants and harvesting the resultant tobacco seed, where at least one tobacco plant is a tobacco plant produced by growing the seed of tobacco cultivar Narrow Leaf Madole SRC, and where at least one tobacco plant is cytoplasmic male sterile (CMS).

In an aspect, the present disclosure also includes a harvested leaf of an $F_1$ progeny plant produced by growing a seed produced by a method of comprising crossing two tobacco plants and harvesting the resultant tobacco seed, where at least one tobacco plant is a tobacco plant produced by growing the seed of tobacco cultivar Narrow Leaf Madole SRC, where at least one tobacco plant is cytoplasmic male sterile (CMS).

In another aspect, the present disclosure further includes a harvested leaf of an $F_1$ progeny plant having a reduced amount of nornicotine and/or N'-nitrosonornicotine (NNN) produced by growing a seed produced by a method of comprising crossing two tobacco plants and harvesting the resultant tobacco seed, where at least one tobacco plant is a tobacco plant produced by growing the seed of tobacco cultivar Narrow Leaf Madole SRC, where at least one tobacco plant is cytoplasmic male sterile (CMS).

In an aspect, the present disclosure also includes a harvested leaf of an $F_1$ progeny plant having a reduced amount of nornicotine and/or N'-nitrosonornicotine (NNN) in a smoke stream produced from the leaf, where the plant is produced by growing a seed produced by crossing two tobacco plants and harvesting the resultant tobacco seed, where at least one tobacco plant is a tobacco plant produced by growing the seed of tobacco cultivar Narrow Leaf Madole SRC, where at least one tobacco plant is cytoplasmic male sterile (CMS).

In an aspect, the present disclosure includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar Narrow Leaf Madole SRC, where at least one tobacco plant is cytoplasmic male sterile, and where the tobacco product is selected from the group consisting of pipe tobacco, cigar tobacco, cigarette tobacco, chewing tobacco, leaf tobacco, shredded tobacco, cut tobacco and any combination thereof.

In an aspect, the present disclosure further includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar Narrow Leaf Madole SRC, where at least one tobacco plant is cytoplasmic male sterile, and where the tobacco product is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, cut tobacco, loose leaf chewing tobacco, plug chewing tobacco, moist snuff, and nasal snuff.

In an aspect, the present disclosure further includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar Narrow Leaf Madole SRC, where at least one tobacco plant is cytoplasmic male sterile, and where the tobacco product is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, cut tobacco, loose leaf chewing tobacco, and further where the product has a reduced amount of nornicotine and/or N'-nitrosonornicotine (NNN).

In an aspect, the present disclosure includes a seed of tobacco cultivar CMS TND950 SRC, a representative sample seed of the cultivar having been deposited with the American Type Culture Collection (ATCC) under ATCC Accession No. PTA-123662.

In another aspect, the present disclosure includes a tobacco plant, or part thereof, produced by growing the seed of tobacco cultivar CMS TND950 SRC.

In a further aspect, the present disclosure includes a harvested leaf, or part thereof, of a tobacco plant, or part thereof, produced by growing the seed of tobacco cultivar CMS TND950 SRC.

In an aspect, the present disclosure includes a harvested leaf, or part thereof, of a tobacco plant, produced by growing the seed of tobacco cultivar CMS TND950 SRC, where the leaf has a reduced amount of nornicotine and/or N'-nitrosonornicotine (NNN).

In an aspect, the present disclosure includes a harvested leaf, or part thereof, produced by growing the seed of tobacco cultivar CMS TND950 SRC, where the leaf has a reduced amount of nornicotine and/or N'-nitrosonornicotine (NNN), where the reduced amount of nornicotine and/or N'-nitrosonornicotine (NNN) is reduced in a smoke stream produced from the leaf.

In a further aspect, the present disclosure includes a tobacco product, prepared from a tobacco plant, or part thereof, produced by growing the seed of tobacco cultivar CMS TND950 SRC, where the product is selected from the group consisting of pipe tobacco, cigar tobacco, cigarette tobacco, chewing tobacco, leaf tobacco, shredded tobacco, cut tobacco, and any combination thereof.

In an aspect, the present disclosure includes a tobacco product, prepared from a tobacco plant, or part thereof, produced by growing the seed of tobacco cultivar CMS TND950 SRC, where the product is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, cut tobacco, loose leaf chewing tobacco, plug chewing tobacco, moist snuff, and nasal snuff.

In another aspect, the present disclosure includes a tobacco product, prepared from a tobacco plant, or part thereof, produced by growing the seed of tobacco cultivar CMS TND950 SRC, where the product is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, cut tobacco, loose leaf chewing tobacco, and further where the product has a reduced amount of nornicotine and/or N'-nitrosonornicotine (NNN).

In a further aspect, the present disclosure includes a second tobacco product prepared or produced from a first tobacco product prepared from a tobacco plant, or part thereof, produced by growing the seed of tobacco cultivar CMS TND950 SRC, where first product is selected from the group consisting of pipe tobacco, cigar tobacco, cigarette tobacco, chewing tobacco, leaf tobacco, shredded tobacco, cut tobacco and any combination thereof, and the second tobacco product is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, cut tobacco, loose leaf chewing tobacco, plug chewing tobacco, moist snuff, and nasal snuff. In some aspects, the first and/or second product comprises a reduced amount of nornicotine and/or N'-nitrosonornicotine (NNN).

In an aspect, the present disclosure includes a part of a tobacco plant, produced by growing the seed of tobacco cultivar CMS TND950 SRC, where the part is selected from the group consisting of leaf, pollen, ovule, embryo, cotyledon, hypocotyl, meristematic cell, protoplast, root, root tip, pistil, anther, flower, shoot, stem, pod and petiole.

In another aspect, the present disclosure includes a tissue culture produced from a protoplast or cell from a tobacco plant, or part thereof, produced by growing the seed of tobacco cultivar CMS TND950 SRC, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole.

In an aspect, the present disclosure includes a tobacco plant regenerated from a tissue culture produced from a protoplast or cell from a tobacco plant, or part thereof, produced by growing the seed of tobacco cultivar CMS TND950 SRC, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole where the regenerated plant has all, or essentially all of the morphological and physiological characteristics of cultivar CMS TND950 SRC.

In an aspect, the present disclosure includes an $F_1$ progeny plant of tobacco cultivar CMS TND950 SRC.

In another aspect, the present disclosure includes an $F_1$ progeny plant of tobacco cultivar CMS TND950 SRC, where the $F_1$ plant is cytoplasmic male sterile (CMS).

In another aspect, the present disclosure includes an $F_1$ progeny seed produced crossing two tobacco plants and harvesting the resultant tobacco seed, where at least one tobacco plant is a tobacco plant produced by growing the seed of tobacco cultivar CMS TND950 SRC, where at least one tobacco plant is cytoplasmic male sterile (CMS).

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar CMS TND950 SRC.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar CMS TND950 SRC, where the plant of tobacco cultivar CMS TND950 SRC is the male parent.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar CMS TND950 SRC, where the plant of tobacco cultivar CMS TND950 SRC is the female parent.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar CMS TND950 SRC, where at least one tobacco plant is cytoplasmic male sterile (CMS).

In an aspect, the present disclosure also includes a container of $F_1$ progeny seeds produced by crossing two tobacco plants and harvesting the resultant tobacco seed, where at least one tobacco plant is a tobacco plant produced by growing the seed of tobacco cultivar CMS TND950 SRC, where at least one tobacco plant is cytoplasmic male sterile (CMS).

In an aspect, the present disclosure includes an $F_1$ progeny plant produced by growing a seed produced by crossing two tobacco plants and harvesting the resultant tobacco seed, where at least one tobacco plant is a tobacco plant produced by growing the seed of tobacco cultivar CMS TND950 SRC, and where at least one tobacco plant is cytoplasmic male sterile (CMS).

In an aspect, the present disclosure also includes a harvested leaf of an $F_1$ progeny plant produced by growing a seed produced by a method of comprising crossing two tobacco plants and harvesting the resultant tobacco seed, where at least one tobacco plant is a tobacco plant produced by growing the seed of tobacco cultivar CMS TND950 SRC, where at least one tobacco plant is cytoplasmic male sterile (CMS).

In another aspect, the present disclosure further includes a harvested leaf of an $F_1$ progeny plant having a reduced amount of nornicotine and/or N'-nitrosonornicotine (NNN) produced by growing a seed produced by a method of comprising crossing two tobacco plants and harvesting the resultant tobacco seed, where at least one tobacco plant is a tobacco plant produced by growing the seed of tobacco cultivar CMS TND950 SRC, where at least one tobacco plant is cytoplasmic male sterile (CMS).

In an aspect, the present disclosure also includes a harvested leaf of an $F_1$ progeny plant having a reduced amount of nornicotine and/or N'-nitrosonornicotine (NNN) in a smoke stream produced from the leaf, where the plant is produced by growing a seed produced by crossing two tobacco plants and harvesting the resultant tobacco seed, where at least one tobacco plant is a tobacco plant produced by growing the seed of tobacco cultivar CMS TND950 SRC, where at least one tobacco plant is cytoplasmic male sterile (CMS).

In an aspect, the present disclosure includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar CMS TND950 SRC, where at least one tobacco plant is cytoplasmic male sterile, and where the tobacco product is selected from the group consisting of pipe tobacco, cigar tobacco, cigarette tobacco, chewing tobacco, leaf tobacco, shredded tobacco, cut tobacco and any combination thereof.

In an aspect, the present disclosure further includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar CMS TND950 SRC, where at least one tobacco plant is cytoplasmic male sterile, and where the tobacco product is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, cut tobacco, loose leaf chewing tobacco, plug chewing tobacco, moist snuff, and nasal snuff.

In an aspect, the present disclosure further includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar CMS TND950 SRC, where at least one tobacco plant is cytoplasmic male sterile, and where the tobacco product is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, cut tobacco, loose leaf chewing tobacco, and further where the product has a reduced amount of nornicotine and/or N'-nitrosonornicotine (NNN).

In an aspect, the present disclosure includes a method for producing a tobacco seed comprising crossing two tobacco plants and harvesting the resultant tobacco seed, where at least one tobacco plant is cytoplasmic male sterile, where the cytoplasmic male sterile plant is a plant of tobacco cultivar CMS TND950 SRC.

In an aspect, the present disclosure includes a seed of tobacco cultivar CMS Narrow Leaf Madole SRC, a representative sample seed of the cultivar having been deposited with the American Type Culture Collection (ATCC) under ATCC Accession No. PTA-123661.

In another aspect, the present disclosure includes a tobacco plant, or part thereof, produced by growing the seed of tobacco cultivar CMS Narrow Leaf Madole SRC.

In a further aspect, the present disclosure includes a harvested leaf, or part thereof, of a tobacco plant, or part thereof, produced by growing the seed of tobacco cultivar CMS Narrow Leaf Madole SRC.

In an aspect, the present disclosure includes a harvested leaf, or part thereof, of a tobacco plant, produced by growing the seed of tobacco cultivar CMS Narrow Leaf Madole SRC, where the leaf has a reduced amount of nornicotine and/or N'-nitrosonornicotine (NNN).

In an aspect, the present disclosure includes a harvested leaf, or part thereof, produced by growing the seed of tobacco cultivar CMS Narrow Leaf Madole SRC, where the leaf has a reduced amount of nornicotine and/or N'-nitrosonornicotine (NNN), where the reduced amount of nornicotine and/or N'-nitrosonornicotine (NNN) is reduced in a smoke stream produced from the leaf.

In a further aspect, the present disclosure includes a tobacco product, prepared from a tobacco plant, or part thereof, produced by growing the seed of tobacco cultivar CMS Narrow Leaf Madole SRC, where the product is selected from the group consisting of pipe tobacco, cigar tobacco, cigarette tobacco, chewing tobacco, leaf tobacco, shredded tobacco, cut tobacco, and any combination thereof.

In an aspect, the present disclosure includes a tobacco product, prepared from a tobacco plant, or part thereof, produced by growing the seed of tobacco cultivar CMS Narrow Leaf Madole SRC, where the product is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, cut tobacco, loose leaf chewing tobacco, plug chewing tobacco, moist snuff, and nasal snuff.

In another aspect, the present disclosure includes a tobacco product, prepared from a tobacco plant, or part thereof, produced by growing the seed of tobacco cultivar CMS Narrow Leaf Madole SRC, where the product is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, cut tobacco, loose leaf chewing tobacco, and further where the product has a reduced amount of nornicotine and/or N'-nitrosonornicotine (NNN).

In a further aspect, the present disclosure includes a second tobacco product prepared or produced from a first tobacco product prepared from a tobacco plant, or part thereof, produced by growing the seed of tobacco cultivar CMS Narrow Leaf Madole SRC, where first product is selected from the group consisting of pipe tobacco, cigar tobacco, cigarette tobacco, chewing tobacco, leaf tobacco, shredded tobacco, cut tobacco and any combination thereof, and the second tobacco product is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, cut tobacco, loose leaf chewing tobacco, plug chewing tobacco, moist snuff, and nasal snuff. In some aspects, the first and/or second product comprises a reduced amount of nornicotine and/or N'-nitrosonornicotine (NNN).

In an aspect, the present disclosure includes a part of a tobacco plant, produced by growing the seed of tobacco cultivar CMS Narrow Leaf Madole SRC, where the part is selected from the group consisting of leaf, pollen, ovule, embryo, cotyledon, hypocotyl, meristematic cell, protoplast, root, root tip, pistil, anther, flower, shoot, stem, pod and petiole.

In another aspect, the present disclosure includes a tissue culture produced from a protoplast or cell from a tobacco plant, or part thereof, produced by growing the seed of tobacco cultivar CMS Narrow Leaf Madole SRC, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole.

In an aspect, the present disclosure includes a tobacco plant regenerated from a tissue culture produced from a protoplast or cell from a tobacco plant, or part thereof, produced by growing the seed of tobacco cultivar CMS Narrow Leaf Madole SRC, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole where the regenerated plant has all, or essentially all of the morphological and physiological characteristics of cultivar CMS Narrow Leaf Madole SRC.

In an aspect, the present disclosure includes an $F_1$ progeny plant of tobacco cultivar CMS Narrow Leaf Madole SRC.

In another aspect, the present disclosure includes an $F_1$ progeny plant of tobacco cultivar CMS Narrow Leaf Madole SRC, where the $F_1$ plant is cytoplasmic male sterile (CMS).

In another aspect, the present disclosure includes an $F_1$ progeny seed produced crossing two tobacco plants and harvesting the resultant tobacco seed, where at least one tobacco plant is a tobacco plant produced by growing the seed of tobacco cultivar CMS Narrow Leaf Madole SRC, where at least one tobacco plant is cytoplasmic male sterile (CMS).

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar CMS Narrow Leaf Madole SRC.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar CMS Narrow Leaf Madole SRC, where the plant of tobacco cultivar CMS Narrow Leaf Madole SRC is the male parent.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar CMS Narrow Leaf Madole SRC, where the plant of tobacco cultivar CMS Narrow Leaf Madole SRC is the female parent.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar CMS Narrow Leaf Madole SRC, where at least one tobacco plant is cytoplasmic male sterile (CMS).

In an aspect, the present disclosure also includes a container of $F_1$ progeny seeds produced by crossing two tobacco plants and harvesting the resultant tobacco seed, where at least one tobacco plant is a tobacco plant produced by growing the seed of tobacco cultivar CMS Narrow Leaf Madole SRC, where at least one tobacco plant is cytoplasmic male sterile (CMS).

In an aspect, the present disclosure includes an $F_1$ progeny plant produced by growing a seed produced by crossing two tobacco plants and harvesting the resultant tobacco seed, where at least one tobacco plant is a tobacco plant produced by growing the seed of tobacco cultivar CMS Narrow Leaf Madole SRC, and where at least one tobacco plant is cytoplasmic male sterile (CMS).

In an aspect, the present disclosure also includes a harvested leaf of an $F_1$ progeny plant produced by growing a seed produced by a method of comprising crossing two tobacco plants and harvesting the resultant tobacco seed, where at least one tobacco plant is a tobacco plant produced by growing the seed of tobacco cultivar CMS Narrow Leaf Madole SRC, where at least one tobacco plant is cytoplasmic male sterile (CMS).

In another aspect, the present disclosure further includes a harvested leaf of an $F_1$ progeny plant having a reduced amount of nornicotine and/or N'-nitrosonornicotine (NNN) produced by growing a seed produced by a method of comprising crossing two tobacco plants and harvesting the resultant tobacco seed, where at least one tobacco plant is a tobacco plant produced by growing the seed of tobacco cultivar CMS Narrow Leaf Madole SRC, where at least one tobacco plant is cytoplasmic male sterile (CMS).

In an aspect, the present disclosure also includes a harvested leaf of an $F_1$ progeny plant having a reduced amount of nornicotine and/or N'-nitrosonornicotine (NNN) in a smoke stream produced from the leaf, where the plant is produced by growing a seed produced by crossing two tobacco plants and harvesting the resultant tobacco seed, where at least one tobacco plant is a tobacco plant produced by growing the seed of tobacco cultivar CMS Narrow Leaf Madole SRC, where at least one tobacco plant is cytoplasmic male sterile (CMS).

In an aspect, the present disclosure includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar CMS Narrow Leaf Madole SRC, where at least one tobacco plant is cytoplasmic male sterile, and where the tobacco product is selected from the group consisting of pipe tobacco, cigar tobacco, cigarette tobacco, chewing tobacco, leaf tobacco, shredded tobacco, cut tobacco and any combination thereof.

In an aspect, the present disclosure further includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar CMS Narrow Leaf Madole SRC, where at least one tobacco plant is cytoplasmic male sterile, and where the tobacco product is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, cut tobacco, loose leaf chewing tobacco, plug chewing tobacco, moist snuff, and nasal snuff.

In an aspect, the present disclosure further includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar CMS Narrow Leaf Madole SRC, where at least one tobacco plant is cytoplasmic male sterile, and where the tobacco product is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, cut tobacco, loose leaf chewing tobacco, and further where the product has a reduced amount of nornicotine and/or N'-nitrosonornicotine (NNN).

In an aspect, the present disclosure includes a method for producing a tobacco seed comprising crossing two tobacco plants and harvesting the resultant tobacco seed, where at least one tobacco plant is cytoplasmic male sterile, where the cytoplasmic male sterile plant is a plant of tobacco cultivar CMS Narrow Leaf Madole SRC.

In an aspect, the present disclosure includes a seed of tobacco cultivar CMS KY171 SRC, a representative sample seed of the cultivar having been deposited with the American Type Culture Collection (ATCC) under ATCC Accession No. PTA-123660.

In another aspect, the present disclosure includes a tobacco plant, or part thereof, produced by growing the seed of tobacco cultivar CMS KY171 SRC.

In a further aspect, the present disclosure includes a harvested leaf, or part thereof, of a tobacco plant, or part thereof, produced by growing the seed of tobacco cultivar CMS KY171 SRC.

In an aspect, the present disclosure includes a harvested leaf, or part thereof, of a tobacco plant, produced by growing the seed of tobacco cultivar CMS KY171 SRC, where the leaf has a reduced amount of nornicotine and/or N'-nitrosonornicotine (NNN).

In an aspect, the present disclosure includes a harvested leaf, or part thereof, produced by growing the seed of tobacco cultivar CMS KY171 SRC, where the leaf has a reduced amount of nornicotine and/or N'-nitrosonornicotine (NNN), where the reduced amount of nornicotine and/or N'-nitrosonornicotine (NNN) is reduced in a smoke stream produced from the leaf.

In a further aspect, the present disclosure includes a tobacco product, prepared from a tobacco plant, or part thereof, produced by growing the seed of tobacco cultivar CMS KY171 SRC, where the product is selected from the group consisting of pipe tobacco, cigar tobacco, cigarette tobacco, chewing tobacco, leaf tobacco, shredded tobacco, cut tobacco, and any combination thereof.

In an aspect, the present disclosure includes a tobacco product, prepared from a tobacco plant, or part thereof, produced by growing the seed of tobacco cultivar CMS KY171 SRC, where the product is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, cut tobacco, loose leaf chewing tobacco, plug chewing tobacco, moist snuff, and nasal snuff.

In another aspect, the present disclosure includes a tobacco product, prepared from a tobacco plant, or part thereof, produced by growing the seed of tobacco cultivar CMS KY171 SRC, where the product is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, cut tobacco, loose leaf chewing tobacco, and where the product has a reduced amount of nornicotine and/or N'-nitrosonornicotine (NNN).

In a further aspect, the present disclosure includes a second tobacco product prepared or produced from a first tobacco product prepared from a tobacco plant, or part thereof, produced by growing the seed of tobacco cultivar CMS KY171 SRC, where first product is selected from the group consisting of pipe tobacco, cigar tobacco, cigarette tobacco, chewing tobacco, leaf tobacco, shredded tobacco, cut tobacco and any combination thereof, and the second tobacco product is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, cut tobacco, loose leaf chewing tobacco, plug chewing tobacco, moist snuff, and nasal snuff. In some aspects, the first and/or second product comprises a reduced amount of nornicotine and/or N'-nitrosonornicotine (NNN).

In an aspect, the present disclosure includes a part of a tobacco plant, produced by growing the seed of tobacco cultivar CMS KY171 SRC, where the part is selected from the group consisting of leaf, pollen, ovule, embryo, cotyledon, hypocotyl, meristematic cell, protoplast, root, root tip, pistil, anther, flower, shoot, stem, pod and petiole.

In another aspect, the present disclosure includes a tissue culture produced from a protoplast or cell from a tobacco plant, or part thereof, produced by growing the seed of tobacco cultivar CMS KY171 SRC, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole.

In an aspect, the present disclosure includes a tobacco plant regenerated from a tissue culture produced from a protoplast or cell from a tobacco plant, or part thereof, produced by growing the seed of tobacco cultivar CMS KY171 SRC, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole where the regenerated plant has all, or essentially all of the morphological and physiological characteristics of cultivar CMS KY171 SRC.

In an aspect, the present disclosure includes an $F_1$ progeny plant of tobacco cultivar CMS KY171 SRC.

In another aspect, the present disclosure includes an $F_1$ progeny plant of tobacco cultivar CMS KY171 SRC, where the $F_1$ plant is cytoplasmic male sterile (CMS).

In another aspect, the present disclosure includes an $F_1$ progeny seed produced crossing two tobacco plants and harvesting the resultant tobacco seed, where at least one tobacco plant is a tobacco plant produced by growing the seed of tobacco cultivar CMS KY171 SRC, where at least one tobacco plant is cytoplasmic male sterile (CMS).

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar CMS KY171 SRC.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar CMS KY171 SRC, where the plant of tobacco cultivar CMS KY171 SRC is the male parent.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar CMS KY171 SRC, where the plant of tobacco cultivar CMS KY171 SRC is the female parent.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar CMS KY171 SRC, where at least one tobacco plant is cytoplasmic male sterile (CMS).

In an aspect, the present disclosure also includes a container of $F_1$ progeny seeds produced by crossing two tobacco plants and harvesting the resultant tobacco seed, where at least one tobacco plant is a tobacco plant produced by growing the seed of tobacco cultivar CMS KY171 SRC, where at least one tobacco plant is cytoplasmic male sterile (CMS).

In an aspect, the present disclosure includes an $F_1$ progeny plant produced by growing a seed produced by crossing two tobacco plants and harvesting the resultant tobacco seed, where at least one tobacco plant is a tobacco plant produced by growing the seed of tobacco cultivar CMS KY171 SRC, and where at least one tobacco plant is cytoplasmic male sterile (CMS).

In an aspect, the present disclosure also includes a harvested leaf of an $F_1$ progeny plant produced by growing a seed produced by a method of comprising crossing two tobacco plants and harvesting the resultant tobacco seed, where at least one tobacco plant is a tobacco plant produced by growing the seed of tobacco cultivar CMS KY171 SRC, where at least one tobacco plant is cytoplasmic male sterile (CMS).

In another aspect, the present disclosure further includes a harvested leaf of an $F_1$ progeny plant having a reduced amount of nornicotine and/or N'-nitrosonornicotine (NNN) produced by growing a seed produced by a method of comprising crossing two tobacco plants and harvesting the resultant tobacco seed, where at least one tobacco plant is a tobacco plant produced by growing the seed of tobacco cultivar CMS KY171 SRC, where at least one tobacco plant is cytoplasmic male sterile (CMS).

In an aspect, the present disclosure also includes a harvested leaf of an $F_1$ progeny plant having a reduced amount of nornicotine and/or N'-nitrosonornicotine (NNN) in a smoke stream produced from the leaf, where the plant is produced by growing a seed produced by crossing two tobacco plants and harvesting the resultant tobacco seed, where at least one tobacco plant is a tobacco plant produced by growing the seed of tobacco cultivar CMS KY171 SRC, where at least one tobacco plant is cytoplasmic male sterile (CMS).

In an aspect, the present disclosure includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar CMS KY171 SRC, where at least one tobacco plant is cytoplasmic male sterile, and where the tobacco product is selected from the group consisting of pipe tobacco, cigar tobacco, cigarette tobacco, chewing tobacco, leaf tobacco, shredded tobacco, cut tobacco and any combination thereof.

In an aspect, the present disclosure further includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar CMS KY171 SRC, where at least one tobacco plant is cytoplasmic male sterile, and where the tobacco product is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, cut tobacco, loose leaf chewing tobacco, plug chewing tobacco, moist snuff, and nasal snuff.

In an aspect, the present disclosure further includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar CMS KY171 SRC, where at least one tobacco plant is cytoplasmic male sterile, and where the tobacco product is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, cut tobacco, loose leaf chewing tobacco, and further where the product has a reduced amount of nornicotine and/or N'-nitrosonornicotine (NNN).

In an aspect, the present disclosure includes a method for producing a tobacco seed comprising crossing two tobacco plants and harvesting the resultant tobacco seed, where at least one tobacco plant is cytoplasmic male sterile, where the cytoplasmic male sterile plant is a plant of tobacco cultivar CMS KY171 SRC.

In another aspect, the present disclosure includes seed of hybrid tobacco cultivars PD7305 SRC, PD7309 SRC, PD7312 SRC, PD7318 SRC, and PD7319 SRC. Seeds of hybrid cultivar PD7305 SRC are obtainable by crossing CMS TND950 SRC dark tobacco with pollen of TND950 (phph) SRC dark tobacco. Seeds of hybrid cultivar PD7309 SRC are obtainable by crossing CMS Narrow Leaf Madole SRC dark tobacco with pollen of Narrow Leaf Madole (phph) SRC dark tobacco. Seeds of hybrid cultivar PD7312 SRC are obtainable by crossing CMS KY171 SRC dark tobacco with pollen of Narrow Leaf Madole SRC dark tobacco. Seeds of hybrid cultivar PD7318 SRC are obtainable by crossing CMS KY171 SRC dark tobacco with pollen of Narrow Leaf Madole (phph) SRC dark tobacco. Seeds of hybrid cultivar PD7319 SRC are obtainable by crossing CMS TND950 SRC dark tobacco with pollen of Narrow Leaf Madole (phph) SRC dark tobacco, and collecting the seeds.

In an aspect, the present disclosure includes a tobacco plant, or part thereof, produced by growing a seed of hybrid tobacco cultivar PD7305 SRC, PD7309 SRC, PD7312 SRC, PD7318 SRC, or PD7319 SRC.

In a further aspect, the present disclosure includes a harvested leaf, or part thereof, of a tobacco plant produced by growing the seed of hybrid tobacco cultivar PD7305 SRC, PD7309 SRC, PD7312 SRC, PD7318 SRC, or PD7319 SRC.

In another aspect, the present disclosure includes a harvested leaf, or part thereof, of a tobacco plant, produced by growing the seed of hybrid tobacco cultivar PD7305 SRC, PD7309 SRC, PD7312 SRC, PD7318 SRC, or PD7319 SRC, where the leaf has a reduced amount of nornicotine and/or N'-nitrosonornicotine (NNN).

In an aspect, the present disclosure includes a harvested leaf, or part thereof, produced by growing the seed of hybrid tobacco cultivar PD7305 SRC, PD7309 SRC, PD7312 SRC, PD7318 SRC, or PD7319 SRC, where the leaf has a reduced amount of nornicotine and/or N'-nitrosonornicotine (NNN), where the reduced amount of nornicotine and/or N'-nitrosonornicotine (NNN) is reduced in a smoke stream produced from the leaf.

In a further aspect, the present disclosure includes a tobacco product, prepared from a tobacco plant, or part thereof, produced by growing the seed of hybrid tobacco cultivar PD7305 SRC, PD7309 SRC, PD7312 SRC, PD7318 SRC, or PD7319 SRC, where the product is selected from the group consisting of pipe tobacco, cigar tobacco, cigarette tobacco, chewing tobacco, leaf tobacco, shredded tobacco, cut tobacco, and any combination thereof.

In an aspect, the present disclosure includes a tobacco product, prepared from a tobacco plant, or part thereof, produced by growing the seed of hybrid tobacco cultivar PD7305 SRC, PD7309 SRC, PD7312 SRC, PD7318 SRC, or PD7319 SRC, where the product is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, cut tobacco, loose leaf chewing tobacco, plug chewing tobacco, moist snuff, and nasal snuff.

In another aspect, the present disclosure includes a tobacco product, prepared from a tobacco plant, or part thereof, produced by growing the seed of hybrid tobacco cultivar PD7305 SRC, PD7309 SRC, PD7312 SRC, PD7318 SRC, or PD7319 SRC, where the product is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, cut tobacco, loose leaf chewing tobacco, and further where the product has a reduced amount of nornicotine and/or N'-nitrosonornicotine (NNN).

In a further aspect, the present disclosure includes a second tobacco product prepared or produced from a first tobacco product prepared from a tobacco plant, or part thereof, produced by growing the seed of tobacco cultivar PD7305 SRC, PD7309 SRC, PD7312 SRC, PD7318 SRC, or PD7319 SRC, where the first tobacco product is selected from the group consisting of pipe tobacco, cigar tobacco, cigarette tobacco, chewing tobacco, leaf tobacco, shredded tobacco, cut tobacco and any combination thereof, and the second tobacco product is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, cut tobacco, loose leaf chewing tobacco, plug chewing tobacco, moist snuff, and nasal snuff. In some aspects, the first and/or second product comprises a reduced amount of nornicotine and/or N'-nitrosonornicotine (NNN).

In an aspect, the present disclosure includes a part of a tobacco plant, produced by growing a seed of hybrid tobacco cultivar PD7305 SRC, PD7309 SRC, PD7312 SRC, PD7318 SRC, or PD7319 SRC, where the part is selected from the group consisting of leaf, pollen, ovule, embryo, cotyledon, hypocotyl, meristematic cell, protoplast, root, root tip, pistil, anther, flower, shoot, stem, pod, and petiole.

In a further aspect, the present disclosure includes a tissue culture produced from a protoplast or cell from a tobacco plant, or part thereof, produced by growing the seed of hybrid tobacco cultivar PD7305 SRC, PD7309 SRC, PD7312 SRC, PD7318 SRC, or PD7319 SRC, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole.

In an aspect, the present disclosure includes a tobacco plant regenerated from a tissue culture produced from a protoplast or cell from a tobacco plant, or part thereof, produced by growing the seed of hybrid tobacco cultivar PD7305 SRC, PD7309 SRC, PD7312 SRC, PD7318 SRC, or PD7319 SRC, where the cell or protoplast of the tissue culture can be produced from a plant part selected from the group consisting of a leaf, pollen, embryo, cotyledon, hypocotyl, meristematic cell, root, root tip, pistil, anther, flower, shoot, stem, pod, and petiole, where the regenerated plant has all, or essentially all, of the morphological and physiological characteristics of hybrid cultivar PD7305 SRC, PD7309 SRC, PD7312 SRC, PD7318 SRC, or PD7319 SRC.

In an aspect, the present disclosure includes an $F_1$ progeny plant of hybrid tobacco cultivar PD7305 SRC, PD7309 SRC, PD7312 SRC, PD7318 SRC, or PD7319 SRC.

In an aspect, the present disclosure includes an $F_1$ progeny plant of hybrid tobacco cultivar PD7305 SRC or PD7319 SRC, where the plant of tobacco cultivar CMS TND950 SRC is the female parent.

In an aspect, the present disclosure includes an $F_1$ progeny plant of hybrid tobacco cultivar PD7309 SRC, where the plant of tobacco cultivar CMS Narrow Leaf Madole SRC is the female parent.

In an aspect, the present disclosure includes an $F_1$ progeny plant of hybrid tobacco cultivar PD7312 SRC or PD7318 SRC, where the plant of tobacco cultivar CMS KY171 SRC is the female parent.

In an aspect, the present disclosure includes an $F_1$ progeny plant of hybrid tobacco cultivar PD7305 SRC, where the plant of tobacco cultivar CMS TND950 SRC is the male parent.

In an aspect, the present disclosure includes an $F_1$ progeny plant of hybrid tobacco cultivar PD7309 SRC, PD7318 SRC, or PD7319 SRC where the plant of tobacco cultivar Narrow Leaf Madole (phph) SRC is the male parent.

In an aspect, the present disclosure includes an $F_1$ progeny plant of hybrid tobacco cultivar PD7312 SRC, where the plant of tobacco cultivar Narrow Leaf Madole SRC is the male parent.

In another aspect, the present disclosure includes an $F_1$ progeny plant of hybrid tobacco cultivar PD7305 SRC, PD7309 SRC, PD7312 SRC, PD7318 SRC, or PD7319 SRC where the $F_1$ plant is cytoplasmic male sterile (CMS).

In another aspect, the present disclosure includes a method for producing a tobacco seed of PD7305 SRC or PD7319 SRC comprising crossing two tobacco plants and harvesting the resultant tobacco seed, where one tobacco plant is a tobacco plant produced by growing the seed of tobacco cultivar CMS TND950 SRC.

In another aspect, the present disclosure includes a method for producing a tobacco seed of PD7309 SRC comprising crossing two tobacco plants and harvesting the resultant tobacco seed, where one tobacco plant is a tobacco plant produced by growing the seed of tobacco cultivar CMS Narrow Leaf Madole SRC.

In another aspect, the present disclosure includes a method for producing a tobacco seed of PD7312 SRC or PD7318 SRC comprising crossing two tobacco plants and harvesting the resultant tobacco seed, where one tobacco plant is a tobacco plant produced by growing the seed of tobacco cultivar CMS KY171 SRC.

In an aspect, the present disclosure includes a method of vegetatively propagating a plant of a tobacco cultivar comprising the steps of (a) collecting tissue capable of being propagated from a plant of a tobacco cultivar selected from the group consisting of TND950 (phph) SRC, Narrow Leaf Madole (phph) SRC, Narrow Leaf Madole SRC, CMS TND950 SRC, CMS Narrow Leaf Madole SRC, and CMS KY171 SRC, (b) cultivating the tissue to obtain a proliferated shoot; and (c) rooting the proliferated shoots to obtain a rooted plantlet.

In an aspect, the present disclosure includes a method of vegetatively propagating a plant of a tobacco cultivar comprising the steps of (a) collecting tissue capable of being propagated from a plant of a tobacco cultivar selected from the group consisting of TND950 (phph) SRC, Narrow Leaf Madole (phph) SRC, Narrow Leaf Madole SRC, CMS TND950 SRC, CMS Narrow Leaf Madole SRC, and CMS KY171 SRC; (b) cultivating the tissue to obtain a proliferated shoot; (c) rooting the proliferated shoots to obtain a rooted plantlet; and (d) growing a plant from the rooted plantlet.

In an aspect, the present disclosure includes a method of introducing a desired trait into a tobacco cultivar comprising: (a) crossing a plant of a first tobacco cultivar selected from the group consisting of TND950 (phph) SRC, Narrow Leaf Madole (phph) SRC, Narrow Leaf Madole SRC, CMS TND950 SRC, CMS Narrow Leaf Madole SRC, and CMS KY171 SRC, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of said first tobacco cultivar to produce a backcross $BC_1F_1$ progeny seed; (d) growing the $BC_1F_1$ progeny seed and selecting a backcross $BC_1F_1$ progeny plant comprising the desired trait and essentially all of the physiological and morphological characteristics of said first tobacco cultivar, TND950 (phph) SRC, Narrow Leaf Madole (phph) SRC, Narrow Leaf Madole SRC, CMS TND950 SRC, CMS Narrow Leaf Madole SRC, or CMS KY171 SRC; and e) repeating steps (c) and (d) three or more times (e.g., 3, 4, 5, 6, 7, 8, 9, 10, and the like) in succession to produce selected fourth or higher backcross progeny that comprise the desired trait. In additional aspects, steps (c) and (d) can be repeated one or more times (e.g., 1, 2, 3, 4, 5, 6, 7, 8, 9, 10, and the like) in succession to produce second or higher backcross progeny comprising the desired trait.

In an aspect, the present disclosure includes a method of introducing a desired trait into a tobacco cultivar comprising: (a) crossing a plant of a first tobacco cultivar selected from the group consisting of TND950 (phph) SRC, Narrow Leaf Madole (phph) SRC, Narrow Leaf Madole SRC, CMS TND950 SRC, CMS Narrow Leaf Madole SRC, and CMS KY171 SRC, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of said first tobacco cultivar to produce a backcross $BC_1F_1$ progeny seed; (d) growing the $BC_1F_1$ progeny seed and selecting a backcross $BC_1F_1$ progeny plant comprising the desired trait and essentially all of the physiological and morphological characteristics of the first tobacco cultivar, TND950 (phph) SRC, Narrow Leaf Madole (phph) SRC, Narrow Leaf Madole SRC, CMS TND950 SRC, CMS Narrow Leaf Madole SRC, or CMS KY171 SRC; and (e) repeating steps (c) and (d) three or more times in succession to produce selected fourth or higher backcross progeny that comprise the desired trait, where the trait is cytoplasmic male sterility (CMS). In additional aspects, steps (c) and (d) can be repeated one or more times in succession to produce second or higher backcross progeny comprising the desired trait, where the trait is CMS.

In an aspect, the present disclosure includes a method of introducing a desired trait into a tobacco cultivar comprising: (a) crossing a plant of a first tobacco cultivar selected from the group consisting of TND950 (phph) SRC, Narrow Leaf Madole (phph) SRC, Narrow Leaf Madole SRC, CMS TND950 SRC, CMS Narrow Leaf Madole SRC, and CMS KY171 SRC, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of the first tobacco cultivar selected from the group consisting of TND950 (phph) SRC, Narrow Leaf Madole (phph) SRC, and Narrow Leaf Madole SRC, to produce a backcross $BC_1F_1$ progeny seed; (d) growing the $BC_1F_1$ progeny seed and selecting a backcross $BC_1F_1$ progeny plant comprising the desired trait and the physiological and essentially all of morphological characteristics of the first tobacco cultivar TND950 (phph) SRC, Narrow Leaf Madole (phph) SRC, or Narrow Leaf Madole SRC; and (e) repeating steps (c) and (d) three or more times in succession to produce selected fourth or higher backcross progeny that comprise the desired trait, where the trait is cytoplasmic male sterility (CMS) and the CMS trait is obtained from the cytoplasm of *Nicotiana suaveolens* or *Nicotiana glauca*. In additional aspects, steps (c) and (d) can be repeated one or more times in succession to produce second or higher backcross progeny comprising the desired trait, where the trait is CMS and the CMS trait is obtained from the cytoplasm of *Nicotiana suaveolens* or *Nicotiana glauca*.

In an aspect, the present disclosure includes a method of introducing a desired trait into a tobacco cultivar comprising: (a) crossing a plant of a first tobacco cultivar selected from the group TND950 (phph) SRC, Narrow Leaf Madole (phph) SRC, and Narrow Leaf Madole SRC with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of said first tobacco cultivar to produce a backcross $BC_1F_1$ progeny seed; (d) growing the $BC_1F_1$ progeny seed and selecting a backcross $BC_1F_1$ progeny plant comprising the desired trait and essentially all of the physiological and morphological characteristics of the first tobacco cultivar TND950 (phph) SRC, Narrow Leaf Madole (phph) SRC, or Narrow Leaf Madole SRC; and (e) repeating steps (c) and (d) three or more times in succession to produce selected fourth or higher backcross progeny that comprise the desired trait, where the trait is cytoplasmic male sterility (CMS) and the CMS trait is obtained from the cytoplasm of *Nicotiana suaveolens*, and where the second tobacco plant is selected from the group consisting of CMS TND950 SRC, CMS Narrow Leaf Madole SRC, or CMS KY171 SRC. In additional aspects, steps (c) and (d) can be repeated one or more times in succession to produce second or higher backcross progeny comprising the CMS trait obtained from the cytoplasm of *Nicotiana suaveolens*, and where the second tobacco plant is selected from the group consisting of CMS TND950 SRC, CMS Narrow Leaf Madole SRC, and CMS KY171 SRC.

In an aspect, the present disclosure includes a tobacco plant produced by a method comprising introducing a desired trait into a tobacco cultivar comprising: (a) crossing a plant of a first tobacco cultivar selected from the group consisting of TND950 (phph) SRC, Narrow Leaf Madole (phph) SRC, Narrow Leaf Madole SRC, CMS TND950 SRC, CMS Narrow Leaf Madole SRC, and CMS KY171 SRC, with a second tobacco plant that comprises a desired trait to produce an $F_1$ progeny seed; (b) growing the $F_1$ progeny seed and selecting an F$_1$ progeny plant that comprises the desired trait; (c) crossing the selected F$_1$ progeny plant with a plant of said first tobacco cultivar to produce a backcross BC$_1$F$_1$ progeny seed; (d) growing the BC$_1$F$_1$ progeny seed and selecting a backcross BC$_1$F$_1$ progeny plant comprising the desired trait and essentially all of the physiological and morphological characteristics of the first tobacco cultivar TND950 (phph) SRC, Narrow Leaf Madole (phph) SRC, Narrow Leaf Madole SRC, CMS TND950 SRC, CMS Narrow Leaf Madole SRC, or CMS KY171 SRC; and (e) repeating steps (c) and (d) three or more times in succession to produce selected fourth or higher backcross progeny that comprise the desired trait. In additional aspects, steps (c) and (d) can be repeated one or more times in succession to produce second or higher backcross progeny comprising the desired trait.

In another aspect, the present disclosure includes a method of introducing a desired trait into a tobacco cultivar comprising: (a) crossing a plant of a first tobacco cultivar selected from the group consisting of TND950 (phph) SRC, Narrow Leaf Madole (phph) SRC, Narrow Leaf Madole SRC, CMS TND950 SRC, CMS Narrow Leaf Madole SRC, and CMS KY171 SRC, with a plant of a second tobacco cultivar that comprises a desired trait to produce a progeny plant where the desired trait is selected from the group consisting of herbicide resistance, pest resistance, disease resistance, high yield, high grade index, curability, curing quality, mechanical harvestability, holding ability, leaf quality, height, plant maturation, early maturing, early to medium maturing, medium maturing, medium to late maturing, late maturing, small stalk, medium stalk, large stalk, leaf number per plant, 5-10 leaves per plant, 11-15 leaves per plant, 16-21 leaves per plant, and any combination thereof, to produce an F$_1$ progeny seed; (b) growing the F$_1$ progeny seed into an F$_1$ progeny plant and selecting the F$_1$ progeny plant having the desired trait; (c) crossing the selected F$_1$ progeny plant with a plant of said first tobacco cultivar, to produce a backcross progeny plant seed; (d) growing the backcross progeny plant seed into a backcross progeny plant and selecting the backcross progeny plant comprising the desired trait and essentially all of the physiological and morphological characteristics of the first tobacco cultivar, TND950 (phph) SRC, Narrow Leaf Madole (phph) SRC, Narrow Leaf Madole SRC, CMS TND950 SRC, CMS Narrow Leaf Madole SRC, or CMS KY171 SRC; and (e) repeating steps (c) and (d) one or more times in succession to produce a selected second, third, fourth or higher backcross progeny plant that comprises the desired trait and essentially all of the physiological and morphological characteristics of the first tobacco cultivar, TND950 (phph) SRC, Narrow Leaf Madole (phph) SRC, Narrow Leaf Madole SRC, CMS TND950 SRC, CMS Narrow Leaf Madole SRC, or CMS KY171 SRC.

In another aspect, the present disclosure includes a method of introducing a desired trait into a tobacco cultivar comprising: (a) crossing a plant of a first tobacco cultivar selected from the group consisting of TND950 (phph) SRC, Narrow Leaf Madole (phph) SRC, Narrow Leaf Madole SRC, CMS TND950 SRC, CMS Narrow Leaf Madole SRC, and CMS KY171 SRC, with a plant of a second tobacco cultivar that comprises a desired trait to produce a progeny plant where the desired trait is selected from the group consisting of herbicide resistance, pest resistance, disease resistance, high yield, high grade index, curability, curing quality, mechanical harvestability, holding ability, leaf quality, height, plant maturation, early maturing, early to medium maturing, medium maturing, medium to late maturing, late maturing, small stalk, medium stalk, large stalk, leaf number per plant, 5-10 leaves per plant, 11-15 leaves per plant, 16-21 leaves per plant, and any combination thereof, to produce an F$_1$ progeny seed; (b) growing the F$_1$ progeny seed into an F$_1$ progeny plant and selecting the F$_1$ progeny plant having the desired trait; (c) crossing the selected F$_1$ progeny plant with a plant of said first tobacco cultivar to produce a backcross progeny plant seed; (d) growing the backcross progeny plant seed into a backcross progeny plant and selecting the backcross progeny plant comprising the desired trait and essentially all of the physiological and morphological characteristics of said first tobacco cultivar, TND950 (phph) SRC, Narrow Leaf Madole (phph) SRC, Narrow Leaf Madole SRC, CMS TND950 SRC, CMS Narrow Leaf Madole SRC, or CMS KY171 SRC; and (e) repeating steps (c) and (d) one or more times in succession to produce a selected second, third, fourth or higher backcross progeny plant that comprises the desired trait and essentially all of the physiological and morphological characteristics of the first tobacco cultivar, TND950 (phph) SRC, Narrow Leaf Madole (phph) SRC, Narrow Leaf Madole SRC, CMS TND950 SRC, CMS Narrow Leaf Madole SRC, or CMS KY171 SRC.

In another aspect, the present disclosure includes a method of introducing a desired trait into a tobacco cultivar comprising: (a) crossing a plant of a first tobacco cultivar selected from the group consisting of TND950 (phph) SRC, Narrow Leaf Madole (phph) SRC, Narrow Leaf Madole SRC, CMS TND950 SRC, CMS Narrow Leaf Madole SRC, and CMS KY171 SRC, with a plant of a second tobacco cultivar that comprises a desired trait to produce a progeny plant where the desired trait is selected from the group consisting of herbicide resistance, pest resistance, disease resistance, high yield, high grade index, curability, curing quality, mechanical harvestability, holding ability, leaf quality, height, plant maturation, early maturing, early to medium maturing, medium maturing, medium to late maturing, late maturing, small stalk, medium stalk, large stalk, leaf number per plant, 5-10 leaves per plant, 11-15 leaves per plant, 16-21 leaves per plant, and any combination thereof, to produce an F$_1$ progeny seed; (b) growing the F$_1$ progeny seed into an F$_1$ progeny plant and selecting the F$_1$ progeny plant having the desired trait; (c) crossing the selected F$_1$ progeny plant with a plant of said first tobacco cultivar to produce a backcross progeny plant seed; (d) growing the backcross progeny plant seed into a backcross progeny plant and selecting the backcross progeny plant comprising the desired trait and essentially all of the physiological and morphological characteristics of the first tobacco cultivar, TND950 (phph) SRC, Narrow Leaf Madole (phph) SRC, Narrow Leaf Madole SRC, CMS TND950 SRC, CMS Narrow Leaf Madole SRC, or CMS KY171 SRC; and (e) repeating steps (c) and (d) one or more times in succession to produce a selected second, third, fourth or higher backcross progeny plant that comprises the desired trait and essentially all of the physiological and morphological characteristics of said first tobacco cultivar, TND950 (phph) SRC, Narrow Leaf Madole (phph) SRC, Narrow Leaf Madole SRC, CMS TND950 SRC, CMS Narrow Leaf Madole SRC, or CMS KY171 SRC, where the desired trait is disease resistance.

In another aspect, the present disclosure includes a method for producing a tobacco plant having decreased nicotine conversion comprising: identifying a first tobacco plant comprising a nucleotide sequence selected from the group consisting of the nucleotide sequence of SEQ ID NO: 1, SEQ ID NO: 2, SEQ ID NO: 11, and any combination thereof; crossing the first tobacco plant with a second tobacco plant and collecting an $F_1$ seed; crossing a plant grown from the $F_1$ seed to a third tobacco plant and collecting a second tobacco seed; and identifying a second tobacco seed or a plant grown from the second seed that is homozygous for the nucleotide sequence selected from the group consisting of the nucleotide sequence of SEQ ID NO: 1, SEQ ID NO: 2, SEQ ID NO: 11, and any combination thereof.

In an aspect, the present disclosure includes a method for producing a tobacco plant having decreased nicotine conversion comprising: identifying a first tobacco plant comprising a nucleotide sequence selected from the group consisting of the nucleotide sequence of SEQ ID NO: 1, SEQ ID NO: 2, SEQ ID NO: 11, and any combination thereof; crossing the first tobacco plant with a second tobacco plant and collecting an $F_1$ seed; crossing a plant grown from the $F_1$ seed to a third tobacco plant and collecting a second tobacco seed; and identifying a second tobacco seed or a plant grown from the second seed that is homozygous for the nucleotide sequence selected from the group consisting of the nucleotide sequence of SEQ ID NO: 1, SEQ ID NO: 2, SEQ ID NO: 11, and any combination thereof, where the second tobacco plant comprises a nucleotide sequence selected from the group consisting of the nucleotide sequence of SEQ ID NO: 1, SEQ ID NO: 2, SEQ ID NO: 11, and any combination thereof.

In an aspect, the present disclosure includes a method for producing a tobacco plant having decreased nicotine conversion comprising: identifying a first tobacco plant comprising a nucleotide sequence selected from the group consisting of the nucleotide sequence of SEQ ID NO: 1, SEQ ID NO: 2, SEQ ID NO: 11, and any combination thereof; crossing the first tobacco plant with a second tobacco plant and collecting an $F_1$ seed; crossing a plant grown from the $F_1$ seed to a third tobacco plant and collecting a second tobacco seed; and identifying a second tobacco seed or a plant grown from the second seed that is homozygous for the nucleotide sequence selected from the group consisting of the nucleotide sequence of SEQ ID NO: 1, SEQ ID NO: 2, SEQ ID NO: 11, and any combination thereof, where the second tobacco plant does not have the nucleotide sequence selected from the group consisting of the nucleotide sequence of SEQ ID NO: 1, SEQ ID NO: 2, SEQ ID NO: 11, and any combination thereof, and the third tobacco plant is a tobacco plant comprising a nucleotide sequence selected from the group consisting of the nucleotide sequence of SEQ ID NO: 1, SEQ ID NO: 2, SEQ ID NO: 11, and any combination thereof.

In an aspect, the present disclosure includes a method for producing a tobacco plant having decreased nicotine conversion comprising: identifying a first tobacco plant comprising a nucleotide sequence selected from the group consisting of the nucleotide sequence of SEQ ID NO: 1, SEQ ID NO: 2, SEQ ID NO: 11, and any combination thereof; crossing the first tobacco plant with a second tobacco plant and collecting an $F_1$ seed; crossing a plant grown from the $F_1$ seed to a third tobacco plant and collecting a second tobacco seed; and identifying a second tobacco seed or a plant grown from the second seed that is homozygous for the nucleotide sequence selected from the group consisting of the nucleotide sequence of SEQ ID NO: 1, SEQ ID NO: 2, SEQ ID NO: 11, and any combination thereof, where the first tobacco plant comprises the sequence set forth in SEQ ID NO: 1 or SEQ ID NO: 2.

In an aspect, the present disclosure includes a method for producing a tobacco plant having decreased nicotine conversion comprising: identifying a first tobacco plant comprising a nucleotide sequence selected from the group consisting of the nucleotide sequence of SEQ ID NO: 1, SEQ ID NO: 2, SEQ ID NO: 11, and any combination thereof; crossing the first tobacco plant with a second tobacco plant and collecting an $F_1$ seed; crossing a plant grown from the $F_1$ seed to a third tobacco plant and collecting a second tobacco seed; and identifying a second tobacco seed or a plant grown from the second seed that is homozygous for the nucleotide sequence selected from the group consisting of the nucleotide sequence of SEQ ID NO: 1, SEQ ID NO: 2, SEQ ID NO: 11, and any combination thereof, where the third tobacco plant is a tobacco plant comprising a nucleotide sequence selected from the group consisting of the nucleotide sequence of SEQ ID NO: 1, SEQ ID NO: 2, SEQ ID NO: 11, and any combination thereof.

In an aspect, the present disclosure includes a method for producing a tobacco plant having decreased nicotine conversion comprising: identifying a first tobacco plant comprising a nucleotide sequence selected from the group consisting of the nucleotide sequence of SEQ ID NO: 1, SEQ ID NO: 2, SEQ ID NO: 11, and any combination thereof; crossing the first tobacco plant with a second tobacco plant and collecting an $F_1$ seed; crossing a plant grown from the $F_1$ seed to a third tobacco plant and collecting a second tobacco seed; and identifying a second tobacco seed or a plant grown from the second seed that is homozygous for the nucleotide sequence selected from the group consisting of the nucleotide sequence of SEQ ID NO: 1, SEQ ID NO: 2, SEQ ID NO: 11, and any combination thereof, where the first tobacco plant is a plant of a tobacco cultivar TND950 (phph) SRC, Narrow Leaf Madole (phph) SRC, Narrow Leaf Madole SRC, CMS TND950 SRC, CMS Narrow Leaf Madole SRC, or CMS KY171 SRC and hybrid cultivars PD7305 SRC, PD7309 SRC, PD7312 SRC, PD7318 SRC, or PD7319 SRC.

In an aspect, the present disclosure includes a method for producing a tobacco plant having decreased nicotine conversion comprising: identifying a first tobacco plant comprising a nucleotide sequence selected from the group consisting of the nucleotide sequence of SEQ ID NO: 1, SEQ ID NO: 2, SEQ ID NO: 11, and any combination thereof; crossing the first tobacco plant with a second tobacco plant and collecting an $F_1$ seed; crossing a plant grown from the $F_1$ seed to a third tobacco plant and collecting a second tobacco seed; and identifying a second tobacco seed or a plant grown from the second seed that is homozygous for the nucleotide sequence selected from the group consisting of the nucleotide sequence of SEQ ID NO: 1, SEQ ID NO: 2, SEQ ID NO: 11, and any combination thereof, where the third tobacco plant is a plant of tobacco cultivar TND950 (phph) SRC, Narrow Leaf Madole (phph) SRC, Narrow Leaf Madole SRC, CMS TND950 SRC, CMS Narrow Leaf Madole SRC, or CMS KY171 SRC and hybrid cultivars PD7305 SRC, PD7309 SRC, PD7312 SRC, PD7318 SRC, or PD7319 SRC.

In another aspect, the present disclosure includes a method of producing a plant of a tobacco cultivar selected from the group consisting of TND950 (phph) SRC, Narrow Leaf Madole (phph) SRC, Narrow Leaf Madole SRC, CMS TND950 SRC, CMS Narrow Leaf Madole SRC, and CMS KY171 SRC, and hybrid cultivars PD7305 SRC, PD7309 SRC, PD7312 SRC, PD7318 SRC, and PD7319 SRC comprising at least one (e.g., 1, 2, 3, 4, 5, 6, 7, 8, and the like) additional desired trait comprising the steps of: (a) collecting tissue capable of being propagated from a plant of a tobacco cultivar selected from the group consisting of TND950

(phph) SRC, Narrow Leaf Madole (phph) SRC, Narrow Leaf Madole SRC, CMS TND950 SRC, CMS Narrow Leaf Madole SRC, and CMS KY171 SRC, and hybrid cultivars PD7305 SRC, PD7309 SRC, PD7312 SRC, PD7318 SRC, and PD7319 SRC; and (b) introducing a transgene (nucleic acid construct) conferring at least one desired trait into the tissue.

In another aspect, the present disclosure includes a method of producing an herbicide resistant tobacco plant comprising transforming a tobacco plant, or part thereof, produced by growing a seed of a tobacco cultivar selected from the group consisting of tobacco cultivar TND950 (phph) SRC, Narrow Leaf Madole (phph) SRC, Narrow Leaf Madole SRC, CMS TND950 SRC, CMS Narrow Leaf Madole SRC, and CMS KY171 SRC, and hybrid cultivars PD7305 SRC, PD7309 SRC, PD7312 SRC, PD7318 SRC, and PD7319 SRC with at least one transgene (nucleic acid construct), where the at least one transgene (nucleic acid construct) confers resistance to an herbicide selected from the group consisting of imidazolinone, cyclohexanedione, sulfonylurea, glyphosate, glufosinate, phenoxy proprionic acid, L-phosphinothricin, triazine, benzonitrile and any combination thereof.

In another aspect, the present disclosure includes an herbicide resistant tobacco plant produced by a method comprising transforming a tobacco plant, or part thereof, produced by growing a seed of a tobacco cultivar selected from the group consisting of tobacco cultivar TND950 (phph) SRC, Narrow Leaf Madole (phph) SRC, Narrow Leaf Madole SRC, CMS TND950 SRC, CMS Narrow Leaf Madole SRC, and CMS KY171 SRC, and hybrid cultivars PD7305 SRC, PD7309 SRC, PD7312 SRC, PD7318 SRC, and PD7319 SRC, with at least one transgene (nucleic acid construct), where the at least one transgene (nucleic acid construct) confers resistance to an herbicide selected from the group consisting of imidazolinone, cyclohexanedione, sulfonylurea, glyphosate, glufosinate, phenoxy proprionic acid, L-phosphinothricin, triazine, benzonitrile, and any combination thereof.

In another aspect, the present disclosure includes a method of producing a pest and/or insect resistant tobacco plant where the method comprises transforming a tobacco plant produced by growing a seed of a tobacco cultivar selected from the group consisting of TND950 (phph) SRC, Narrow Leaf Madole (phph) SRC, Narrow Leaf Madole SRC, CMS TND950 SRC, CMS Narrow Leaf Madole SRC, and CMS KY171 SRC, and hybrid cultivars PD7305 SRC, PD7309 SRC, PD7312 SRC, PD7318 SRC, and PD7319 SRC, with at least one transgene (nucleic acid construct) that confers pest and/or insect resistance.

In a further aspect, the present disclosure includes a pest and/or insect resistant tobacco plant produced by a method comprising transforming a tobacco plant produced by growing a seed of a tobacco cultivar selected from the group consisting of TND950 (phph) SRC, Narrow Leaf Madole (phph) SRC, Narrow Leaf Madole SRC, CMS TND950 SRC, CMS Narrow Leaf Madole SRC, and CMS KY171 SRC, and hybrid cultivars PD7305 SRC, PD7309 SRC, PD7312 SRC, PD7318 SRC, and PD7319 SRC with at least one transgene (nucleic acid construct) that confers pest and/or insect resistance.

In a further aspect, the present disclosure includes a pest and/or insect resistant tobacco plant produced by a method comprising transforming a tobacco plant produced by growing a seed of a tobacco cultivar selected from the group consisting of TND950 (phph) SRC, Narrow Leaf Madole (phph) SRC, Narrow Leaf Madole SRC, CMS TND950 SRC, CMS Narrow Leaf Madole SRC, and CMS KY171 SRC, and hybrid cultivars PD7305 SRC, PD7309 SRC, PD7312 SRC, PD7318 SRC, and PD7319 SRC, with at least one transgene (nucleic acid construct) that confers pest and/or insect resistance, where the transgene (nucleic acid construct) encodes a *Bacillus thuringiensis* (BT) endotoxin.

In another aspect, the present disclosure includes a method of producing a disease resistant tobacco plant, the method comprising transforming a tobacco plant produced by growing a seed of a tobacco cultivar selected from the group consisting of TND950 (phph) SRC, Narrow Leaf Madole (phph) SRC, Narrow Leaf Madole SRC, CMS TND950 SRC, CMS Narrow Leaf Madole SRC, and CMS KY171 SRC, and hybrid cultivars PD7305 SRC, PD7309 SRC, PD7312 SRC, PD7318 SRC, and PD7319 SRC with at least one transgene (nucleic acid construct) that confers disease resistance.

In a further aspect, the present disclosure includes a disease resistant tobacco plant produced by transforming a tobacco plant produced by growing a seed of a tobacco cultivar selected from the group consisting of TND950 (phph) SRC, Narrow Leaf Madole (phph) SRC, Narrow Leaf Madole SRC, CMS TND950 SRC, CMS Narrow Leaf Madole SRC, and CMS KY171 SRC, and hybrid cultivars PD7305 SRC, PD7309 SRC, PD7312 SRC, PD7318 SRC, and PD7319 SRC with at least one transgene (nucleic acid construct) that confers disease resistance.

BRIEF DESCRIPTION OF THE SEQUENCES

SEQ ID NO: 1 sets forth a cyp82e4 W329Stop nucleotide sequence.
SEQ ID NO: 2 sets forth a cyp82e5v2 W422Stop nucleotide sequence.
SEQ ID NO: 3 sets forth a cyp82e4 W329Stop amino acid sequence.
SEQ ID NO: 4 sets forth a cyp82e5v2 W422Stop amino acid sequence.
SEQ ID NO: 5 sets forth a CYP82E4 wild-type nucleotide sequence.
SEQ ID NO: 6 sets forth a CYP82E5v2 wild-type nucleotide sequence.
SEQ ID NO: 7 sets forth a CYP82E4 wild-type amino acid sequence.
SEQ ID NO: 8 sets forth a CYP82E5v2 wild-type amino acid sequence.
SEQ ID NO: 9 sets forth a CYP82E10 wild-type nucleotide sequence.
SEQ ID NO: 10 sets forth a CYP82E10 wild-type amino acid sequence.
SEQ ID NO: 11 sets forth a CYP82E10 P381S nucleotide sequence.
SEQ ID NO: 12 sets forth a CYP82E10 P381S amino acid sequence.

All three tobacco Nicotine Demethylase genes (CYP82E4, CYP82E5v2, CYP82E10) share a common structure: a 939 bp exon 1 and a 612 bp exon 2 separated by a large intron, whose length varies among the three genes. See Lewis et al., "Three nicotine demethylase genes mediate nornicotine biosynthesis in *Nicotiana tabacum* L.: Functional characterization of the CYP82E10 gene," *Phytochemistry*, 71 (2010), 1988-1998. SEQ ID NOs: 1, 2, 5, 6, 9, and 11 set forth wild-type or mutant versions of coding sequences of CYP82E4, CYP82E5v2, and CYP82E10. It is understood that, used herein, a plant comprising, having, or homozygous for a sequence selected from SEQ ID NOs: 1, 2, 5, 6, 9, and 11 refers to a plant comprising at the CYP82E4, CYP82E5v2, or CYP82E10 endogenous locus a genomic sequence comprising the coding sequence of SEQ ID NO: 1, 2, 5, 6, 9, or 11.

BRIEF DESCRIPTION OF THE FIGURES

FIG. 8 depicts the total TSNA amounts, in parts per million, detected in blended dark tobacco used for smokeless products prototypes at three stages of the production process: the dry flour blending stage, the out of cure stage, and the finished product.

FIG. 9 depicts the NNN amounts, in parts per million, detected in blended dark tobacco used for smokeless products prototypes at three stages of the production process: the dry flour blending stage, the out of cure stage, and the finished product.

DETAILED DESCRIPTION OF THE DISCLOSURE

Figure 1:
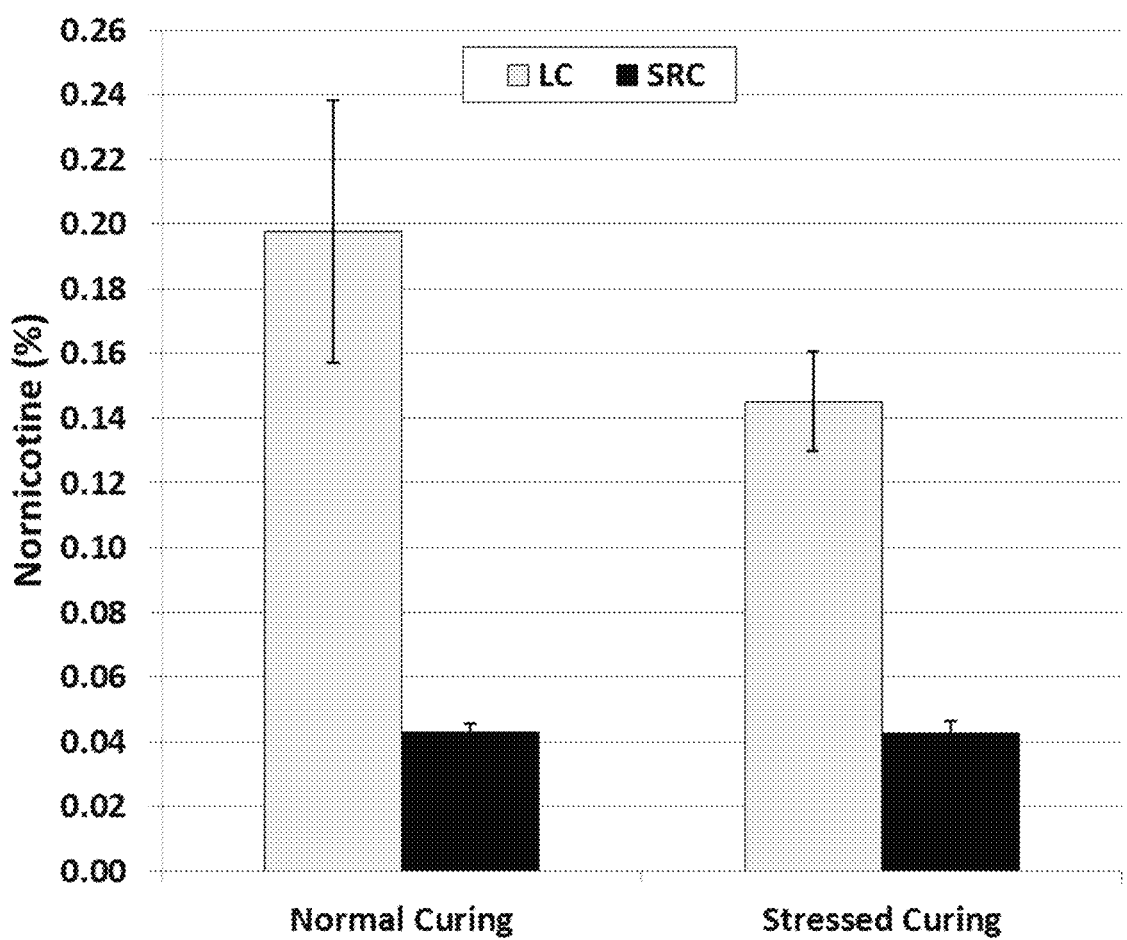
FIG. 1 depicts the amount of nornicotine, as a percentage of total alkaloids, found in LC varieties compared to the same varieties comprising SRC technology when grown and cured under normal conditions as compared to growth under normal conditions and curing under high-temperature stressed curing conditions.

This description is not intended to be a detailed catalog of all the different ways in which the disclosure may be implemented, or all the features that may be added to the instant disclosure. For example, features illustrated with respect to one embodiment may be incorporated into other embodiments, and features illustrated with respect to a particular embodiment may be deleted from that embodiment. Thus, the disclosure contemplates that in some embodiments of the disclosure, any feature or combination of features set forth herein can be excluded or omitted. In addition, numerous variations and additions to the various embodiments suggested herein will be apparent to those skilled in the art in light of the instant disclosure, which do not depart from the instant disclosure. Hence, the following descriptions are intended to illustrate some particular embodiments of the disclosure, and not to exhaustively specify all permutations, combinations and variations thereof.

Unless otherwise defined, all technical and scientific terms used herein have the same meaning as commonly understood by one of ordinary skill in the art to which this disclosure belongs. The terminology used in the description of the disclosure herein is for the purpose of describing particular embodiments only and is not intended to be limiting of the disclosure.

All publications, patent applications, patents and other references cited herein are incorporated by reference in their entireties for the teachings relevant to the sentence and/or paragraph in which the reference is presented. References to techniques employed herein are intended to refer to the techniques as commonly understood in the art, including variations on those techniques or substitutions of equivalent techniques that would be apparent to one of skill in the art.

Unless the context indicates otherwise, it is specifically intended that the various features of the disclosure described herein can be used in any combination. Moreover, the present disclosure also contemplates that in some embodiments of the disclosure, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the disclosure and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like, is meant to encompass variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The terms "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed disclosure. Thus, the term "consisting essentially of" when used in a claim of this disclosure is not intended to be interpreted to be equivalent to "comprising."

"Introducing," in the context of a polynucleotide sequence (e.g., a recombinant polynucleotide and/or expression cassette of the disclosure), means presenting a polynucleotide sequence to the plant, plant part, and/or plant cell in such a manner that the polynucleotide sequence gains access to the interior of a cell. Where more than one polynucleotide sequence is to be introduced these polynucleotide sequences can be assembled as part of a single polynucleotide or nucleic acid construct, or as separate polynucleotide or nucleic acid constructs, and can be located on the same or different transformation vectors. Accordingly, these polynucleotides can be introduced into plant cells in a single transformation event, in separate transformation events, or, e.g., as part of a breeding protocol. Thus, the term "transformation" as used herein refers to the introduction of a heterologous nucleic acid into a cell. Transformation of a cell may be stable or transient. Thus, in some embodiments, a plant cell, plant part or plant of this disclosure can be stably transformed with a recombinant polynucleotide of the disclosure. In other embodiments, a plant cell, plant part or plant of this disclosure can be transiently transformed with a recombinant polynucleotide of the disclosure.

"Tobacco product" is defined as "any product made or derived from tobacco that is intended for human use or consumption, including any component, part, or accessory of a tobacco product (except for raw materials other than tobacco used in manufacturing a component, part, or accessory of a tobacco product)" (section 201 of the FD&C Act; 21 U.S.C. 321).

Terms "nicotine conversion rate," "percent nicotine conversion," and "percentage nicotine conversion" are used interchangeably. Percent nicotine demethylation in a sample is calculated by dividing the level of nornicotine by the combined level of nicotine and nornicotine as measured in the sample, and multiplying by 100.

PD7305 SRC

In some aspects, the present disclosure provides tobacco cultivars, and parts thereof, from PD7305 SRC. In other aspects, the present disclosure provides a tobacco plant, or part thereof, produced by growing a seed of PD7305 SRC. In further aspects, a plant of the present disclosure can include a plant with all, or essentially all, of the morphological and physiological characteristics of cultivar PD7305 SRC.

While not being limited by process, PD7305 SRC is produced by pollinating plants of CMS TND950 SRC dark tobacco with pollen of TND950 (phph)SRC dark tobacco. The original tobacco cultivar PD7305 LC is a hybrid generated by pollinating plants of a male-sterile breeding line CMS TND950 with pollen produced by fertile breeding line TND950 (phph). TND950 SRC dark tobacco and TND950 (phph) SRC dark tobacco are created through the introduction of three mutated CYP82E genes into the male-sterile breeding line CMS TND950 and the fertile breeding line TND950 (phph). The three genes are a mutated CYP82E4 gene recited as 325-6 #775 in Lewis et al. ("Three nicotine demethylase genes mediate nornicotine biosynthesis in *Nicotiana tabacum* L.: Functional characterization of the CYP82E10 gene," *Phytochemistry*, 71 (2010), 1988-1998 (SEQ ID NO: 1, which sets forth a cyp82e4 W329Stop, hereby incorporated by reference in its entirety)), a mutated CYP82E5v2 recited in Lewis et al. (supra) as 325-6 #1-13 (SEQ ID NO: 2, which sets forth a cyp82e5v2 W422Stop, hereby incorporated by reference in its entirety), and a mutated CYP82E10 recited in Lewis et al. (supra) as 325-6 #1041 (SEQ ID NO:11, which sets forth a cyp82e10 P381S, hereby incorporated by reference in its entirety). Mutations cyp82e4 W329Stop and cyp82e5v2 W422Stop result in truncated proteins while cyp82E10 P381S results in a non-functional protein. A cyp82e4 W329Stop ("e4"), a cyp82e5v2 W422Stop ("e5"), and a cyp82e10 P381S ("e10") mutation are introduced from a e4e4|e5e5|e10e10 triple mutant from a strong converter burley background, line DH98-325-6, as listed in Table 4 of Lewis et al. (supra) into both the male-sterile breeding line CMS TND950 and a fertile breeding line TND950 (phph) dark tobacco.

TND950 SRC dark tobacco and TND950 (phph) SRC dark tobacco are the result of seven backcrosses with TND950 or TND950 (phph) as the recurrent parents, followed by two rounds of selfing with selection for homozygosity for the cyp82e4 W329Stop, the cyp82e5v2 W422Stop, and cyp82e10 P381S mutations to yield BC$_7$F$_3$ plants (TND950 SRC and TND950 (phph) SRC) in which the wild-type CYP82E4, CYP82E5v2 and CYP82E10 alleles of KY171 and TND950 (phph) are replaced by the mutant alleles (e.g., cyp82e4 W329Stop, cyp82e5v2 W422Stop, and cyp82e10 P381S).

To develop CMS TND950 SRC dark tobacco, a plant of CMS TND950 was crossed with TND950 SRC dark tobacco to produce male-sterile plants heterozygous for all three mutations. A single male-sterile plant resulting from this cross was then subsequently backcrossed as a female to TND950 SRC dark tobacco to produce progeny that were segregating for individuals homozygous for all three mutations. Triple homozygous individuals were identified by DNA genotyping to produce the CMS TND950 SRC dark tobacco line. Because the line is male-sterile, it is maintained via pollination with TND950 SRC dark tobacco. PD7305 SRC dark tobacco hybrid is produced by pollinating plants of CMS TND950 SRC dark tobacco with pollen of TND950 (phph) SRC dark tobacco.

CMS TND950 SRC dark tobacco, TND950 (phph) SRC dark tobacco, and PD7305 SRC dark tobacco progeny plants have genetic backgrounds that are at least 95%, at least 97%, at least 98%, or at least 99% similar to CMS TND950, TND950 (phph), and PD7305 LC respectively. PD7305 SRC plants exhibit low nornicotine levels and produce leaves with reduced potential for accumulating derived NNN during curing, storage, and smoking.

PD7309 SRC

In some aspects, the present disclosure provides tobacco cultivars, and parts thereof, from PD7309 SRC. In other aspects, the present disclosure provides a tobacco plant, or part thereof, produced by growing a seed of PD7309 SRC. In further aspects, a plant of the present disclosure can include a plant with all, or essentially all, of the morphological and physiological characteristics of cultivar PD7309 SRC.

While not being limited by process, PD7309 SRC is produced by pollinating plants of CMS Narrow Leaf Madole SRC dark tobacco with pollen of Narrow Leaf Madole (phph) SRC dark tobacco. The original tobacco cultivar PD7309 LC is a hybrid generated by pollinating plants of a male-sterile breeding line CMS Narrow Leaf Madole with pollen produced by fertile breeding line Narrow Leaf Madole (phph). Narrow Leaf Madole SRC dark tobacco and Narrow Leaf Madole (phph) SRC dark tobacco are created through the introduction of three mutated CYP82E genes into the male-sterile breeding line CMS Narrow Leaf Madole and the fertile breeding line Narrow Leaf Madole (phph). The three genes are a mutated CYP82E4 gene recited as 325-6 #775 in Lewis et al. ("Three nicotine demethylase genes mediate nornicotine biosynthesis in *Nicotiana tabacum* L.: Functional characterization of the CYP82E10 gene," *Phytochemistry*, 71 (2010), 1988-1998 (SEQ ID NO: 1, which sets forth a cyp82e4 W329Stop, hereby incorporated by reference in its entirety)), a mutated CYP82E5v2 recited in Lewis et al. (supra) as 325-6 #1-13

(SEQ ID NO: 2, which sets forth a cyp82e5v2 W422Stop, hereby incorporated by reference in its entirety), and a mutated CYP82E10 recited in Lewis et al. (supra) as 325-6 #1041 (SEQ ID NO:11, which sets forth a cyp82e10 P381S, hereby incorporated by reference in its entirety). Mutations cyp82e4 W329Stop and cyp82e5v2 W422Stop result in truncated proteins while cyp82E10 P381S results in a non-functional protein. A cyp82e4 W329Stop ("e4"), a cyp82e5v2 W422Stop ("e5"), and a cyp82e10 P381S ("e10") mutation are introduced from a e4e4|e5e5|e10e10 triple mutant from a strong converter burley background, line DH98-325-6, as listed in Table 4 of Lewis et al. (supra) into both the male-sterile breeding line CMS Narrow Leaf Madole and a fertile breeding line Narrow Leaf Madole (phph) dark tobacco.

Narrow Leaf Madole SRC dark tobacco and Narrow Leaf Madole (phph) SRC dark tobacco are the result of seven backcrosses with Narrow Leaf Madole or Narrow Leaf Madole (phph) as the recurrent parents, followed by two rounds of selfing with selection for homozygosity for the cyp82e4 W329Stop, the cyp82e5v2 W422Stop, and cyp82e10 P381S mutations to yield $BC_7F_3$ plants (Narrow Leaf Madole SRC and Narrow Leaf Madole (phph) SRC) in which the wild-type CYP82E4, CYP82E5v2 and CYP82E10 alleles of Narrow Leaf Madole and Narrow Leaf Madole (phph) are replaced by the mutant alleles (e.g., cyp82e4 W329Stop, cyp82e5v2 W422 Stop, and cyp82e10 P381S).

To develop CMS Narrow Leaf Madole SRC dark tobacco, a plant of CMS Narrow Leaf Madole was crossed with Narrow Leaf Madole SRC dark tobacco to produce male-sterile plants heterozygous for all three mutations. A single male-sterile plant resulting from this cross was then subsequently backcrossed as a female to Narrow Leaf Madole SRC dark tobacco to produce progeny that were segregating for individuals homozygous for all three mutations. Triple homozygous individuals were identified by DNA genotyping to produce the CMS Narrow Leaf Madole SRC dark tobacco line. Because the line is male-sterile, it is maintained via pollination with Narrow Leaf Madole SRC dark tobacco. PD7309 SRC dark tobacco hybrid is produced by pollinating plants of CMS Narrow Leaf Madole SRC dark tobacco with pollen of Narrow Leaf Madole (phph) SRC dark tobacco.

CMS Narrow Leaf Madole SRC dark tobacco, Narrow Leaf Madole (phph) SRC dark tobacco, and PD7309 SRC dark tobacco progeny plants have genetic backgrounds that are at least 95%, at least 97%, at least 98%, or at least 99% similar to CMS Narrow Leaf Madole, Narrow Leaf Madole (phph), and PD7309 LC respectively. PD7309 SRC plants exhibit low nornicotine levels and produce leaves with reduced potential for accumulating derived NNN during curing, storage, and smoking.

PD7312 SRC

In some aspects, the present disclosure provides tobacco cultivars, and parts thereof, from PD7312 SRC. In other aspects, the present disclosure provides a tobacco plant, or part thereof, produced by growing a seed of PD7312 SRC. In further aspects, a plant of the present disclosure can include a plant with all, or essentially all, of the morphological and physiological characteristics of cultivar PD7312 SRC.

While not being limited by process, PD7312 SRC is produced by pollinating plants of CMS KY171 SRC dark tobacco with pollen of Narrow Leaf Madole SRC dark tobacco. The original tobacco cultivar PD7312 LC is a hybrid generated by pollinating plants of a male-sterile breeding line CMS KY171 with pollen by fertile breeding line Narrow Leaf Madole. KY171 SRC dark tobacco and Narrow Leaf Madole SRC dark tobacco are created through the introduction of three mutated CYP82E genes into the male-sterile breeding line CMS KY171 and the fertile breeding line Narrow Leaf Madole. The three genes are a mutated CYP82E4 gene recited as 325-6 #775 in Lewis et al. ("Three nicotine demethylase genes mediate nornicotine biosynthesis in *Nicotiana tabacum* L.: Functional characterization of the CYP82E10 gene," *Phytochemistry*, 71 (2010), 1988-1998 (SEQ ID NO: 1, which sets forth a cyp82e4 W329Stop, hereby incorporated by reference in its entirety)), a mutated CYP82E5v2 recited in Lewis et al. (supra) as 325-6 #1-13 (SEQ ID NO: 2, which sets forth a cyp82e5v2 W422Stop, hereby incorporated by reference in its entirety), and a mutated CYP82E10 recited in Lewis et al. (supra) as 325-6 #1041 (SEQ ID NO:11, which sets forth a cyp82e10 P381S, hereby incorporated by reference in its entirety). Mutations cyp82e4 W329Stop and cyp82e5v2 W422Stop result in truncated proteins while cyp82E10 P381S results in a nonfunctional protein. A cyp82e4 W329Stop ("e4"), a cyp82e5v2 W422Stop ("e5"), and a cyp82e10 P381S ("e10") mutation are introduced from a e4e4|e5e5|e10e10 triple mutant from a strong converter burley background, line DH98-325-6, as listed in Table 4 of Lewis et al. (supra) into both the male-sterile breeding line CMS KY171 and a fertile breeding line Narrow Leaf Madole dark tobacco.

KY171 SRC dark tobacco and Narrow Leaf Madole SRC dark tobacco are the result of seven backcrosses with KY171 or Narrow Leaf Madole as the recurrent parents, followed by two rounds of selfing with selection for homozygosity for the cyp82e4 W329Stop, the cyp82e5v2 W422Stop, and cyp82e10 P381S mutations to yield $BC_7F_3$ plants (KY171 SRC and Narrow Leaf Madole SRC) in which the wild-type CYP82E4, CYP82E5v2 and CYP82E10 alleles of KY171 and Narrow Leaf Madole are replaced by the mutant alleles (e.g., cyp82e4 W329Stop, cyp82e5v2 W422Stop, and cyp82e10 P381S).

To develop CMS KY171 SRC dark tobacco, a plant of CMS KY171 was crossed with KY171 SRC dark tobacco to produce male-sterile plants heterozygous for all three mutations. A single male-sterile plant resulting from this cross was then subsequently backcrossed as a female to KY171 SRC dark tobacco to produce progeny that were segregating for individuals homozygous for all three mutations. Triple homozygous individuals were identified by DNA genotyping to produce the CMS KY171 SRC dark tobacco line. Because the line is male-sterile, it is maintained via pollination with KY171 SRC dark tobacco. PD7312 SRC dark tobacco hybrid is produced by pollinating plants of CMS KY171 SRC dark tobacco with pollen of Narrow Leaf Madole SRC dark tobacco.

CMS KY171 SRC dark tobacco, Narrow Leaf Madole SRC dark tobacco, and PD7312 SRC dark tobacco progeny plants have genetic backgrounds that are at least 95%, at least 97%, at least 98%, or at least 99% similar to CMS KY171, Narrow Leaf Madole, and PD7312 LC respectively. PD7312 SRC plants exhibit low nornicotine levels and produce leaves with reduced potential for accumulating derived NNN during curing, storage, and smoking.

PD7318 SRC

In some aspects, the present disclosure provides tobacco cultivars, and parts thereof, from PD7318 SRC. In other aspects, the present disclosure provides a tobacco plant, or part thereof, produced by growing a seed of PD7318 SRC. In further aspects, a plant of the present disclosure can include a plant with all, or essentially all, of the morphological and physiological characteristics of cultivar PD7318 SRC.

While not being limited by process, PD7318 SRC is produced by pollinating plants of CMS KY171 SRC dark tobacco with pollen of Narrow Leaf Madole (phph) SRC dark tobacco. The original tobacco cultivar PD7318 LC is a hybrid generated by pollinating plants of a male-sterile breeding line CMS KY171 with pollen produced by fertile breeding line Narrow Leaf Madole (phph). KY171 SRC dark tobacco and Narrow Leaf Madole (phph) SRC dark tobacco are created through the introduction of three mutated CYP82E genes into the male-sterile breeding line CMS KY171 and the fertile breeding line Narrow Leaf Madole (phph). The three genes are a mutated CYP82E4 gene recited as 325-6 #775 in Lewis et al. ("Three nicotine demethylase genes mediate nornicotine biosynthesis in *Nicotiana tabacum* L.: Functional characterization of the CYP82E10 gene," *Phytochemistry*, 71 (2010), 1988-1998 (SEQ ID NO: 1, which sets forth a cyp82e4 W329Stop, hereby incorporated by reference in its entirety)), a mutated CYP82E5v2 recited in Lewis et al. (supra) as 325-6 #1-13 (SEQ ID NO: 2, which sets forth a cyp82e5v2 W422Stop, hereby incorporated by reference in its entirety), and a mutated CYP82E10 recited in Lewis et al. (supra) as 325-6 #1041 (SEQ ID NO:11, which sets forth a cyp82e10 P381S, hereby incorporated by reference in its entirety). Mutations cyp82e4 W329Stop and cyp82e5v2 W422Stop result in truncated proteins while cyp82E10 P381S results in a non-functional protein. A cyp82e4 W329Stop ("e4"), a cyp82e5v2 W422Stop ("e5"), and a cyp82e10 P381S ("e10") mutation are introduced from a e4e4|e5e5|e10e10 triple mutant from a strong converter burley background, line DH98-325-6, as listed in Table 4 of Lewis et al. (supra) into both the male-sterile breeding line CMS KY171 and a fertile breeding line Narrow Leaf Madole (phph) dark tobacco.

KY171 SRC dark tobacco and Narrow Leaf Madole (phph) SRC dark tobacco are the result of seven backcrosses with KY171 or Narrow Leaf Madole (phph) as the recurrent parents, followed by two rounds of selfing with selection for homozygosity for the cyp82e4 W329Stop, the cyp82e5v2 W422Stop, and cyp82e10 P381S mutations to yield $BC_7F_3$ plants (KY171 SRC and Narrow Leaf Madole (phph) SRC) in which the wild-type CYP82E4, CYP82E5v2 and CYP82E10 alleles of KY171 and Narrow Leaf Madole (phph) are replaced by the mutant alleles (e.g., cyp82e4 W329Stop, cyp82e5v2 W422Stop, and cyp82e10 P381S).

To develop CMS KY171 SRC dark tobacco, a plant of CMS KY171 was crossed with KY171 SRC dark tobacco to produce male-sterile plants heterozygous for all three mutations. A single male-sterile plant resulting from this cross was then subsequently backcrossed as a female to KY171 SRC dark tobacco to produce progeny that were segregating for individuals homozygous for all three mutations. Triple homozygous individuals were identified by DNA genotyping to produce the CMS KY171 SRC dark tobacco line. Because the line is male-sterile, it is maintained via pollination with KY171 SRC dark tobacco. The PD7318 SRC dark tobacco hybrid is produced by pollinating plants of CMS KY171 SRC dark tobacco with pollen of Narrow Leaf Madole (phph) SRC dark tobacco CMS KY171 SRC dark tobacco, Narrow Leaf Madole (phph) SRC dark tobacco, and PD7318 SRC dark tobacco progeny plants have genetic backgrounds that are at least 95%, at least 97%, at least 98%, or at least 99% similar to CMS KY171, Narrow Leaf Madole (phph), and PD7318 LC respectively. PD7318 SRC plants exhibit low nornicotine levels and produce leaves with reduced potential for accumulating derived NNN during curing, storage, and smoking.

PD7319 SRC

In some aspects, the present disclosure provides tobacco cultivars, and parts thereof, from PD7319 SRC. In other aspects, the present disclosure provides a tobacco plant, or part thereof, produced by growing a seed of PD7319 SRC. In further aspects, a plant of the present disclosure can include a plant with all, or essentially all, of the morphological and physiological characteristics of cultivar PD7319 SRC.

While not being limited by process, PD7319 SRC is produced by pollinating plants of CMS TND950 SRC dark tobacco with pollen of Narrow Leaf Madole (phph) SRC dark tobacco. The original tobacco cultivar PD7319 LC is a hybrid generated by pollinating plants of a male-sterile breeding line CMS TND950 with pollen produced by fertile breeding line Narrow Leaf Madole (phph). TND950 SRC dark tobacco and Narrow Leaf Madole (phph) SRC dark tobacco are created through the introduction of three mutated CYP82E genes into the male-sterile breeding line CMS TND950 and the fertile breeding line Narrow Leaf Madole (phph). The three genes are a mutated CYP82E4 gene recited as 325-6 #775 in Lewis et al. ("Three nicotine demethylase genes mediate nornicotine biosynthesis in *Nicotiana tabacum* L.: Functional characterization of the CYP82E10 gene," *Phytochemistry*, 71 (2010), 1988-1998 (SEQ ID NO: 1, which sets forth a cyp82e4 W329Stop, hereby incorporated by reference in its entirety)), a mutated CYP82E5v2 recited in Lewis et al. (supra) as 325-6 #1-13 (SEQ ID NO: 2, which sets forth a cyp82e5v2 W422Stop, hereby incorporated by reference in its entirety), and a mutated CYP82E10 recited in Lewis et al. (supra) as 325-6 #1041 (SEQ ID NO:11, which sets forth a cyp82e10 P381S, hereby incorporated by reference in its entirety). Mutations cyp82e4 W329Stop and cyp82e5v2 W422Stop result in truncated proteins while cyp82E10 P381S results in a non-functional protein. A cyp82e4 W329Stop ("e4"), a cyp82e5v2 W422Stop ("e5"), and a cyp82e10 P381S ("e10") mutation are introduced from a e4e4|e5e5|e10e10 triple mutant from a strong converter burley background, line DH98-325-6, as listed in Table 4 of Lewis et al. (supra) into both the male-sterile breeding line CMS TND950 and a fertile breeding line Narrow Leaf Madole (phph) dark tobacco.

TND950 SRC dark tobacco and Narrow Leaf Madole (phph) SRC dark tobacco are the result of seven backcrosses with TND950 or Narrow Leaf Madole (phph) as the recurrent parents, followed by two rounds of selfing with selection for homozygosity for the cyp82e4 W329Stop, the cyp82e5v2 W422Stop, and cyp82e10 P381S mutations to yield $BC_7F_3$ plants (TND950 SRC and Narrow Leaf Madole (phph) SRC) in which the wild-type CYP82E4, CYP82E5v2 and CYP82E10 alleles of KY171 and Narrow Leaf Madole (phph) are replaced by the mutant alleles (e.g., cyp82e4 W329Stop, cyp82e5v2 W422Stop, and cyp82e10 P381S).

To develop CMS TND950 SRC dark tobacco, a plant of CMS TND950 was crossed with TND950 SRC dark tobacco to produce male-sterile plants heterozygous for all three mutations. A single male-sterile plant resulting from this cross was then subsequently backcrossed as a female to TND950 SRC dark tobacco to produce progeny that were segregating for individuals homozygous for all three mutations. Triple homozygous individuals were identified by DNA genotyping to produce the CMS TND950 SRC dark tobacco line. Because the line is male-sterile, it is maintained via pollination with TND950 SRC dark tobacco. The PD7319 SRC dark tobacco hybrid is produced by pollinating plants of CMS TND950 SRC dark tobacco with pollen of Narrow Leaf Madole (phph) SRC dark tobacco.

CMS TND950 SRC dark tobacco, Narrow Leaf Madole (phph) SRC dark tobacco, and PD7319 SRC dark tobacco progeny plants have genetic backgrounds that are at least 95%, at least 97%, at least 98%, or at least 99% similar to CMS TND950, Narrow Leaf Madole (phph), and PD7319 LC respectively. PD7319 SRC plants exhibit low nornicotine levels and produce leaves with reduced potential for accumulating derived NNN during curing, storage, and smoking.

Other Plants

In some aspects, the present disclosure provides a tobacco seed produced by crossing two parent tobacco plants and harvesting the resultant tobacco seed, where at least one parent tobacco plant is TND950 (phph) SRC, Narrow Leaf Madole (phph) SRC, Narrow Leaf Madole SRC, CMS TND950 SRC, CMS Narrow Leaf Madole SRC, or CMS KY171 SRC. In one aspect, the TND950 (phph) SRC, Narrow Leaf Madole (phph) SRC, or Narrow Leaf Madole SRC is the male parent plant. In another aspect, the CMS TND950 SRC, CMS Narrow Leaf Madole SRC, or CMS KY171 SRC is the female parent plant. One aspect of the present disclosure provides tobacco plants that are homozygous at the cyp82e4, cyp82e5v2, and cyp82E10 loci for SEQ ID NO: 1, SEQ ID NO: 2, and SEQ ID NO: 11, respectively, and which share a genetic background that is greater than about 75%, 80%, 85%, 90%, 95%, 98%, or 99% similar to TND950 (phph) SRC, Narrow Leaf Madole (phph) SRC, Narrow Leaf Madole SRC, CMS TND950 SRC, CMS Narrow Leaf Madole SRC, or CMS KY171 SRC. In one aspect, approximately or greater than about 50%, 75%, or 100% of a progeny's genetics is provided by a plant of the present disclosure that is homozygous at the cyp82e4, cyp82e5v2, and cyp82E10 loci for SEQ ID NO: 1, SEQ ID NO: 2, and SEQ ID NO: 11, respectively. In one aspect, a plant of the present disclosure has a genetic background that is at least 95%, at least 97%, at least 98%, or at least 99% similar to TND950 (phph) SRC, Narrow Leaf Madole (phph) SRC, Narrow Leaf Madole SRC, CMS TND950 SRC, CMS Narrow Leaf Madole SRC, or CMS KY171 SRC. In another aspect, a plant of the present disclosure exhibits low nornicotine and is not subject to conversion to high nornicotine. In one aspect, a plant of the present disclosure is the progeny plant of a female or male parent plant that is *Fusarium* wilt resistant. In another aspect, a plant of TND950 (phph) SRC, Narrow Leaf Madole (phph) SRC, Narrow Leaf Madole SRC has low resistance to black shank and moderate resistance to bacterial wilt.

The present disclosure includes a tobacco seed produced by crossing two parent tobacco plants and harvesting the resultant tobacco seed, where at least one parent tobacco plant is TND950 (phph) SRC, Narrow Leaf Madole (phph) SRC, or Narrow Leaf Madole SRC. In one aspect, the TND950 (phph) SRC, Narrow Leaf Madole (phph) SRC, Narrow Leaf Madole SRC is the male parent plant. In another aspect, the CMS TND950 SRC, CMS Narrow Leaf Madole SRC, or CMS KY171 SRC is the female parent plant. One aspect of the present disclosure provides tobacco plants that are homozygous at the cyp82e4, cyp82e5v2, and cyp82E10 loci for SEQ ID NO: 1, SEQ ID NO: 2, and SEQ ID NO: 11, respectively, and which share a genetic background that is greater than about 75%, 80%, 85%, 90%, 95%, 98%, or 99% similar to TND950 (phph) SRC, Narrow Leaf Madole (phph) SRC, Narrow Leaf Madole SRC, CMS TND950 SRC, CMS Narrow Leaf Madole SRC, or CMS KY171 SRC. In one aspect, approximately or greater than about 50%, 75%, or 100% of a progeny's genetics is provided by a plant of the present disclosure that is homozygous at the cyp82e4, cyp82e5v2, and cyp82E10 loci for SEQ ID NO: 1, SEQ ID NO: 2, and SEQ ID NO: 11, respectively. In one aspect, a plant of the present disclosure has a genetic background that is at least 95%, at least 97%, at least 98%, or at least 99% similar to TND950 (phph) SRC, Narrow Leaf Madole (phph) SRC, Narrow Leaf Madole SRC, CMS TND950 SRC, CMS Narrow Leaf Madole SRC, or CMS KY171 SRC. In another aspect, a plant of the present disclosure exhibits low nornicotine and is not subject to conversion to high nornicotine. In one aspect, a plant of the present disclosure is the progeny plant of a female or male parent plant that is *Fusarium* wilt resistant. In another aspect, a plant of PD7305 SRC, PD7309 SRC, PD7312 SRC, PD7318 SRC, or PD7319 SRC has moderate resistance to black shank and moderate resistance to bacterial wilt.

In one aspect, a plant of the present disclosure is a medium-late maturing variety with moderately high yield potential. In another aspect, a plant of the present disclosure offers a broad range of important agronomic characteristics. In a further aspect, a plant of the present disclosure has one, two, three, four or more of the traits including moderate resistance to black shank, some tolerance to blue mold, black root rot resistance, and resistance to common virus diseases. In another aspect, a plant of the present disclosure has blue mold tolerance and level 4 resistance to both races of black shank and high root rot resistance. In one aspect, a plant of the present disclosure, such as TND950 (phph) SRC, Narrow Leaf Madole (phph) SRC, Narrow Leaf Madole SRC, CMS TND950 SRC, CMS Narrow Leaf Madole SRC, CMS KY171 SRC or hybrid cultivars PD7305 SRC, PD7309 SRC, PD7312 SRC, PD7318 SRC, or PD7319 SRC, lacks *Fusarium* wilt resistance. In another aspect, a plant of the present disclosure is *Fusarium* wilt resistant. In another aspect, a plant of the present disclosure has low resistance to black shank and moderate resistance to bacterial wilt.

In an aspect, the plants of the present disclosure have reduced or eliminated ability to convert nicotine to nornicotine. In an aspect, the percentage nicotine conversion is less than about 75%, 70%, 60%, 50%, or 25% of that found in TND950 (phph), Narrow Leaf Madole (phph), Narrow Leaf Madole, CMS TND950, CMS Narrow Leaf Madole, CMS KY171 or hybrid cultivars PD7305 LC, PD7309 LC, PD7312 LC, PD7318 LC, or PD7319 LC. The nicotine conversion in plants of the present disclosure, including TND950 (phph), Narrow Leaf Madole (phph), Narrow Leaf Madole, CMS TND950, CMS Narrow Leaf Madole, CMS KY171 or hybrid cultivars PD7305 LC, PD7309 LC, PD7312 LC, PD7318 LC, or PD7319 LC, can be less than about 4%, about 3.5%, about 3%, about 2.5%, about 2%, about 1.5%, or about 1%, or any range therein. In still other aspects, the nicotine conversion in plants of the present disclosure, including TND950 (phph) SRC, Narrow Leaf Madole (phph) SRC, Narrow Leaf Madole SRC, CMS TND950 SRC, CMS Narrow Leaf Madole SRC, CMS KY171 SRC or hybrid cultivars PD7305 SRC, PD7309 SRC, PD7312 SRC, PD7318 SRC, or PD7319 SRC, can be in a range from about 3% to about 1%, about 3% to about 0.5%, or about 2% to about 0.5%. In a preferred aspect, the percentage nicotine conversion is less than about 25%, 10%, 5%, or 2% of that found in TND950 (phph), Narrow Leaf Madole (phph), Narrow Leaf Madole, CMS TND950, CMS Narrow Leaf Madole, CMS KY171 and hybrid cultivars PD7305 LC, PD7309 LC, PD7312 LC, PD7318 LC, or PD7319 LC without the cyp82e4 W329Stop, the cyp82e5v2 W422Stop, and cyp82e10 P381S mutations. In an aspect, the tobacco plants of the present disclosure can have a nicotine conversion rate of about 3.5, 3.25, 3.0 or 2.75% or less. In another aspect, the nicotine conversion rate of tobacco plants of the present disclosure can be about 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6, 0.5% or less or any range therein. In another aspect, the nicotine conversion rate of tobacco plants of the present disclosure can be about 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6% or less or any range therein. In another aspect, the nicotine conversion rates can be in a range from about 0.5% to about 0.9%, about 0.5% to about 1.5%, about 0.5% to about 2.0%, about 0.5% to about 2.5%, about 0.5% to about 2.75%, and about 0.5% to about 3.0%. In another aspect, the nicotine conversion rates can be in a range from about 1.0% to about 1.5%, about 1.0% to about 1.75%, about 1.0% to about 2.0%, about 1.0% to about 2.5%, about 1.0% to about 2.75%, or about 1.0% to about 3.0%. In another aspect, the nicotine conversion rate in a plant of the present disclosure can be less than about 2.9, 2.75, 2.5, 2.25, 2.0, 1.9, 1.8, 1.7, 1.6, 1.5, 1.4, 1.3, 1.2, 1.1 or 1.0% or any range therein.

In another aspect, the tobacco plants of the present disclosure typically have a reduced amount of nornicotine of less than about 0.10% dry weight. For example, the nornicotine content in such plants can be about 1.2, 1.0, 0.7, 0.5, 0.4, 0.2, 0.1, 0.09, 0.085, 0.08, 0.075, 0.07, 0.065, 0.06, 0.055, 0.05, 0.045, 0.04, 0.035, 0.025, 0.01, 0.009, 0.0075, 0.005, 0.0025, 0.001, 0.0009, 0.00075, 0.0005, 0.00025, or 0.0001% dry weight, or undetectable, or any range therein. In another aspect, the nornicotine content can be less than about 1.2, 1.0, 0.9, 0.8, 0.7, 0.5, 0.4, 0.2, 0.1, 0.075, 0.05, 0.025, 0.01, 0.009, 0.0075, 0.005, 0.0025, 0.001, 0.0009, 0.00075, 0.0005, 0.00025, or 0.0001% dry weight, or any range therein. In another aspect, the nornicotine content in such plants can be in a range from about 1.2% to about 1.0%, about 0.7% to about 0.5%, about 0.4% to about 0.2%, about 0.1% to about 0.075%, about 0.05% to about 0.025%, about 0.01% to about 0.0075%, about 0.005% to about 0.0025%, about 0.001% to about 0.00075%, about 0.0005% to about 0.00025%, or about 0.0005% to about 0.0001% dry weight. In some aspects, in a plant of the present disclosure, the nornicotine is a relatively small percentage of total alkaloids in the plant compared to a commercial seedlot of TND950 (phph), Narrow Leaf Madole (phph), Narrow Leaf Madole, CMS TND950, CMS Narrow Leaf Madole, CMS KY171 or hybrid cultivars PD7305 LC, PD7309 LC, PD7312 LC, PD7318 LC, or PD7319 LC. In some aspects, the nornicotine in a plant of the present disclosure can be about 2% to about 1%, less than 3%, about 2%, about 1.5%, about 1%, or 0.75% of total alkaloids. Tobacco products having a reduced amount of nitrosamine content can be manufactured using tobacco plant material from plants and plant parts of the present disclosure. Thus, in some embodiments, a tobacco product manufactured using tobacco plant material from plants and plant parts of the present disclosure can comprise a reduced amount of nornicotine of less than about 3 mg/g. For example, the nornicotine content in such a product can be 3.0 mg/g, 2.5 mg/g, 2.0 mg/g, 1.5 mg/g, 1.0 mg/g, 750 µg/g, 500 µg/g, 250 µg/g, 100 µg/g, 75 µg/g, 50 µg/g, 25 µg/g, 10 µg/g, 5 µg/g, 1 µg/g, 750 ng/g, 500 ng/g, 250 ng/g, 100 ng/g, 75 ng/g, 50 ng/g, 25 ng/g, 10 ng/g, 5 ng/g, 1 ng/g, 750 pg/g, 500 pg/g, 250 pg/g, 100 pg/g, 75 pg/g, 50 pg/g, 25 pg/g, 10 pg/g, 7.0 pg/g, 5.0 pg/g, 4.0 pg/g, 2.0 pg/g, 1.0 pg/g, 0.5 pg/g, 0.4 pg/g, 0.2 pg/g, 0.1 pg/g, 0.05 pg/g, 0.01 pg/g, and the like, or undetectable, or any range therein. The tobacco product typically has a reduced amount of NNN of less than about 10 pg/g. For example, the NNN content in such a product can be about 10 pg/g, 7.0 pg/g, 5.0 pg/g, 4.0 pg/g, 2.0 pg/g, 1.0 pg/g, 0.5 pg/g, 0.4 pg/g, 0.2 pg/g, 0.1 pg/g, 0.05 pg/g, 0.01 pg/g, and the like, or undetectable, or any range therein. The percentage of secondary alkaloids relative to total alkaloid content contained in a plant of the present disclosure may not be statistically different than from a commercial seedlot of TND950 (phph), Narrow Leaf Madole (phph), Narrow Leaf Madole, CMS TND950, CMS Narrow Leaf Madole, CMS KY171 or hybrid cultivars PD7305 LC, PD7309 LC, PD7312 LC, PD7318 LC, or PD7319 LC.

Differences between two inbred tobacco varieties or two hybrid tobacco varieties can be evaluated using statistical approaches. Statistical analysis includes the calculation of mean values, determination of the statistical significance of the sources of variation, and the calculation of the appropriate variance components. Methods for determining statistical significance are known in the art. Statistical software is available, for example, the PROC GLM function of SAS. Significance is generally presented as a "p-value." A statistically significant p-value is less than 0.10. In a preferred aspect, the p-value is less than, or equal to, 0.05. In another aspect, the p-value is 0.04 or less, 0.03 or less, or 0.02 or less. In yet another aspect, a statistically significant value is less than 0.01. In yet another aspect, it can be less than 0.009, less than 0.008, less than 0.007, less than 0.006, less than 0.005, less than 0.004, less than 0.003, less than 0.002, or less than 0.001.

Tobacco plants of the present disclosure that are homozygous for the cyp82e4 W329Stop, the cyp82e5v2 W422Stop, and cyp82e10 P381S alleles have a reversion rate that is statistically significantly lower than corresponding control low-converter plants having wild type nicotine demethylase CYP82E4, E5, and E10 genes. In addition, homozygous CYP82E4, CYP82E5, and CYP82E10 triple mutant tobacco plants have a percent conversion to nornicotine of less than about 2.0%, e.g., undetectable to about 2.0%, 1.9%, 1.8%, 1.7%, 1.6%, 1.5%, 1.4%, 1.3%, 1.2%, 1.1%, 1.0%, 0.9%, 0.8%, or any range therein. In some aspects, the triple mutant tobacco plants have a percent conversion to nornicotine in a range from, for example, about 1.0% to 2.0%, 0.8% to 1.8%, 0.8% to 2.0%, or 1.0% to 2.0%.

Nicotine and nornicotine can be measured in ethylene-treated leaves using methods known in the art (e.g., gas chromatography). Percent nicotine demethylation in a sample is calculated by dividing the level of nornicotine by the combined level of nicotine and nornicotine as measured in the sample, and multiplying by 100. Percent nicotine demethylation in a sample from a plant of the present disclosure is about 50, 40, 30, 20, or 10 percent of a sample from an individual plant grown from a commercial seedlot of TND950 (phph), Narrow Leaf Madole (phph), Narrow Leaf Madole, CMS TND950, CMS Narrow Leaf Madole, CMS KY171 or hybrid cultivars PD7305 LC, PD7309 LC, PD7312 LC, PD7318 LC, or PD7319 LC.

In an aspect, the tobacco plants of the present disclosure have a USDA quality index of about 73, about 72, about 71, about 70, about 69, about 68, about 67 or about 66 or any range therein. In an aspect, the tobacco plants of the present disclosure have a USDA quality index of about 65. In another aspect, the quality index may be at least about 55, 60, 62.5 or greater, or any range therein. In another aspect, tobacco plants of the present disclosure can have a quality index in the range of about 60 to about 65, about 60 to about 70, about 62.5 to about 65, about 62.5 to about 70, or about 65 to about 70.

A plant of the present disclosure, including TND950 (phph) SRC, Narrow Leaf Madole (phph) SRC, Narrow Leaf Madole SRC, CMS TND950 SRC, CMS Narrow Leaf Madole SRC, CMS KY171 SRC or hybrid cultivars PD7305 SRC, PD7309 SRC, PD7312 SRC, PD7318 SRC, or PD7319 SRC, can have any yield potential, including high (e.g., over 3000 lbs/A), moderately high (e.g., 2200-3000 lbs/A), and moderate (e.g., less than 2000 lbs/A) yield potential.

In another aspect, the present disclosure also provides for a plant grown from the seed of a TND950 (phph) SRC, Narrow Leaf Madole (phph) SRC, Narrow Leaf Madole SRC, CMS TND950 SRC, CMS Narrow Leaf Madole SRC, CMS KY171 SRC or hybrid cultivar PD7305 SRC, PD7309 SRC, PD7312 SRC, PD7318 SRC, or PD7319 SRC plant in which alkaloids obtained from tobacco plants grown for the seed have decreased nornicotine, as well as plant parts and tissue cultures from such plants, representative sample seeds of these cultivars having been deposited with the ATCC. Seeds of hybrid cultivar PD7305 SRC are obtainable by crossing plants of cultivars CMS TND950 SRC and TND950 (phph) SRC and collecting seeds. Seeds of hybrid cultivar PD7309 SRC are obtainable by crossing plants of cultivars CMS Narrow Leaf Madole SRC and Narrow Leaf Madole (phph) SRC and collecting seeds. Seeds of hybrid cultivar PD7312 SRC are obtainable by crossing plants of cultivars CMS KY171 SRC and Narrow Leaf Madole SRC and collecting seeds. Seeds of hybrid cultivar PD7318 SRC are obtainable by crossing plants of cultivars CMS KY171 SRC and Narrow Leaf Madole (phph) SRC and collecting seeds. Seeds of hybrid cultivar PD7319 SRC are obtainable by crossing plants of cultivars CMS TND950 SRC and Narrow Leaf Madole (phph) SRC and collecting seeds.

An aspect of the present disclosure provides for parts of the cultivar TND950 (phph) SRC, Narrow Leaf Madole (phph) SRC, Narrow Leaf Madole SRC, CMS TND950 SRC, CMS Narrow Leaf Madole SRC, CMS KY171 SRC or hybrid cultivar PD7305 SRC, PD7309 SRC, PD7312 SRC, PD7318 SRC, or PD7319 SRC. A part of a cultivar can comprise any plant part and includes, but is not limited to, leaves, pollen, embryos, cotyledons, hypocotyls, roots, root tips, anthers, flowers, ovules, shoots, stems, stalks, pith and capsules, tissue culture comprising tissue, callus, cells or protoplasts of the cultivars TND950 (phph) SRC, Narrow Leaf Madole (phph) SRC, Narrow Leaf Madole SRC, CMS TND950 SRC, CMS Narrow Leaf Madole SRC, CMS KY171 SRC or hybrid cultivars PD7305 SRC, PD7309 SRC, PD7312 SRC, PD7318 SRC, or PD7319 SRC. In another aspect, the present disclosure provides for parts from hybrids of cultivars TND950 (phph) SRC, Narrow Leaf Madole (phph) SRC, Narrow Leaf Madole SRC, CMS TND950 SRC, CMS Narrow Leaf Madole SRC, CMS KY171 SRC or hybrid cultivars PD7305 SRC, PD7309 SRC, PD7312 SRC, PD7318 SRC, or PD7319 SRC derived tobacco plants. In yet another aspect, the present disclosure provides for parts from genetically modified (e.g., by conventional breeding or genetic engineering techniques) forms of the foregoing plants and tissue culture.

Additional aspects of the present disclosure provide products comprising tobacco from the plants of the present disclosure, and parts thereof. Other aspects of the disclosure provide cured plant parts, which include, but are not limited to, a leaf, pollen, ovule, embryo, cotyledon, hypocotyl, meristematic cell, protoplast, root, root tip, pistil, anther, flower, shoot, stem, pod, petiole, and the like, and combinations thereof.

Thus, in some aspects, the present disclosure provides a cured tobacco comprising the leaves of the tobacco plant designated TND950 (phph) SRC. In another aspect, the present disclosure provides a cured tobacco comprising the leaves of the tobacco plant designated Narrow Leaf Madole (phph) SRC. In another aspect, the present disclosure provides a cured tobacco comprising the leaves of the tobacco plant designated Narrow Leaf Madole SRC. In another aspect, the present disclosure provides a cured tobacco comprising the leaves of the tobacco plant designated CMS TND950 SRC. In another aspect, the present disclosure provides a cured tobacco comprising the leaves of the tobacco plant designated CMS Narrow Leaf Madole SRC. In another aspect, the present disclosure provides a cured tobacco comprising the leaves of the tobacco plant designated CMS KY171 SRC. In yet another aspect, the present disclosure provides a cured tobacco comprising the leaves of the hybrid tobacco plant designated PD7305 SRC, PD7309 SRC, PD7312 SRC, PD7318 SRC, or PD7319 SRC. Seeds of hybrid cultivar PD7305 SRC are obtainable by crossing plants of cultivars CMS TND950 SRC and TND950 (phph) SRC and collecting seeds. Seeds of hybrid cultivar PD7309 SRC are obtainable by crossing plants of cultivars CMS Narrow Leaf Madole SRC and Narrow Leaf Madole (phph) SRC and collecting seeds. Seeds of hybrid cultivar PD7312 SRC are obtainable by crossing plants of cultivars CMS KY171 SRC and Narrow Leaf Madole SRC and collecting seeds. Seeds of hybrid cultivar PD7318 SRC are obtainable by crossing plants of cultivars CMS KY171 SRC and Narrow Leaf Madole (phph) SRC and collecting seeds. Seeds of hybrid cultivar PD7319 SRC are obtainable by crossing plants of cultivars CMS TND950 SRC and Narrow Leaf Madole (phph) SRC and collecting seeds.

In an aspect, the present disclosure provides a cured tobacco comprising the stems of the tobacco plant designated TND950 (phph) SRC. In another aspect, the present disclosure provides a cured tobacco comprising the stems of the tobacco plant designated Narrow Leaf Madole (phph) SRC. In an aspect, the present disclosure provides a cured tobacco comprising the stems of the tobacco plant designated Narrow Leaf Madole SRC. In another aspect, the present disclosure provides a cured tobacco comprising the leaves of the tobacco plant designated CMS TND950 SRC. In another aspect, the present disclosure provides a cured tobacco comprising the stems of the tobacco plant designated CMS Narrow Leaf Madole SRC. In another aspect, the present disclosure provides a cured tobacco comprising the stems of the tobacco plant designated CMS KY171 SRC. In yet another aspect, the present disclosure provides a cured tobacco comprising the stems of the hybrid tobacco plant designated PD7305 SRC, PD7309 SRC, PD7312 SRC, PD7318 SRC, or PD7319 SRC. Seeds of hybrid cultivar PD7305 SRC are obtainable by crossing plants of cultivars CMS TND950 SRC and TND950 (phph) SRC and collecting seeds. Seeds of hybrid cultivar PD7309 SRC are obtainable by crossing plants of cultivars CMS Narrow Leaf Madole SRC and Narrow Leaf Madole (phph) SRC and collecting seeds. Seeds of hybrid cultivar PD7312 SRC are obtainable by crossing plants of cultivars CMS KY171 SRC and Narrow Leaf Madole SRC and collecting seeds. Seeds of hybrid cultivar PD7318 SRC are obtainable by crossing plants of cultivars CMS KY171 SRC and Narrow Leaf Madole (phph) SRC and collecting seeds. Seeds of hybrid cultivar PD7319 SRC are obtainable by crossing plants of cultivars CMS TND950 SRC and Narrow Leaf Madole (phph) SRC and collecting seeds.

In an aspect, the present disclosure provides a cured tobacco comprising the leaves and stems of the tobacco plants designated TND950 (phph) SRC. In another aspect, the present disclosure provides a cured tobacco comprising the leaves and stems of the tobacco plants designated Narrow Leaf Madole (phph) SRC. In an aspect, the present disclosure provides a cured tobacco comprising the leaves and stems of the tobacco plants designated Narrow Leaf Madole SRC. In another aspect, the present disclosure provides a cured tobacco comprising the leaves and stems of the tobacco plant designated CMS TND950 SRC. In another aspect, the present disclosure provides a cured tobacco comprising the leaves and stems of the tobacco plant designated CMS Narrow Leaf Madole SRC. In another aspect, the present disclosure provides a cured tobacco comprising the leaves and stems of the tobacco plant designated CMS KY171 SRC. In yet another aspect, the present disclosure provides a cured tobacco comprising the leaves and stems of the hybrid tobacco plant designated PD7305 SRC, PD7309 SRC, PD7312 SRC, PD7318 SRC, or PD7319 SRC. Seeds of hybrid cultivar PD7305 SRC are obtainable by crossing plants of cultivars CMS TND950 SRC and TND950 (phph) SRC and collecting seeds. Seeds of hybrid cultivar PD7309 SRC are obtainable by crossing plants of cultivars CMS Narrow Leaf Madole SRC and Narrow Leaf Madole (phph) SRC and collecting seeds. Seeds of hybrid cultivar PD7312 SRC are obtainable by crossing plants of cultivars CMS KY171 SRC and Narrow Leaf Madole SRC and collecting seeds. Seeds of hybrid cultivar PD7318 SRC are obtainable by crossing plants of cultivars CMS KY171 SRC and Narrow Leaf Madole (phph) SRC and collecting seeds. Seeds of hybrid cultivar PD7319 SRC are obtainable by crossing plants of cultivars CMS TND950 SRC and Narrow Leaf Madole (phph) SRC and collecting seeds.

The present disclosure also provides a container of TND950 (phph) SRC, Narrow Leaf Madole (phph) SRC, Narrow Leaf Madole SRC, CMS TND950 SRC, CMS Narrow Leaf Madole SRC, CMS KY171 SRC, or hybrid PD7305 SRC, PD7309 SRC, PD7312 SRC, PD7318 SRC, or PD7319 SRC seeds or other seeds of the present disclosure in which alkaloids obtained from tobacco plants grown from greater than about 50% of the seeds have decreased nornicotine. In another aspect, alkaloids obtained from TND950 (phph) SRC, Narrow Leaf Madole (phph) SRC, Narrow Leaf Madole SRC, CMS TND950 SRC, CMS Narrow Leaf Madole SRC, CMS KY171 SRC, or hybrid PD7305 SRC, PD7309 SRC, PD7312 SRC, PD7318 SRC, or PD7319 SRC plants or other plants of the present disclosure grown from greater than about 55%, 60%, 65%, 70%, 75%, 80%, 85%, 90%, or 95% of the seeds in the container have decreased nornicotine, representative samples of seeds of these cultivars having been deposited with the ATCC. Seeds of hybrid cultivar PD7305 SRC are obtainable by crossing plants of cultivars CMS TND950 SRC and TND950 (phph) SRC and collecting seeds. Seeds of hybrid cultivar PD7309 SRC are obtainable by crossing plants of cultivars CMS Narrow Leaf Madole SRC and Narrow Leaf Madole (phph) SRC and collecting seeds. Seeds of hybrid cultivar PD7312 SRC are obtainable by crossing plants of cultivars CMS KY171 SRC and Narrow Leaf Madole SRC and collecting seeds. Seeds of hybrid cultivar PD7318 SRC are obtainable by crossing plants of cultivars CMS KY171 SRC and Narrow Leaf Madole (phph) SRC and collecting seeds. Seeds of hybrid cultivar PD7319 SRC are obtainable by crossing plants of cultivars CMS TND950 SRC and Narrow Leaf Madole (phph) SRC and collecting seeds.

The container of TND950 (phph) SRC, Narrow Leaf Madole (phph) SRC, Narrow Leaf Madole SRC, CMS TND950 SRC, CMS Narrow Leaf Madole SRC, CMS KY171 SRC, or hybrid PD7305 SRC, PD7309 SRC, PD7312 SRC, PD7318 SRC, or PD7319 SRC seeds or other seeds of the present disclosure may contain any number, weight or volume of seeds. For example, a container can contain at least, or greater than, about 100, 200, 300, 400, 500, 600, 700, 800, 900, 1000, 1500, 2000, 2500, 3000, 3500, 4000 or more seeds. Alternatively, the container can contain at least, or greater than, about 1 ounce, 5 ounces, 10 ounces, 1 pound, 2 pounds, 3 pounds, 4 pounds, 5 pounds or more seeds. Representative samples of seeds of these cultivars having been deposited with the ATCC. Seeds of hybrid cultivar PD7305 SRC are obtainable by crossing plants of cultivars CMS TND950 SRC and TND950 (phph) SRC and collecting seeds. Seeds of hybrid cultivar PD7309 SRC are obtainable by crossing plants of cultivars CMS Narrow Leaf Madole SRC and Narrow Leaf Madole (phph) SRC and collecting seeds. Seeds of hybrid cultivar PD7312 SRC are obtainable by crossing plants of cultivars CMS KY171 SRC and Narrow Leaf Madole SRC and collecting seeds. Seeds of hybrid cultivar PD7318 SRC are obtainable by crossing plants of cultivars CMS KY171 SRC and Narrow Leaf Madole (phph) SRC and collecting seeds. Seeds of hybrid cultivar PD7319 SRC are obtainable by crossing plants of cultivars CMS TND950 SRC and Narrow Leaf Madole (phph) SRC and collecting seeds.

Containers of TND950 (phph) SRC, Narrow Leaf Madole (phph) SRC, Narrow Leaf Madole SRC, CMS TND950 SRC, CMS Narrow Leaf Madole SRC, CMS KY171 SRC, or hybrid PD7305 SRC, PD7309 SRC, PD7312 SRC, PD7318 SRC, or PD7319 SRC seeds or other seeds of the present disclosure may be any container available in the art. By way of a non-limiting example, a container may be a box, a bag, a packet, a pouch, a tape roll, a pail, a foil, or a tube. Representative samples of seeds of these cultivars having been deposited with the ATCC, for example. Seeds of hybrid cultivar PD7305 SRC are obtainable by crossing plants of cultivars CMS TND950 SRC and TND950 (phph) SRC and collecting seeds. Seeds of hybrid cultivar PD7309 SRC are obtainable by crossing plants of cultivars CMS Narrow Leaf Madole SRC and Narrow Leaf Madole (phph) SRC and collecting seeds. Seeds of hybrid cultivar PD7312 SRC are obtainable by crossing plants of cultivars CMS KY171 SRC and Narrow Leaf Madole SRC and collecting seeds. Seeds of hybrid cultivar PD7318 SRC are obtainable by crossing plants of cultivars CMS KY171 SRC and Narrow Leaf Madole (phph) SRC and collecting seeds. Seeds of hybrid cultivar PD7319 SRC are obtainable by crossing plants of cultivars CMS TND950 SRC and Narrow Leaf Madole (phph) SRC and collecting seeds.

In another aspect, the present disclosure also provides a container of TND950 (phph) SRC, Narrow Leaf Madole (phph) SRC, Narrow Leaf Madole SRC, CMS TND950 SRC, CMS Narrow Leaf Madole SRC, CMS KY171 SRC, or hybrid PD7305 SRC, PD7309 SRC, PD7312 SRC, PD7318 SRC, or PD7319 SRC in which greater than about 50% of TND950 (phph) SRC, Narrow Leaf Madole (phph) SRC, Narrow Leaf Madole SRC, CMS TND950 SRC, CMS Narrow Leaf Madole SRC, CMS KY171 SRC, or hybrid PD7305 SRC, PD7309 SRC, PD7312 SRC, PD7318 SRC, or PD7319 SRC or other seeds of the present disclosure have decreased nornicotine. Representative samples of seeds of these cultivars having been deposited with the ATCC. Seeds of hybrid cultivar PD7305 SRC are obtainable by crossing plants of cultivars CMS TND950 SRC and TND950 (phph) SRC and collecting seeds. Seeds of hybrid cultivar PD7309 SRC are obtainable by crossing plants of cultivars CMS Narrow Leaf Madole SRC and Narrow Leaf Madole (phph) SRC and collecting seeds. Seeds of hybrid cultivar PD7312 SRC are obtainable by crossing plants of cultivars CMS KY171 SRC and Narrow Leaf Madole SRC and collecting seeds. Seeds of hybrid cultivar PD7318 SRC are obtainable by crossing plants of cultivars CMS KY171 SRC and Narrow Leaf Madole (phph) SRC and collecting seeds. Seeds of hybrid cultivar PD7319 SRC are obtainable by crossing plants of cultivars CMS TND950 SRC and Narrow Leaf Madole (phph) SRC and collecting seeds.

In one aspect, the present disclosure provides a seed of a TND950 (phph) SRC, Narrow Leaf Madole (phph) SRC, Narrow Leaf Madole SRC, CMS TND950 SRC, CMS Narrow Leaf Madole SRC, CMS KY171 SRC, or hybrid PD7305 SRC, PD7309 SRC, PD7312 SRC, PD7318 SRC, or PD7319 SRC plant or other plant of the present disclosure in which a plant grown from a seed is male sterile. Representative samples of seeds of these cultivars having been deposited with the ATCC. Seeds of hybrid cultivar PD7305 SRC are obtainable by crossing plants of cultivars CMS TND950 SRC and TND950 (phph) SRC and collecting seeds. Seeds of hybrid cultivar PD7309 SRC are obtainable by crossing plants of cultivars CMS Narrow Leaf Madole SRC and Narrow Leaf Madole (phph) SRC and collecting seeds. Seeds of hybrid cultivar PD7312 SRC are obtainable by crossing plants of cultivars CMS KY171 SRC and Narrow Leaf Madole SRC and collecting seeds. Seeds of hybrid cultivar PD7318 SRC are obtainable by crossing plants of cultivars CMS KY171 SRC and Narrow Leaf Madole (phph) SRC and collecting seeds. Seeds of hybrid cultivar PD7319 SRC are obtainable by crossing plants of cultivars CMS TND950 SRC and Narrow Leaf Madole (phph) SRC and collecting seeds.

Tobacco material obtained from the tobacco lines, varieties or hybrids of the present disclosure can be used to make tobacco products including, without limitation, cigarette products (e.g., cigarettes and bidi cigarettes), cigar products (e.g., cigar wrapping tobacco and cigarillos), pipe tobacco products, smokeless cigarette products, smokeless tobacco products (e.g., moist snuff, dry snuff, and chewing tobacco), films, chewables, tabs, shaped parts, gels, consumable units, insoluble matrices, hollow shapes and the like. See, e.g., U.S. Patent Publication No. US 2006/0191548, which is herein incorporated by reference in its entirety.

Tobacco products derived from plants of the present disclosure also include cigarettes and other smoking articles, particularly those smoking articles including filter elements, wherein the rod of smokeable material includes cured tobacco within a tobacco blend. In an aspect, a tobacco product can include but is not limited to pipe tobacco, cigar tobacco, cigarette tobacco, chewing tobacco, leaf tobacco, shredded tobacco, and/or cut tobacco or any combination thereof.

In an aspect, a tobacco product of the instant disclosure is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, and cut tobacco. In another aspect, a tobacco product of the instant disclosure is a smokeless tobacco product. In a further aspect, a tobacco product of the instant disclosure is selected from the group consisting of loose leaf chewing tobacco, plug chewing tobacco, moist snuff, and nasal snuff. In yet another aspect, a tobacco product of the instant disclosure is selected from the group consisting of an electronically heated cigarette, an e-cigarette, an electronic vaporing device.

In an aspect, the tobacco product of the present disclosure can be a blended tobacco product. In other aspects of the disclosure, the tobacco product of the present disclosure can be a reduced nicotine tobacco product. In still other aspects, the tobacco product of the present disclosure can be a blended tobacco product with reduced nicotine content. Thus, the tobacco product of the present disclosure can be a blended reduced nicotine tobacco product. Tobacco product material comprises a blend of tobacco materials from the present disclosure, wherein the blend comprises at least about 5, 10, 20, 30, 40, 50, 60, 70, 80, 90, or 95 percent by weight of a cured tobacco, or any range therein, based on the dry weight of the tobacco material. US 2008/0245377 is herein incorporated by reference for blend mixtures in its entirety.

In an aspect, tobacco products having a reduced amount of nitrosamine content can be manufactured using tobacco plant material from plants and plant parts of the present disclosure. Thus, in some aspects, a tobacco product manufactured using tobacco plant material from plants and plant parts of the present disclosure can comprise a reduced amount of nornicotine of less than about 3 mg/g. For example, the nornicotine content in such a product can be 3.0 mg/g, 2.5 mg/g, 2.0 mg/g, 1.5 mg/g, 1.0 mg/g, 750 µg/g, 500 µg/g, 250 µg/g, 100 µg/g, 75 µg/g, 50 µg/g, 25 µg/g, 10 µg/g, 5 µg/g, 1 µg/g, 750 ng/g, 500 ng/g, 250 ng/g, 100 ng/g, 75 ng/g, 50 ng/g, 25 ng/g, 10 ng/g, 5 ng/g, 1 ng/g, 750 pg/g, 500 pg/g, 250 pg/g, 100 pg/g, 75 pg/g, 50 pg/g, 25 pg/g, 10 pg/g, 7.0 pg/g, 5.0 pg/g, 4.0 pg/g, 2.0 pg/g, 1.0 pg/g, 0.5 pg/g, 0.4 pg/g, 0.2 pg/g, 0.1 pg/g, 0.05 pg/g, 0.01 pg/g, or undetectable, or any range therein. The tobacco product typically has a reduced amount of NNN of less than about 10 pg/g. For example, the NNN content in such a product can be about 10 pg/g, 7.0 pg/g, 5.0 pg/g, 4.0 pg/g, 2.0 pg/g, 1.0 pg/g, 0.5 pg/g, 0.4 pg/g, 0.2 pg/g, 0.1 pg/g, 0.05 pg/g, 0.01 pg/g, or undetectable, or any range therein. The percentage of secondary alkaloids relative to total alkaloid content contained in a plant of the present disclosure may not be statistically different than from a commercial seedlot of TND950 (phph), Narrow Leaf Madole (phph), Narrow Leaf Madole, CMS TND950, CMS Narrow Leaf Madole, CMS KY171 or hybrid cultivars PD7305 LC, PD7309 LC, PD7312 LC, PD7318 LC, or PD7319 LC.

A tobacco plant of the present disclosure designated TND950 (phph) SRC, Narrow Leaf Madole (phph) SRC, Narrow Leaf Madole SRC, CMS TND950 SRC, CMS Narrow Leaf Madole SRC, CMS KY171 SRC, or hybrid PD7305 SRC, PD7309 SRC, PD7312 SRC, PD7318 SRC, or PD7319 SRC, carrying the cyp82e4 W329Stop, the cyp82e5v2 W422Stop, and cyp82e10 P381S alleles can be used in a plant breeding program to create useful lines, cultivars, varieties, progeny, inbreds, and hybrids. Thus, in some aspects, an $F_1$, $F_2$, $F_3$, or later generation tobacco plant containing the cyp82e4 W329Stop, the cyp82e5v2 W422Stop, and cyp82e10 P381S alleles is crossed with a second *Nicotiana* plant, and progeny of the cross are identified in which the cyp82e4 W329Stop, the cyp82e5v2 W422Stop, and cyp82e10 P381S alleles are present. It will be appreciated that the second *Nicotiana* plant can be TN90 or any other *Nicotiana* species or line, optionally with an additional desirable trait, such as herbicide resistance.

In still other aspects, methods of the present disclosure further include self-pollinating or pollinating a male sterile pollen acceptor with a pollen donor capable of being used in production of a progeny plant of the present disclosure, such as a male sterile hybrid of the present disclosure. Either the male sterile pollen acceptor plant or the pollen donor plant has at least one mutant allele, two, or even three mutant alleles at a nicotine demethylase locus, such as the cyp82e4 W329Stop, cyp82e5v2 W422Stop, and cyp82e10 P381S alleles. In an aspect, all three alleles at each nicotine demethylase locus are mutant alleles, making the plant homozygous for cyp82e4 W329Stop, the cyp82e5v2 W422Stop, and cyp82e10 P381S.

Breeding can be carried out via any known procedures. DNA fingerprinting, SNP or similar technologies may be used in a marker-assisted selection (MAS) breeding program to transfer or breed mutant alleles of a nicotine demethylase gene into other tobaccos. For example, a breeder can create segregating populations from hybridizations of a genotype containing cyp82e4 W329Stop, cyp82e5v2 W422Stop, and cyp82e10 P381S alleles with an agronomically desirable genotype. Plants in the $F_2$ or backcross generations can be screened using a marker developed from cyp82e4 W329Stop, the cyp82e5v2 W422Stop, or cyp82e10 P381S alleles or a fragment thereof, using one of the techniques known in the art or disclosed herein. Plants identified as possessing one or more cyp82e4 W329Stop, the cyp82e5v2 W422Stop, and cyp82e10 P381S alleles can be backcrossed or self-pollinated to create a second population to be screened. Depending on the expected inheritance pattern or the MAS technology used, it may be necessary to self-pollinate the selected plants before each cycle of backcrossing to aid identification of the desired individual plants. Backcrossing or other breeding procedure can be repeated until the desired phenotype of the recurrent parent is recovered. A recurrent parent in the present disclosure can be TND950 (phph) SRC, Narrow Leaf Madole (phph) SRC, Narrow Leaf Madole SRC, CMS TND950 SRC, CMS Narrow Leaf Madole SRC, or CMS KY171 SRC. Other breeding techniques can be found, for example, in Wernsman, E. A., and Rufty, R. C., 1987. Chapter Seventeen. Tobacco. pages 669-698 In: Cultivar Development. Crop Species. W. H. Fehr (ed.), MacMillan Publishing Go., Inc., New York, N.Y., incorporated herein by reference in their entireties.

*Nicotiana* species which exhibit breeding compatibility with *Nicotiana tabacum* include *Nicotiana amplexicaulis*, PI 271989; *Nicotiana benthamiana* PI 555478; *Nicotiana bigelovii* PI 555485; *Nicotiana debneyi*; *Nicotiana excelsior* PI 224063; *Nicotiana glutinosa* PI 555507; *Nicotiana goodspeedii* PI 241012; *Nicotiana gossei* PI 230953; *Nicotiana hesperis* PI 271991; *Nicotiana knightiana* PI 555527; *Nicotiana maritima* PI 555535; *Nicotiana megalosiphon* PI 555536; *Nicotiana nudicaulis* PI 555540; *Nicotiana paniculata* PI 555545; *Nicotiana plumbaginifolia* PI 555548; *Nicotiana repanda* PI 555552; *Nicotiana rustica*; *Nicotiana suaveolens* PI 230960; *Nicotiana sylvestris* PI 555569; *Nicotiana tomentosa* PI 266379; *Nicotiana tomentosiformis*; and *Nicotiana trigonophylla* PI 555572. See also, Compendium of Tobacco Diseases published by American Phytopathology Society, or The Genus *Nicotiana* Illustrated, published by Japan Tobacco Inc, hereby incorporated by reference in their entireties.

The result of a plant breeding program using the mutant tobacco plants described herein includes useful lines, cultivars, varieties, progeny, inbreds, and hybrids. As used herein, the term "cultivar" or "variety" refers to a population of plants that share constant characteristics which separate them from other plants of the same species. A cultivar or variety is often, although not always, sold commercially. While possessing one or more distinctive traits, a cultivar or variety is further characterized by a very small overall variation between individuals within that cultivar or variety. A "pure line" variety may be created by several generations of self-pollination and selection, or vegetative propagation from a single parent using tissue or cell culture techniques. A cultivar or variety can be essentially derived from another cultivar, line, or variety. As defined by the International Convention for the Protection of New Varieties of Plants (Dec. 2, 1961, as revised at Geneva on Nov. 10, 1972, on Oct. 23, 1978, and on Mar. 19, 1991), a cultivar or variety is "essentially derived" from an initial cultivar or variety if: a) it is predominantly derived from the initial cultivar or variety, or from a cultivar or variety that is predominantly derived from the initial cultivar or variety, while retaining the expression of the essential characteristics that result from the genotype or combination of genotypes of the initial cultivar or variety; b) it is clearly distinguishable from the initial cultivar or variety; and c) except for the differences which result from the act of derivation, it conforms to the initial cultivar or variety in the expression of the essential characteristics that result from the genotype or combination of genotypes of the initial cultivar or variety. Essentially derived varieties can be obtained, for example, by the selection of a natural or induced mutant, a somaclonal variant, a variant individual from plants of the initial cultivar or variety, backcrossing, or transformation. A "line" as distinguished from a cultivar or variety most often denotes a group of plants used non-commercially, for example in plant research. A line typically displays little overall variation between individuals for one or more traits of interest, although there may be some variation between individuals for other traits.

Hybrid tobacco varieties can be produced by preventing self-pollination of female parent plants (i.e., seed parents) of a first variety, permitting pollen from male parent plants of a second variety to fertilize the female parent plants, and allowing $F_1$ hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by cytoplasmic male sterility (CMS), or transgenic male sterility wherein a transgene inhibits microsporogenesis and/or pollen formation, or self-incompatibility. Female parent plants containing CMS are particularly useful. In aspects in which the female parent plants are CMS, pollen may be harvested from male fertile plants and applied manually to the stigmas of CMS female parent plants, and the resulting $F_1$ seed is harvested.

Plants can be used to form single-cross tobacco $F_1$ hybrids. In such an aspect, the plants of the parent varieties can be grown as substantially homogeneous adjoining populations to facilitate natural cross-pollination from the male parent plants to the female parent plants. The $F_1$ seed formed on the female parent plants is selectively harvested by conventional means. One also can grow the two parent plant varieties in bulk and harvest a blend of $F_1$ hybrid seed formed on the female parent and seed formed upon the male parent as the result of self-pollination. Alternatively, three-way crosses can be carried out wherein a single-cross $F_1$ hybrid is used as a female parent and is crossed with a different male parent. As another alternative, double-cross hybrids can be created wherein the $F_1$ progeny of two different single-crosses are themselves crossed. Self-incompatibility can be used to particular advantage to prevent self-pollination of female parents when forming a double-cross hybrid.

Successful crosses yield $F_1$ plants that are fertile, have cyp82e4 W329Stop, cyp82e5v2 W422Stop, and cyp82e10 P381S alleles, and can be backcrossed with one of the parents, such as TND950 (phph) SRC, Narrow Leaf Madole (phph) SRC, Narrow Leaf Madole SRC, CMS TND950 SRC, CMS Narrow Leaf Madole SRC, CMS KY171 SRC, PD7305 SRC, PD7309 SRC, PD7312 SRC, PD7318 SRC, or PD7319 SRC, if desired. In some aspects, a plant population in the $F_2$ generation is screened for cyp82e4 W329Stop, the cyp82e5v2 W422Stop, and cyp82e10 P381S alleles. Selected plants can be crossed with one of the parents and the first backcross (BC1) generation plants are self-pollinated to produce a $BC1F_2$ population that is again screened for variant nicotine demethylase gene expression (e.g., the null version of the nicotine demethylase gene). The process of backcrossing, self-pollination, and screening is repeated, for example, at least four times, until the final screening produces a plant that is fertile and reasonably similar to the recurrent parent. This plant, if desired, is self-pollinated and the progeny are subsequently screened again to confirm that the plant exhibits the same low nicotine conversion phenotype as TND950 (phph) SRC, Narrow Leaf Madole (phph) SRC, Narrow Leaf Madole SRC, CMS TND950 SRC, CMS Narrow Leaf Madole SRC, CMS KY171 SRC, PD7305 SRC, PD7309 SRC, PD7312 SRC, PD7318 SRC, or PD7319 SRC. Breeder's seed of the selected plant is produced using standard methods including, for example, field testing, confirmation of the null condition for nicotine demethylase, chemical analyses of cured leaf to determine the level of alkaloids and/or chemical analyses of cured leaf to determine the ratio of nornicotine to nicotine+ nornicotine.

In one aspect, a $F_1$ progeny is the result of a cross between TND950 SRC and CMS TND950 SRC to generate $F_1$ progeny that are male sterile. In another aspect, a $F_1$ progeny is the result of a cross between Narrow Leaf Madole SRC and CMS Narrow Leaf Madole SRC to generate $F_1$ progeny that are male sterile. In another aspect, a $F_1$ progeny is the result of a cross between Narrow Leaf Madole (phph) SRC and CMS Narrow Leaf Madole (phph) SRC to generate $F_1$ progeny that are male sterile. In another aspect, a $F_1$ progeny is the result of a cross between KY171 SRC and CMS KY171 SRC to generate $F_1$ progeny that are male sterile. In another aspect, a $F_1$ progeny is the result of a cross between TND950 (phph) SRC and CMS TND950 (phph) SRC to generate $F_1$ progeny that are male sterile. Male sterile tobacco plants may be produced by any method known in the art. Methods of producing male sterile tobacco are described in Wernsman, E. A., and Rufty, R. C. 1987. Chapter Seventeen. Tobacco. Pages 669-698 In: Cultivar Development. Crop Species. W. H. Fehr (ed.), MacMillan Publishing Go., Inc., New York, N.Y. 761 pp.

The present disclosure further provides methods of producing a tobacco plant by crossing one of cultivars TND950 (phph) SRC, Narrow Leaf Madole (phph) SRC, Narrow Leaf Madole SRC, CMS TND950 SRC, CMS Narrow Leaf Madole SRC, CMS KY171 SRC, PD7305 SRC, PD7309 SRC, PD7312 SRC, PD7318 SRC, or PD7319 SRC with itself or a different tobacco line. The disclosure further relates to methods for producing other tobacco cultivars or breeding lines derived from cultivars TND950 (phph) SRC, Narrow Leaf Madole (phph) SRC, Narrow Leaf Madole SRC, CMS TND950 SRC, CMS Narrow Leaf Madole SRC, CMS KY171 SRC, PD7305 SRC, PD7309 SRC, PD7312 SRC, PD7318 SRC, or PD7319 SRC by crossing a plant of cultivars TND950 (phph) SRC, Narrow Leaf Madole (phph) SRC, Narrow Leaf Madole SRC, CMS TND950 SRC, CMS Narrow Leaf Madole SRC, CMS KY171 SRC, PD7305 SRC, PD7309 SRC, PD7312 SRC, PD7318 SRC, or PD7319 SRC with a second tobacco plant and growing the progeny seed to yield a TND950 (phph) SRC, Narrow Leaf Madole (phph) SRC, Narrow Leaf Madole SRC, CMS TND950 SRC, CMS Narrow Leaf Madole SRC, CMS KY171 SRC, PD7305 SRC, PD7309 SRC, PD7312 SRC, PD7318 SRC, or PD7319 SRC-derived tobacco plant. An additional aspect of the present disclosure provides a method for producing a tobacco plant that contains in its genetic material one or more transgenes, comprising crossing cultivars of the present disclosure with a second cultivar containing one or more transgenes wherein progeny are produced, so that the genetic material of the progeny that result from the cross comprise the transgene(s) optionally operably linked to one or more regulatory elements. In one aspect, the second cultivar may be a plant derived from cultivars TND950 (phph) SRC, Narrow Leaf Madole (phph) SRC, Narrow Leaf Madole SRC, CMS TND950 SRC, CMS Narrow Leaf Madole SRC, CMS KY171 SRC, PD7305 SRC, PD7309 SRC, PD7312 SRC, PD7318 SRC, or PD7319 SRC transformed with one or more transgenes.

The disclosure further provides for the vegetative propagation of a plant of cultivars TND950 (phph) SRC, Narrow Leaf Madole (phph) SRC, Narrow Leaf Madole SRC, CMS TND950 SRC, CMS Narrow Leaf Madole SRC, CMS KY171 SRC, or hybrid PD7305 SRC, PD7309 SRC, PD7312 SRC, PD7318 SRC, or PD7319 SRC, hybrids and progeny thereof. In one aspect, the disclosure provides for a method of vegetatively propagating a plant of a tobacco cultivar comprising collecting tissue capable of being propagated from a plant of cultivars TND950 (phph) SRC, Narrow Leaf Madole (phph) SRC, Narrow Leaf Madole SRC, CMS TND950 SRC, CMS Narrow Leaf Madole SRC, CMS KY171 SRC, or hybrid PD7305 SRC, PD7309 SRC, PD7312 SRC, PD7318 SRC, or PD7319 SRC, cultivating the tissue to obtain a proliferated shoot and rooting the proliferated shoots to obtain a rooted plantlet. In another aspect, the plant tissue may be collected from an $F_1$ hybrid of a plant of cultivars TND950 (phph) SRC, Narrow Leaf Madole (phph) SRC, Narrow Leaf Madole SRC, CMS TND950 SRC, CMS Narrow Leaf Madole SRC, CMS KY171 SRC, or hybrid PD7305 SRC, PD7309 SRC, PD7312 SRC, PD7318 SRC, or PD7319 SRC. In an aspect, the plant tissue may be collected from an $F_2$, $F_3$, $F_4$ or later progeny plant obtained by breeding a plant of cultivars TND950 (phph) SRC, Narrow Leaf Madole (phph) SRC, Narrow Leaf Madole SRC, CMS TND950 SRC, CMS Narrow Leaf Madole SRC, CMS KY171 SRC, or hybrid PD7305 SRC, PD7309 SRC, PD7312 SRC, PD7318 SRC, or PD7319 SRC.

A plant comprising a mutation in a nicotine demethylase gene can be identified by selecting or screening the mutagenized plant material, or progeny thereof. Such screening and selection methodologies are known to those having ordinary skill in the art. Examples of screening and selection methodologies include, but are not limited to, Southern analysis, PCR amplification for detection of a polynucleotide, Northern blots, RNase protection, primer-extension, RT-PCR amplification for detecting RNA transcripts, enzymatic assays for detecting enzyme or ribozyme activity of polypeptides and polynucleotides, and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known.

It is understood that a tobacco plant of the present disclosure, including TND950 (phph) SRC, Narrow Leaf Madole (phph) SRC, Narrow Leaf Madole SRC, CMS TND950 SRC, CMS Narrow Leaf Madole SRC, CMS KY171 SRC, or hybrid PD7305 SRC, PD7309 SRC, PD7312 SRC, PD7318 SRC, or PD7319 SRC, can be transformed by a genetic construct (nucleic acid construct) or transgene using any technique known in the art. Without limitation, an example of a desired trait can include herbicide resistance, pest resistance, disease resistance, high yield, high grade index, curability, curing quality, mechanical harvestability, holding ability, leaf quality, height, plant maturation (e.g., early maturing, early to medium maturing, medium maturing, medium to late maturing, or late maturing), stalk size (e.g., small, medium, or large stalk), or leaf number per plant (e.g., small (e.g., 5-10 leaves), medium (e.g., 11-15 leaves), or large (e.g., 16-21) number of leaves), or any combination. Any plant of the present disclosure can be used as a basis for tissue culture, regeneration, transformed, or a combination of any of these. In an aspect, a plant of the present disclosure derived by tissue culture, transformation, or both has all, or essentially all, of the morphological and physiological characteristics of cultivar TND950 (phph) SRC, Narrow Leaf Madole (phph) SRC, Narrow Leaf Madole SRC, CMS TND950 SRC, CMS Narrow Leaf Madole SRC, CMS KY171 SRC, or hybrid PD7305 SRC, PD7309 SRC, PD7312 SRC, PD7318 SRC, or PD7319 SRC.

In one aspect, a method is provided comprising curing the leaves in high-temperature fire-curing conditions, where tobacco comprising SRC technology comprises at least 50% less nornicotine and at least 50% less NNN as compared to tobacco grown comprising LC technology when both are cured under high-temperature conditions. In one aspect, a high-temperature fire-curing condition comprises a maximum curing temperature of at least 160° F. In another aspect, curing of SRC and LC tobacco is performed under normal fire-curing conditions. In a further aspect, tobacco comprising SRC technology comprises at least 50% less nornicotine and at least 50% less NNN as compared to tobacco grown comprising LC technology when both are cured under normal fire-curing conditions. In one aspect, a normal fire-curing condition comprises a maximum curing temperature of less than 145° F. In another aspect, a method further comprises growing tobacco comprising SRC technology and harvesting the leaves. In an aspect of a method provided herein, KY171 SRC and KY171 LC are grown.

In an aspect, KY171 SRC comprises at least 60% less nornicotine as compared to KY171 LC when cured under normal fire-curing conditions. In an aspect, KY171 SRC comprises at least 70% less nornicotine as compared to KY171 LC when cured under normal fire-curing conditions. In a further aspect, KY171 SRC comprises at least 75% less nornicotine as compared to KY171 LC when cured under normal fire-curing conditions. In another aspect, KY171 SRC comprises at least 55% less NNN as compared to KY171 LC when cured under normal fire-curing conditions. In another aspect, KY171 SRC comprises at least 60% less NNN as compared to KY171 LC when cured under normal fire-curing conditions.

In an aspect, KY171 SRC comprises at least 55% less nornicotine as compared to KY171 LC when cured under high-temperature fire-curing conditions. In a further aspect, KY171 SRC comprises at least 60% less nornicotine as compared to KY171 LC when cured under high-temperature fire-curing conditions. In another aspect, KY171 SRC comprises at least 70% less nornicotine as compared to KY171 LC when cured under high-temperature fire-curing conditions. In an aspect, KY171 SRC comprises at least 55% less NNN as compared to KY171 LC when cured under high-temperature fire-curing conditions. In a further aspect, KY171 SRC comprises at least 60% less NNN as compared to KY171 LC when cured under high-temperature fire-curing conditions.

Having now generally described the disclosure, the same will be more readily understood through reference to the following examples that are provided by way of illustration, and are not intended to be limiting of the present disclosure, unless specified.

EXAMPLES

Example 1

Breeding of Homozygous cyp82e4 W329Stop, the cyp82e5v2 W422Stop, and cyp82e10 P381S Mutant Plants into the KY171 Dark Tobacco Cultivar KY171 SRC is a backcross-derived version of dark tobacco cultivar KY171 carrying introduced mutations in three genes (CYP82E4 (SEQ ID NO: 5), CYP82E5 (SEQ ID NO: 8), and CYP82E10 (SEQ ID NO: 9)) previously documented to encode for nicotine demethylase enzymes (Lewis et al., 2010). The introduced mutations in CYP82E4 (cyp82e4 W329Stop (SEQ ID NO: 1)) and CYP82E5 (cyp82e5v2 W422Stop (SEQ ID NO: 2)) encode for premature stop codons which render the genes non-functional. The introduced mutation in CYP82E10 (cyp82e10 P381S (SEQ ID NO: 11)) does not encode for a premature stop codon, but does render the gene product non-functional for converting nicotine to nornicotine (Lewis et al. 2010). When in homozygous condition, the three mutations result in tobacco plants with (1) reduced genetic capacity to demethylate nicotine to form nornicotine, and (2) a corresponding diminished potential to accumulate N-nitrosonornicotine (NNN). The mutation in CYP82E4 (cyp82e4 W329Stop (SEQ ID NO: 1)) also provides phenotypic stability for the "nicotine conversion" trait and eliminates the requirement to utilize the labor-intensive "LC" screening method for reducing levels of nornicotine in tobacco cultivars.

The original tobacco cultivar KY171 is a fertile inbred line. CMS KY171 is a cytoplasmic male-sterile version of KY171. To develop KY171 SRC, an individual plant of KY171 is pollinated with a plant of the genetic background DH98-325-6 carrying mutations in each of the three nicotine demethylase genes. $F_1$ individuals originating from this cross and heterozygous for each mutation are backcrossed to the recurrent parent, KY171, to produce $BC_1F_1$ progeny. $BC_1F_1$ progeny are screened using genotyping methodologies to identify individuals heterozygous for all three mutations. A single triple heterozygous $BC_1F_1$ plant is backcrossed to the recurrent parent to produce $BC_2F_1$ progeny. The process of backcrossing and identification of individuals heterozygous for all three mutations is repeated through the $BC_3F_1$, $BC_4F_1$, $BC_5F_1$, $BC_6F_1$, and $BC_7F_1$ stages. At the $BC_7F_1$ stage, individuals heterozygous for all three mutations from each pedigree are self-pollinated to produce $BC_7F_2$ seed. A large number of $BC_7F_2$ progeny from each pedigree are genotyped to identify individuals homozygous for all three mutations. A single $BC_7F_2$ plant homozygous for all three mutations is self-pollinated to produce a BC$_7$F$_3$ family (KY171 SRC) in which the wild-type CYP82E4, CYP82E5v2, and CYP82E10 alleles are replaced by the mutant alleles (cyp82e4 W329Stop, cyp82e5v2 W422Stop, and cyp82e10 P381S).

The male-sterile (CMS) version of KY171 SRC (CMS KY171 SRC) is produced by crossing a plant of CMS KY171 as a female with pollen of KY171 SRC to produce male-sterile plants heterozygous for all three mutations. A single male-sterile plant resulting from this cross is then subsequently backcrossed as a female to KY171 SRC to produce progeny that are segregating for individuals homozygous for all three mutations. Triple homozygous individuals are identified by DNA genotyping to produce the CMS KY171 SRC line. Because the line is male-sterile, it is maintained via pollination with KY171 SRC.

Commercial KY171 SRC is produced by pollinating plants of CMS KY171 SRC with pollen of KY171 SRC.

Example 2

Breeding of Homozygous cyp82e4 W329Stop, the cyp82e5v2 W422Stop, and cyp82e10 P381S Mutant Plants into the TND90 Dark Tobacco Cultivar TND90 SRC is a backcross-derived version of dark tobacco cultivar TND90 carrying introduced mutations in three genes (CYP82E4 (SEQ ID NO: 5), CYP82E5 (SEQ ID NO: 8), and CYP82E10 (SEQ ID NO: 9)) previously documented to encode for nicotine demethylase enzymes (Lewis et al., 2010). The introduced mutations in CYP82E4 (cyp82e4 W329Stop (SEQ ID NO: 1)) and CYP82E5 (cyp82e5v2 W422Stop (SEQ ID NO: 2)) encode for premature stop codons which render the genes non-functional. The introduced mutation in CYP82E10 (cyp82e10 P381S (SEQ ID NO: 11)) does not encode for a premature stop codon, but does render the gene product non-functional for converting nicotine to nornicotine (Lewis et al. 2010). When in homozygous condition, the three mutations result in tobacco plants with (1) reduced genetic capacity to demethylate nicotine to form nornicotine, and (2) a corresponding diminished potential to accumulate N-nitrosonornicotine (NNN). The mutation in CYP82E4 (cyp82e4 W329Stop (SEQ ID NO: 1)) also provides phenotypic stability for the "nicotine conversion" trait and eliminates the requirement to utilize the labor-intensive "LC" screening method for reducing levels of nornicotine in tobacco cultivars.

The original tobacco cultivars TND90, is a fertile inbred line. CMS TND90 is a cytoplasmic male-sterile version of TND90. To develop TND90 SRC, an individual plant of TND90 is pollinated with a plant of the genetic background DH98-325-6 carrying mutations in each of the three nicotine demethylase genes. F$_1$ individuals originating from this cross and heterozygous for each mutation are backcrossed to the recurrent parent, TND90, to produce BC$_1$F$_1$ progeny. BC$_1$F$_1$ progeny are screened using genotyping methodologies to identify individuals heterozygous for all three mutations. A single triple heterozygous BC$_1$F$_1$ plant is backcrossed to the recurrent parent to produce BC$_2$F$_1$ progeny. The process of backcrossing and identification of individuals heterozygous for all three mutations is repeated through the BC$_3$F$_1$, BC$_4$F$_1$, BC$_5$F$_1$, BC$_6$F$_1$, and BC$_7$F$_1$ stages. At the BC$_7$F$_1$ stage, individuals heterozygous for all three mutations from each pedigree are self-pollinated to produce BC$_7$F$_2$ seed. A large number of BC$_7$F$_2$ progeny from each pedigree are genotyped to identify individuals homozygous for all three mutations. A single BC$_7$F$_2$ plant homozygous for all three mutations is self-pollinated to produce a BC$_7$F$_3$ family (TND90 SRC) in which the wild-type CYP82E4, CYP82E5v2, and CYP82E10 alleles are replaced by the mutant alleles (cyp82e4 W329Stop, cyp82e5v2 W422Stop, and cyp82e10 P381S).

The male-sterile (CMS) version of TND90 SRC (CMS TND90 SRC) is produced by crossing a plant of CMS TND90 as a female with pollen of TND90 SRC to produce male-sterile plants heterozygous for all three mutations. A single male-sterile plant resulting from this cross is then subsequently backcrossed as a female to TND90 SRC to produce progeny that are segregating for individuals homozygous for all three mutations. Triple homozygous individuals are identified by DNA genotyping to produce the CMS TND90 SRC line. Because the line is male-sterile, it is maintained via pollination with TND90 SRC.

Commercial TND90 SRC is produced by pollinating plants of CMS TND90 SRC with pollen of TND90 SRC.

Example 3

Breeding of Homozygous cyp82e4 W329Stop, the cyp82e5v2 W422Stop, and cyp82e10 P381S Mutant Plants into the TND90 (Phph) Dark Tobacco Cultivar TND90 (phph) SRC is a backcross-derived version of dark tobacco cultivar TND90 (phph) carrying introduced mutations in three genes (CYP82E4 (SEQ ID NO: 5), CYP82E5 (SEQ ID NO: 8), and CYP82E10 (SEQ ID NO: 9)) previously documented to encode for nicotine demethylase enzymes (Lewis et al., 2010). The introduced mutations in CYP82E4 (cyp82e4 W329Stop (SEQ ID NO: 1)) and CYP82E5 (cyp82e5v2 W422Stop (SEQ ID NO: 2)) encode for premature stop codons which render the genes non-functional. The introduced mutation in CYP82E10 (cyp82e10 P381S (SEQ ID NO: 11)) does not encode for a premature stop codon, but does render the gene product non-functional for converting nicotine to nornicotine (Lewis et al. 2010). When in homozygous condition, the three mutations result in tobacco plants with (1) reduced genetic capacity to demethylate nicotine to form nornicotine, and (2) a corresponding diminished potential to accumulate N-nitrosonornicotine (NNN). The mutation in CYP82E4 (cyp82e4 W329Stop (SEQ ID NO: 1)) also provides phenotypic stability for the "nicotine conversion" trait and eliminates the requirement to utilize the labor-intensive "LC" screening method for reducing levels of nornicotine in tobacco cultivars.

The original tobacco cultivar TND90 (phph) is a fertile inbred line. CMS TND90 (phph) is a cytoplasmic male-sterile version of TND90 (phph). To develop TND90 (phph) SRC, an individual plant of TND90 (phph) is pollinated with a plant of the genetic background DH98-325-6 carrying mutations in each of the three nicotine demethylase genes. F$_1$ individuals originating from this cross and heterozygous for each mutation are backcrossed to the recurrent parent, TND90 (phph), to produce BC$_1$F$_1$ progeny. BC$_1$F$_1$ progeny are screened using genotyping methodologies to identify individuals heterozygous for all three mutations. A single triple heterozygous BC$_1$F$_1$ plant is backcrossed to the recurrent parent to produce BC$_2$F$_1$ progeny. The process of backcrossing and identification of individuals heterozygous for all three mutations is repeated through the BC$_3$F$_1$, BC$_4$F$_1$, BC$_5$F$_1$, BC$_6$F$_1$, and BC$_7$F$_1$ stages. At the BC$_7$F$_1$ stage, individuals heterozygous for all three mutations from each pedigree are self-pollinated to produce BC$_7$F$_2$ seed. A large number of BC$_7$F$_2$ progeny from each pedigree are genotyped to identify individuals homozygous for all three mutations. A single BC$_7$F$_2$ plant homozygous for all three mutations is self-pollinated to produce a BC₇F₃ family (TND90 (phph) SRC) in which the wild-type CYP82E4, CYP82E5v2, and CYP82E10 alleles are replaced by the mutant alleles (cyp82e4 W329Stop, cyp82e5v2 W422Stop, and cyp82e10 P381S).

The male-sterile (CMS) version of TND90 (phph) SRC (CMS TND90 (phph) SRC) is produced by crossing a plant of CMS TND90 (phph) as a female with pollen of TND90 (phph) SRC to produce male-sterile plants heterozygous for all three mutations. A single male-sterile plant resulting from this cross is then subsequently backcrossed as a female to TND90 (phph) SRC to produce progeny that are segregating for individuals homozygous for all three mutations. Triple homozygous individuals are identified by DNA genotyping to produce the TND90 (phph) SRC line. Because the line is male-sterile, it is maintained via pollination with TND90 (phph) SRC.

Commercial TND90 (phph) SRC is produced by pollinating plants of CMS TND90 (phph) SRC with pollen of TND90 (phph) SRC.

Example 4

Breeding of Homozygous cyp82e4 W329Stop, the cyp82e5v2 W422Stop, and cyp82e10 P381S Mutant Plants into the Narrow Leaf Madole Dark Tobacco Cultivar Narrow Leaf Madole SRC is a backcross-derived version of dark tobacco cultivar Narrow Leaf Madole carrying introduced mutations in three genes (CYP82E4 (SEQ ID NO: 5), CYP82E5 (SEQ ID NO: 8), and CYP82E10 (SEQ ID NO: 9)) previously documented to encode for nicotine demethylase enzymes (Lewis et al., 2010). The introduced mutations in CYP82E4 (cyp82e4 W329Stop (SEQ ID NO: 1)) and CYP82E5 (cyp82e5v2 W422Stop (SEQ ID NO: 2)) encode for premature stop codons which render the genes non-functional. The introduced mutation in CYP82E10 (cyp82e10 P381S (SEQ ID NO: 11)) does not encode for a premature stop codon, but does render the gene product non-functional for converting nicotine to nornicotine (Lewis et al. 2010). When in homozygous condition, the three mutations result in tobacco plants with (1) reduced genetic capacity to demethylate nicotine to form nornicotine, and (2) a corresponding diminished potential to accumulate N-nitrosonornicotine (NNN). The mutation in CYP82E4 (cyp82e4 W329Stop (SEQ ID NO: 1)) also provides phenotypic stability for the "nicotine conversion" trait and eliminates the requirement to utilize the labor-intensive "LC" screening method for reducing levels of nornicotine in tobacco cultivars.

The original tobacco cultivar Narrow Leaf Madole is a fertile inbred line. CMS Narrow Leaf Madole is a cytoplasmic male-sterile version of Narrow Leaf Madole. To develop Narrow Leaf Madole SRC, an individual plant of Narrow Leaf Madole is pollinated with a plant of the genetic background DH98-325-6 carrying mutations in each of the three nicotine demethylase genes. F₁ individuals originating from this cross and heterozygous for each mutation are backcrossed to the recurrent parent, Narrow Leaf Madole, to produce BC₁F₁ progeny. BC₁F₁ progeny are screened using genotyping methodologies to identify individuals heterozygous for all three mutations. A single triple heterozygous BC₁F₁ plant is backcrossed to the recurrent parent to produce BC₂F₁ progeny. The process of backcrossing and identification of individuals heterozygous for all three mutations is repeated through the BC₃F₁, BC₄F₁, BC₅F₁, BC₆F₁, and BC₇F₁ stages. At the BC₇F₁ stage, individuals heterozygous for all three mutations from each pedigree are self-pollinated to produce BC₇F₂ seed. A large number of BC₇F₂ progeny from each pedigree are genotyped to identify individuals homozygous for all three mutations. A single BC₇F₂ plant homozygous for all three mutations is self-pollinated to produce a BC₇F₃ family (Narrow Leaf Madole SRC) in which the wild-type CYP82E4, CYP82E5v2, and CYP82E10 alleles of NC1209-23 are replaced by the mutant alleles (cyp82e4 W329Stop, cyp82e5v2 W422 Stop, and cyp82e10 P381S).

The male-sterile (CMS) version of Narrow Leaf Madole SRC (CMS Narrow Leaf Madole SRC) is produced by crossing a plant of CMS Narrow Leaf Madole as a female with pollen of Narrow Leaf Madole SRC to produce male-sterile plants heterozygous for all three mutations. A single male-sterile plant resulting from this cross is then subsequently backcrossed as a female to Narrow Leaf Madole SRC to produce progeny that are segregating for individuals homozygous for all three mutations. Triple homozygous individuals are identified by DNA genotyping to produce the CMS Narrow Leaf Madole SRC line. Because the line is male-sterile, it is maintained via pollination with Narrow Leaf Madole SRC.

Commercial Narrow Leaf Madole SRC is produced by pollinating plants of CMS Narrow Leaf Madole SRC with pollen of Narrow Leaf Madole SRC.

Example 5

Assessing Nornicotine and NNN Amounts in Fire-Cured KY171 SRC Dark Tobacco

To assess the differences in nornicotine and NNN in KY171 SRC, both KY171 SRC and KY171 LC are grown using standard growth conditions and fire-cured according to recommended fire-curing practices (See, e.g., 2017-2018 *Burley and Dark Tobacco Production Guide* (B. Pearce ed., (2017)). 36 sticks of both KY171 SRC and KY171 LC are cured for a total of 6 replications per variety.

The level of the alkaloid nornicotine is determined with Gas Chromatography followed by Mass Spectrometry (GC-MS). For example, one gram of cured leaf tissue is mixed with 10 mls of 2N NaOH, followed by incubation at room temperature for fifteen minutes. Nornicotine is then extracted by addition of 50 mls of 0.04% quinolone (w/v) dissolved in methyl-tert-butyl ether followed by rotation on a linear shaker for three hours. After phase separation, nornicotine levels are determined using an Agilent 6890 Gas Chromatograph and an Agilent 5973N Mass Spectrometer. Under normal curing conditions, KY171 SRC tobacco shows a 78% reduction in nornicotine levels (FIG. 1).

Figure 2:
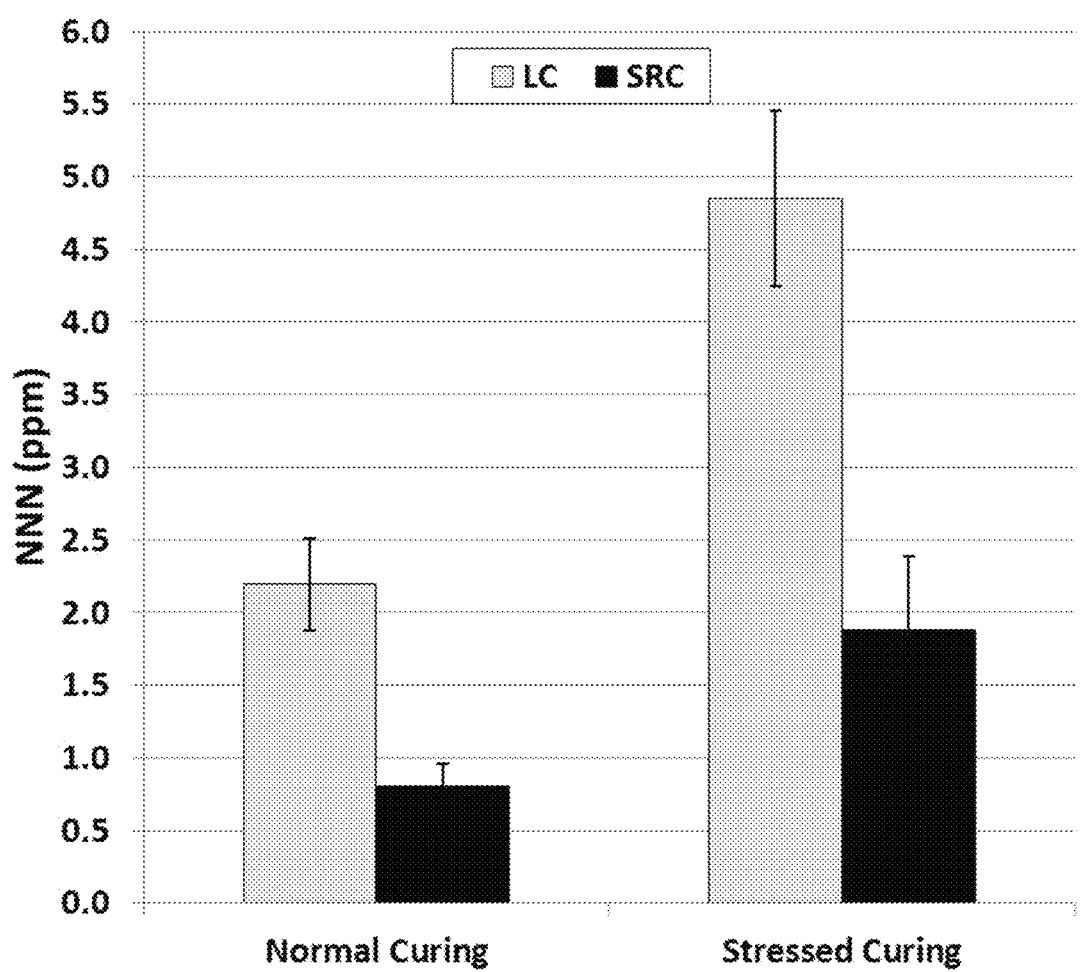
FIG. 2 depicts the amount of NNN, in parts per million, found in LC varieties compared to the same varieties comprising SRC technology when grown and cured under normal conditions as compared to growth under normal conditions and curing under high-temperature stressed curing conditions.

NNN is measured by crushing 750 mg of freeze-dried leaves and mixing with 30 mls of 10 mM ammonium acetate. After incubation in a shaker for 30 minutes, approximately 4 mls of sample is transferred into disposable culture tubes containing 0.25 ml of concentrated ammonium hydroxide. The sample is vortexed briefly and 1.5 mls is added to a prewashed and conditioned extraction cartridge with a flow rate of 1 to 2 drops per second. Analytes are eluted from the sample using 1.5 mls of 70:30 methanol with 0.1% acetic acid. Samples are analyzed using liquid chromatography with tandem mass spectrometry (LC/MS/MS). Under normal curing conditions, KY171 SRC tobacco shows a 64% reduction in NNN levels compared to KY171 LC (FIG. 2).

Figure 3:
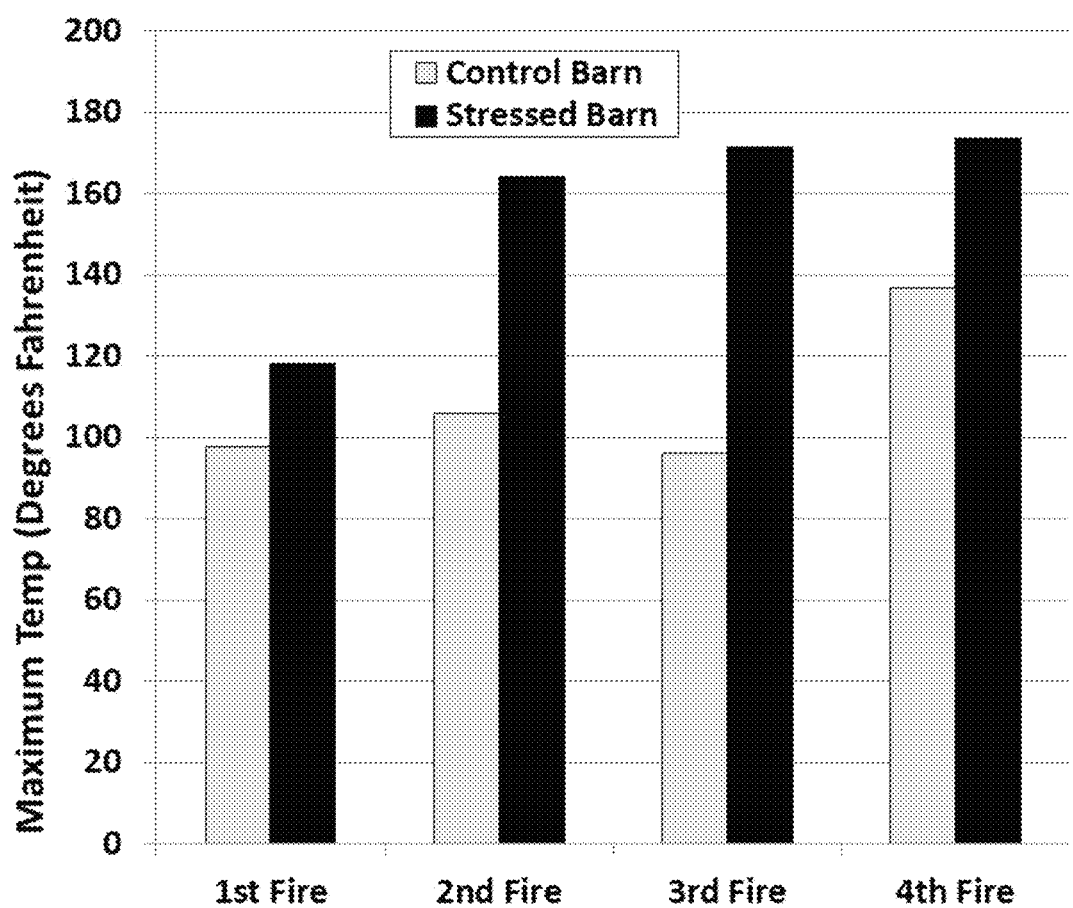
FIG. 3 depicts the maximum temperature reached (in degrees Fahrenheit) during the four firings used to fire-cure LC and SRC dark tobacco varieties in both the control curing barn and the high-temperature stressed curing barn.

The amounts of NNN and nornicotine are also measured for both KY171 SRC and KY171 LC tobacco cured under high-temperature stress conditions. To create high-temperature stress conditions, tobacco that is being cured is subjected to higher temperature fires. Similar to recommended fire-curing practices, four fires are burned during the curing period; however, in the stressed barn, the fires are brought to a much higher temperature (FIG. 3). Under the high temperature stressed curing conditions, nornicotine is again reduced by 70% in KY171 SRC tobacco compared to KY171 LC (FIG. 1) and NNN is reduced by 61% in KY171 SRC tobacco compared to KY171 LC (FIG. 2). SRC technology in KY171 acts to reduce the amount of both nornicotine and NNN compared to KY171 LC Dark Tobacco lines under both recommended and high-temperature stress curing conditions.

Example 6

Breeding of Homozygous cyp82e4 W329Stop, the cyp82e5v2 W422Stop, and cyp82e10 P381S Mutant Plants into the Narrow Leaf Madole (Phph) Dark Tobacco Cultivar Narrow Leaf Madole (phph) SRC is a backcross-derived version of dark tobacco cultivar Narrow Leaf Madole (phph) carrying introduced mutations in three genes (CYP82E4 (SEQ ID NO: 5), CYP82E5 (SEQ ID NO: 8), and CYP82E10 (SEQ ID NO: 9)) previously documented to encode for nicotine demethylase enzymes (Lewis et al., 2010). The introduced mutations in CYP82E4 (cyp82e4 W329Stop (SEQ ID NO: 1)) and CYP82E5 (cyp82e5v2 W422Stop (SEQ ID NO: 2)) encode for premature stop codons which render the genes non-functional. The introduced mutation in CYP82E10 (cyp82e10 P381S (SEQ ID NO: 11)) does not encode for a premature stop codon, but does render the gene product non-functional for converting nicotine to nornicotine (Lewis et al. 2010). When in homozygous condition, the three mutations result in tobacco plants with (1) reduced genetic capacity to demethylate nicotine to form nornicotine, and (2) a corresponding diminished potential to accumulate N-nitrosonornicotine (NNN). The mutation in CYP82E4 (cyp82e4 W329Stop (SEQ ID NO: 1)) also provides phenotypic stability for the "nicotine conversion" trait and eliminates the requirement to utilize the labor-intensive "LC" screening method for reducing levels of nornicotine in tobacco cultivars.

The original tobacco cultivar Narrow Leaf Madole (phph) is a fertile inbred line. CMS Narrow Leaf Madole (phph) is a cytoplasmic male-sterile version of Narrow Leaf Madole (phph). To develop Narrow Leaf Madole (phph) SRC, an individual plant of Narrow Leaf Madole (phph) is pollinated with a plant of the genetic background DH98-325-6 carrying mutations in each of the three nicotine demethylase genes. $F_1$ individuals originating from this cross and heterozygous for each mutation are backcrossed to the recurrent parent, Narrow Leaf Madole (phph), to produce $BC_1F_1$ progeny. $BC_1F_1$ progeny are screened using genotyping methodologies to identify individuals heterozygous for all three mutations. A single triple heterozygous $BC_1F_1$ plant is backcrossed to the recurrent parent to produce $BC_2F_1$ progeny. The process of backcrossing and identification of individuals heterozygous for all three mutations is repeated through the $BC_3F_1$, $BC_4F_1$, $BC_5F_1$, $BC_6F_1$, and $BC_7F_1$ stages. At the $BC_7F_1$ stage, individuals heterozygous for all three mutations from each pedigree are self-pollinated to produce $BC_7F_2$ seed. A large number of $BC_7F_2$ progeny from each pedigree are genotyped to identify individuals homozygous for all three mutations. A single $BC_7F_2$ plant homozygous for all three mutations is self-pollinated to produce a $BC_7F_3$ family (Narrow Leaf Madole (phph) SRC) in which the wild-type CYP82E4, CYP82E5v2, and CYP82E10 alleles are replaced by the mutant alleles (cyp82e4 W329Stop, cyp82e5v2 W422Stop, and cyp82e10 P381S).

The male-sterile (CMS) version of Narrow Leaf Madole (phph) SRC (CMS Narrow Leaf Madole (phph) SRC) is produced by crossing a plant of CMS Narrow Leaf Madole (phph) as a female with pollen of Narrow Leaf Madole (phph) SRC to produce male-sterile plants heterozygous for all three mutations. A single male-sterile plant resulting from this cross is then subsequently backcrossed as a female to Narrow Leaf Madole (phph) SRC to produce progeny that are segregating for individuals homozygous for all three mutations. Triple homozygous individuals are identified by DNA genotyping to produce the CMS Narrow Leaf Madole (phph) SRC line. Because the line is male-sterile, it is maintained via pollination with Narrow Leaf Madole (phph) SRC.

Commercial Narrow Leaf Madole (phph) SRC is produced by pollinating plants of CMS Narrow Leaf Madole (phph) SRC with pollen of Narrow Leaf Madole (phph) SRC.

TABLE 1

Breeding of Hybrid SRC lines

| Hybrid | Female parent | Male Parent |
|---|---|---|
| PD7305 SRC | CMS TND950 SRC | TND950 (phph) SRC |
| PD7309 SRC | CMS Narrow Leaf Madole SRC | Narrow Leaf Madole (phph) SRC |
| PD7312 SRC | CMS KY171 SRC | Narrow Leaf Madole SRC |
| PD7318 SRC | CMS KY171 SRC | Narrow Leaf Madole (phph) SRC |
| PD7319 SRC | CMS TND950 SRC | Narrow Leaf Madole (phph) SRC |

Example 7

Breeding of Homozygous cyp82e4 W329Stop, the cyp82e5v2 W422Stop, and cyp82e10 P381S Mutant Plants into the PD7305 LC Dark Tobacco Cultivar The original tobacco cultivar PD7305 LC is a hybrid generated by pollinating plants of a male-sterile breeding line CMS TND950 with pollen produced by fertile breeding line TND950 (phph). Hybrid cultivar PD7305 SRC is a hybrid generated by pollinating plants of a male-sterile breeding line CMS TND950 SRC with pollen produced by fertile breeding line TND950 (phph) SRC (Table 1).

Each SRC line carries introduced deleterious mutations in three genes (CYP82E4 (SEQ ID NO: 5), CYP82E5 (SEQ ID NO: 8), and CYP82E10 (SEQ ID NO: 9)) previously documented to encode for nicotine demethylase enzymes (Lewis et al., *Phytochemistry*, 71 (2010), 1988-1998). The introduced mutations in CYP82E4 (cyp82e4 W329Stop (SEQ ID NO: 1)) and CYP82E5 (cyp82e5v2 W422Stop (SEQ ID NO: 2)) encode for premature stop codons which render the genes non-functional. The introduced mutation in CYP82E10 (cyp82e10 P381S (SEQ ID NO: 11)) does not encode for a premature stop codon, but does render the gene product non-functional for converting nicotine to nornicotine (Id.). When in homozygous condition, the three mutations result in tobacco plants with (1) reduced genetic capacity to demethylate nicotine to form nornicotine, and (2) a corresponding diminished potential to accumulate N-nitrosonornicotine (NNN). The mutation in CYP82E4 (cyp82e4 W329Stop (SEQ ID NO: 1)) also provides phenotypic stability for the "nicotine conversion" trait and eliminates the requirement to utilize the labor-intensive "LC" screening method for reducing levels of nornicotine in tobacco cultivars (see e.g., Jack et al. 2007. Implications of reducing nornicotine accumulation in burley tobacco: appendix A—the LC protocol. *Rec. Adv. Tob. Sci.* 33: 58-79).

$BC_1F_1$ progenies are screened using genotyping methodologies to identify individuals heterozygous for all three mutations. A single $BC_1F_1$ plant from each pedigree is backcrossed to the recurrent parent, to produce $BC_2F_1$ progenies. The process of backcrossing and identification of individuals heterozygous for all three mutations is repeated through the $BC_3F_1$, $BC_4F_1$, $BC_5F_1$, $BC_6F_1$, and $BC_7F_1$ stages. At the $BC_7F_1$ stage, individuals heterozygous for all three mutations from each pedigree are self-pollinated to produce $BC_7F_2$ seed. A large number of $BC_7F_2$ progeny from each pedigree are genotyped to identify individuals homozygous for all three mutations. $BC_7F_2$ plants homozygous for all three mutations are self-pollinated to produce $BC_7F_3$ families (SRC lines) in which the wild-type CYP82E4, CYP82E5v2, and CYP82E10 alleles are replaced by the mutant alleles (cyp82e4 W329Stop, cyp82e5v2 W422Stop, and cyp82e10 P381S).

The female parental line of PD7305 LC, CMS TND950, is cytoplasmic male sterile which causes pollen to not be produced. To develop CMS TND950 SRC dark tobacco, a plant of CMS TND950 was crossed with TND950 SRC dark tobacco to produce male-sterile plants heterozygous for all three mutations. A single male-sterile plant resulting from this cross was then subsequently backcrossed as a female to TND950 SRC dark tobacco to produce progeny that were segregating for individuals homozygous for all three mutations. Triple homozygous individuals were identified by DNA genotyping to produce the CMS TND950 SRC dark tobacco line. Because the line is male-sterile, it is maintained via pollination with TND950 SRC dark tobacco.

Example 8

Breeding of Homozygous cyp82e4 W329Stop, the cyp82e5v2 W422Stop, and cyp82e10 P381S Mutant Plants into the PD7309 LC Dark Tobacco Cultivar The original tobacco cultivar PD7309 LC is a hybrid generated by pollinating plants of a male-sterile breeding line CMS Narrow Leaf Madole with pollen produced by fertile breeding line Narrow Leaf Madole (phph). Hybrid cultivar PD7309 SRC is a hybrid generated by pollinating plants of a male-sterile breeding line CMS Narrow Leaf Madole SRC with pollen produced by fertile breeding line Narrow Leaf Madole (phph) SRC (Table 1).

Each SRC line carries introduced deleterious mutations in three genes (CYP82E4 (SEQ ID NO: 5), CYP82E5 (SEQ ID NO: 8), and CYP82E10 (SEQ ID NO: 9)) previously documented to encode for nicotine demethylase enzymes (Lewis et al., *Phytochemistry*, 71 (2010), 1988-1998). The introduced mutations in CYP82E4 (cyp82e4 W329Stop (SEQ ID NO: 1)) and CYP82E5 (cyp82e5v2 W422Stop (SEQ ID NO: 2)) encode for premature stop codons which render the genes non-functional. The introduced mutation in CYP82E10 (cyp82e10 P381S (SEQ ID NO: 11)) does not encode for a premature stop codon, but does render the gene product non-functional for converting nicotine to nornicotine (Id.). When in homozygous condition, the three mutations result in tobacco plants with (1) reduced genetic capacity to demethylate nicotine to form nornicotine, and (2) a corresponding diminished potential to accumulate N-nitrosonornicotine (NNN). The mutation in CYP82E4 (cyp82e4 W329Stop (SEQ ID NO: 1)) also provides phenotypic stability for the "nicotine conversion" trait and eliminates the requirement to utilize the labor-intensive "LC" screening method for reducing levels of nornicotine in tobacco cultivars (see e.g., Jack et al. 2007. Implications of reducing nornicotine accumulation in burley tobacco: appendix A—the LC protocol. *Rec. Adv. Tob. Sci.* 33: 58-79).

$BC_1F_1$ progenies are screened using genotyping methodologies to identify individuals heterozygous for all three mutations. A single $BC_1F_1$ plant from each pedigree is backcrossed to the recurrent parent, to produce $BC_2F_1$ progenies. The process of backcrossing and identification of individuals heterozygous for all three mutations is repeated through the $BC_3F_1$, $BC_4F_1$, $BC_5F_1$, $BC_6F_1$, and $BC_7F_1$ stages. At the $BC_7F_1$ stage, individuals heterozygous for all three mutations from each pedigree are self-pollinated to produce $BC_7F_2$ seed. A large number of $BC_7F_2$ progeny from each pedigree are genotyped to identify individuals homozygous for all three mutations. $BC_7F_2$ plants homozygous for all three mutations are self-pollinated to produce $BC_7F_3$ families (SRC lines) in which the wild-type CYP82E4, CYP82E5v2, and CYP82E10 alleles are replaced by the mutant alleles (cyp82e4 W329Stop, cyp82e5v2 W422Stop, and cyp82e10 P381S).

The female parental line of PD7309 LC, CMS Narrow Leaf Madole, is cytoplasmic male sterile which causes pollen to not be produced. To develop CMS Narrow Leaf Madole SRC dark tobacco, a plant of CMS Narrow Leaf Madole was crossed with Narrow Leaf Madole SRC dark tobacco to produce male-sterile plants heterozygous for all three mutations. A single male-sterile plant resulting from this cross was then subsequently backcrossed as a female to Narrow Leaf Madole SRC dark tobacco to produce progeny that were segregating for individuals homozygous for all three mutations. Triple homozygous individuals were identified by DNA genotyping to produce the CMS Narrow Leaf Madole SRC dark tobacco line. Because the line is male-sterile, it is maintained via pollination with Narrow Leaf Madole SRC dark tobacco.

Example 9

Breeding of Homozygous cyp82e4 W329Stop, the cyp82e5v2 W422Stop, and cyp82e10 P381S Mutant Plants into the PD7312 LC LC Dark Tobacco Cultivar The original tobacco cultivar PD7312 LC is a hybrid generated by pollinating plants of a male-sterile breeding line CMS KY171 with pollen produced by fertile breeding line Narrow Leaf Madole. Hybrid cultivar PD7312 SRC is a hybrid generated by pollinating plants of a male-sterile breeding line CMS KY171 SRC with pollen produced by fertile breeding line Narrow Leaf Madole SRC (Table 1).

Each SRC line carries introduced deleterious mutations in three genes (CYP82E4 (SEQ ID NO: 5), CYP82E5 (SEQ ID NO: 8), and CYP82E10 (SEQ ID NO: 9)) previously documented to encode for nicotine demethylase enzymes (Lewis et al., *Phytochemistry*, 71 (2010), 1988-1998). The introduced mutations in CYP82E4 (cyp82e4 W329Stop (SEQ ID NO: 1)) and CYP82E5 (cyp82e5v2 W422Stop (SEQ ID NO: 2)) encode for premature stop codons which render the genes non-functional. The introduced mutation in CYP82E10 (cyp82e10 P381S (SEQ ID NO: 11)) does not encode for a premature stop codon, but does render the gene product non-functional for converting nicotine to nornicotine (Id.). When in homozygous condition, the three mutations result in tobacco plants with (1) reduced genetic capacity to demethylate nicotine to form nornicotine, and (2) a corresponding diminished potential to accumulate N-nitrosonornicotine (NNN). The mutation in CYP82E4 (cyp82e4 W329Stop (SEQ ID NO: 1)) also provides phenotypic stability for the "nicotine conversion" trait and eliminates the requirement to utilize the labor-intensive "LC" screening method for reducing levels of nornicotine in tobacco cultivars (see e.g., Jack et al. 2007. Implications of reducing nornicotine accumulation in burley tobacco: appendix A—the LC protocol. *Rec. Adv. Tob. Sci.* 33: 58-79).

$BC_1F_1$ progenies are screened using genotyping methodologies to identify individuals heterozygous for all three mutations. A single $BC_1F_1$ plant from each pedigree is backcrossed to the recurrent parent, to produce $BC_2F_1$ progenies. The process of backcrossing and identification of individuals heterozygous for all three mutations is repeated through the $BC_3F_1$, $BC_4F_1$, $BC_5F_1$, $BC_6F_1$, and $BC_7F_1$ stages. At the $BC_7F_1$ stage, individuals heterozygous for all three mutations from each pedigree are self-pollinated to produce $BC_7F_2$ seed. A large number of $BC_7F_2$ progeny from each pedigree are genotyped to identify individuals homozygous for all three mutations. $BC_7F_2$ plants homozygous for all three mutations are self-pollinated to produce $BC_7F_3$ families (SRC lines) in which the wild-type CYP82E4, CYP82E5v2, and CYP82E10 alleles are replaced by the mutant alleles (cyp82e4 W329Stop, cyp82e5v2 W422Stop, and cyp82e10 P381S).

The female parental line of PD7312 LC, CMS KY171, is cytoplasmic male sterile which causes pollen to not be produced. To develop CMS KY171 SRC dark tobacco, a plant of CMS KY171 was crossed with KY171 SRC dark tobacco to produce male-sterile plants heterozygous for all three mutations. A single male-sterile plant resulting from this cross was then subsequently backcrossed as a female to KY171 SRC dark tobacco to produce progeny that were segregating for individuals homozygous for all three mutations. Triple homozygous individuals were identified by DNA genotyping to produce the CMS KY171 SRC dark tobacco line. Because the line is male-sterile, it is maintained via pollination with KY171 SRC dark tobacco.

Example 10

Breeding of Homozygous cyp82e4 W329Stop, the cyp82e5v2 W422Stop, and cyp82e10 P381S Mutant Plants into the PD7318 LC Dark Tobacco Cultivar The original tobacco cultivar PD7318 LC is a hybrid generated by pollinating plants of a male-sterile breeding line CMS KY171 with pollen produced by fertile breeding line Narrow Leaf Madole (phph). Hybrid cultivar PD7318 SRC is a hybrid generated by pollinating plants of a male-sterile breeding line CMS KY171 SRC with pollen produced by fertile breeding line Narrow Leaf Madole (phph) SRC (Table 1).

Each SRC line carries introduced deleterious mutations in three genes (CYP82E4 (SEQ ID NO: 5), CYP82E5 (SEQ ID NO: 8), and CYP82E10 (SEQ ID NO: 9)) previously documented to encode for nicotine demethylase enzymes (Lewis et al., *Phytochemistry*, 71 (2010), 1988-1998). The introduced mutations in CYP82E4 (cyp82e4 W329Stop (SEQ ID NO: 1)) and CYP82E5 (cyp82e5v2 W422Stop (SEQ ID NO: 2)) encode for premature stop codons which render the genes non-functional. The introduced mutation in CYP82E10 (cyp82e10 P381S (SEQ ID NO: 11)) does not encode for a premature stop codon, but does render the gene product non-functional for converting nicotine to nornicotine (Id.). When in homozygous condition, the three mutations result in tobacco plants with (1) reduced genetic capacity to demethylate nicotine to form nornicotine, and (2) a corresponding diminished potential to accumulate N-nitrosonornicotine (NNN). The mutation in CYP82E4 (cyp82e4 W329Stop (SEQ ID NO: 1)) also provides phenotypic stability for the "nicotine conversion" trait and eliminates the requirement to utilize the labor-intensive "LC" screening method for reducing levels of nornicotine in tobacco cultivars (see e.g., Jack et al. 2007. Implications of reducing nornicotine accumulation in burley tobacco: appendix A—the LC protocol. *Rec. Adv. Tob. Sci.* 33: 58-79).

$BC_1F_1$ progenies are screened using genotyping methodologies to identify individuals heterozygous for all three mutations. A single $BC_1F_1$ plant from each pedigree is backcrossed to the recurrent parent, to produce $BC_2F_1$ progenies. The process of backcrossing and identification of individuals heterozygous for all three mutations is repeated through the $BC_3F_1$, $BC_4F_1$, $BC_5F_1$, $BC_6F_1$, and $BC_7F_1$ stages. At the $BC_7F_1$ stage, individuals heterozygous for all three mutations from each pedigree are self-pollinated to produce $BC_7F_2$ seed. A large number of $BC_7F_2$ progeny from each pedigree are genotyped to identify individuals homozygous for all three mutations. $BC_7F_2$ plants homozygous for all three mutations are self-pollinated to produce $BC_7F_3$ families (SRC lines) in which the wild-type CYP82E4, CYP82E5v2, and CYP82E10 alleles are replaced by the mutant alleles (cyp82e4 W329Stop, cyp82e5v2 W422Stop, and cyp82e10 P381S).

The female parental line of PD7318 LC, CMS KY171, is cytoplasmic male sterile which causes pollen to not be produced. To develop CMS KY171 SRC dark tobacco, a plant of CMS KY171 was crossed with KY171 SRC dark tobacco to produce male-sterile plants heterozygous for all three mutations. A single male-sterile plant resulting from this cross was then subsequently backcrossed as a female to KY171 SRC dark tobacco to produce progeny that were segregating for individuals homozygous for all three mutations. Triple homozygous individuals were identified by DNA genotyping to produce the CMS KY171 SRC dark tobacco line. Because the line is male-sterile, it is maintained via pollination with KY171 SRC dark tobacco.

Example 11

Breeding of Homozygous cyp82e4 W329Stop, the cyp82e5v2 W422Stop, and cyp82e10 P381S Mutant Plants into the PD7319 LC Dark Tobacco Cultivar The original tobacco cultivar PD7319 LC is a hybrid generated by pollinating plants of a male-sterile breeding line CMS TND950 with pollen produced by fertile breeding line Narrow Leaf Madole (phph). Hybrid cultivar PD7319 SRC is a hybrid generated by pollinating plants of a male-sterile breeding line CMS TND950 SRC with pollen produced by fertile breeding line Narrow Leaf Madole (phph) SRC (Table 1).

Each SRC line carries introduced deleterious mutations in three genes (CYP82E4 (SEQ ID NO: 5), CYP82E5 (SEQ ID NO: 8), and CYP82E10 (SEQ ID NO: 9)) previously documented to encode for nicotine demethylase enzymes (Lewis et al., *Phytochemistry*, 71 (2010), 1988-1998). The introduced mutations in CYP82E4 (cyp82e4 W329Stop (SEQ ID NO: 1)) and CYP82E5 (cyp82e5v2 W422Stop (SEQ ID NO: 2)) encode for premature stop codons which render the genes non-functional. The introduced mutation in CYP82E10 (cyp82e10 P381S (SEQ ID NO: 11)) does not encode for a premature stop codon, but does render the gene product non-functional for converting nicotine to nornicotine (Id.). When in homozygous condition, the three mutations result in tobacco plants with (1) reduced genetic capacity to demethylate nicotine to form nornicotine, and (2) a corresponding diminished potential to accumulate N-nitrosonornicotine (NNN). The mutation in CYP82E4 (cyp82e4 W329Stop (SEQ ID NO: 1)) also provides phenotypic stability for the "nicotine conversion" trait and eliminates the requirement to utilize the labor-intensive "LC" screening method for reducing levels of nornicotine in tobacco cultivars (see e.g., Jack et al. 2007. Implications of reducing nornicotine accumulation in burley tobacco: appendix A—the LC protocol. *Rec. Adv. Tob. Sci.* 33: 58-79).

$BC_1F_1$ progenies are screened using genotyping methodologies to identify individuals heterozygous for all three mutations. A single $BC_1F_1$ plant from each pedigree is backcrossed to the recurrent parent, to produce $BC_2F_1$ progenies. The process of backcrossing and identification of individuals heterozygous for all three mutations is repeated through the $BC_3F_1$, $BC_4F_1$, $BC_5F_1$, $BC_6F_1$, and $BC_7F_1$ stages. At the $BC_7F_1$ stage, individuals heterozygous for all three mutations from each pedigree are self-pollinated to produce $BC_7F_2$ seed. A large number of $BC_7F_2$ progeny from each pedigree are genotyped to identify individuals homozygous for all three mutations. $BC_7F_2$ plants homozygous for all three mutations are self-pollinated to produce $BC_7F_3$ families (SRC lines) in which the wild-type CYP82E4, CYP82E5v2, and CYP82E10 alleles are replaced by the mutant alleles (cyp82e4 W329Stop, cyp82e5v2 W422Stop, and cyp82e10 P381S).

The female parental line of PD7319 LC, CMS TND950, is cytoplasmic male sterile which causes pollen to not be produced. To develop CMS TND950 SRC dark tobacco, a plant of CMS TND950 was crossed with TND950 SRC dark tobacco to produce male-sterile plants heterozygous for all three mutations. A single male-sterile plant resulting from this cross was then subsequently backcrossed as a female to TND950 SRC dark tobacco to produce progeny that were segregating for individuals homozygous for all three mutations. Triple homozygous individuals were identified by DNA genotyping to produce the CMS TND950 SRC dark tobacco line. Because the line is male-sterile, it is maintained via pollination with TND950 SRC dark tobacco.

Example 12

Testing of Hybrid Cultivars PD7305 SRC, PD7309 SRC, PD7312 SRC, PD7318 SRC, and PD7319 SRC Hybrid cultivars PD7305 SRC, PD7309 SRC, PD7312 SRC, PD7318 SRC, and PD7319 SRC are evaluated for cured leaf chemistry, yield, and physical quality at three locations during 2015 (Blackstone (VA), Springfield (TN) and Princeton (KY)). Hybrid cultivars PD7305 LC, PD7309 LC, PD7312 LC, PD7318 LC, and PD7319 LC are included for comparison. The experimental design at each location is a randomized complete block design with three replications. Plots are harvested and cured. Plot weights are used to determine per acre yields. Cured leaf is evaluated by a former USDA tobacco grader. Composite leaf samples are collected from each plot and analyzed for percent nicotine, nornicotine, percent nicotine conversion, parts per million of total TSNAs, and parts per million of NNN using gas chromatography equipment and techniques described in Example 5 above (FIG. 4, 5, and Table 2).

Figure 4:
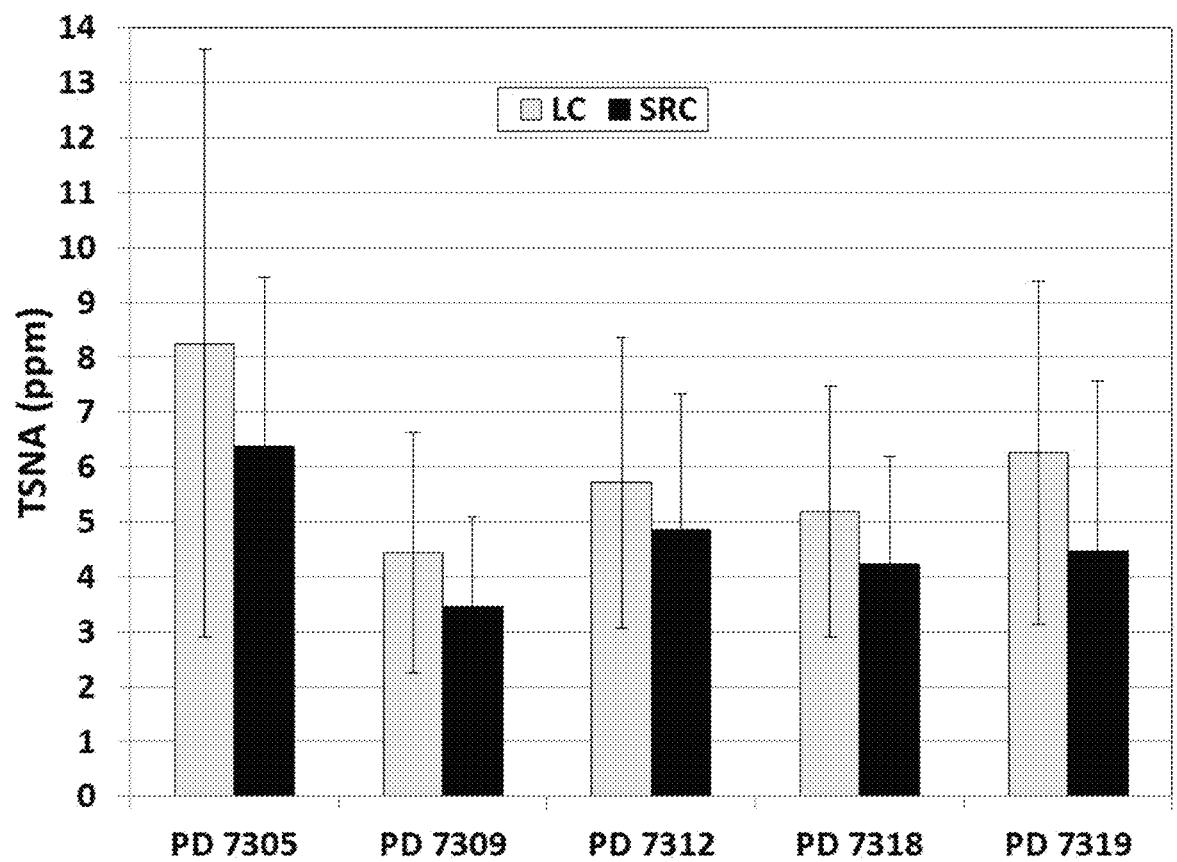
FIG. 4 depicts the total TSNA amounts, in parts per million, detected in dark tobacco hybrid cultivars PD7305 SRC, PD7309 SRC, PD7312 SRC, PD7318 SRC, and PD7319 SRC after curing.
Figure 5:
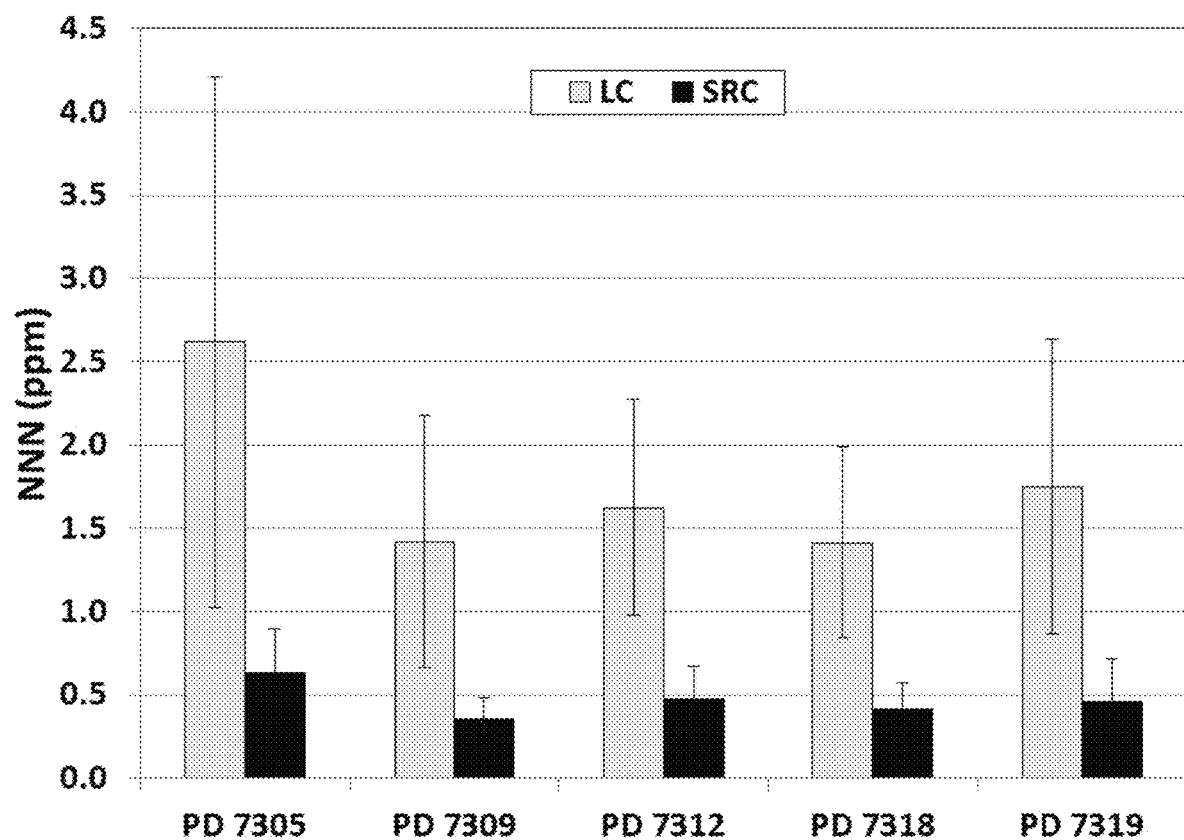
FIG. 5 depicts the NNN amounts, in parts per million, detected in dark tobacco hybrid cultivars PD7305 SRC, PD7309 SRC, PD7312 SRC, PD7318 SRC, and PD7319 SRC after curing.

SRC dark tobacco varieties exhibit a TSNA reduction of about 22% and an NNN reduction of about 74% compared to LC varieties grown in similar field plots (FIGS. 4 and 5). Comparisons using the Student's t test indicated that PD7309 SRC dark tobacco hybrid, PD7312 SRC dark tobacco hybrid PD7318 SRC dark tobacco hybrid, and PD7319 SRC dark tobacco hybrid had significantly (P<0.05) lower levels of nornicotine, percent nicotine conversion and NNN relative to PD7309 LC, PD7312 LC, PD7318 LC, and PD7319 LC, respectively (Table 2). Each SRC and LC comparison did not show significant differences from each other for percent nicotine, yield, or cured leaf quality indices. Although we did not see a statistical difference for levels of nornicotine and percent of nicotine conversion between PD7305 LC and PD7305 SRC dark tobacco hybrid, statistical differences in the NNN levels between these two hybrids indicates the efficacy of the SRC technology in PD7305 SRC dark tobacco hybrid.

Example 13

Smokeless Product Prototypes Comprising Dark Tobacco with SRC Technology

Smokeless tobacco product prototypes are developed from dark fire-cured tobacco, dark air-cured tobacco, and Burley stems comprising SRC technology and from dark fire-cured tobacco, dark air-cured tobacco, and Burley stems from LC varieties grown during the 2014 field season. SRC and LC tobacco is grown and cured using standard conditions and curing practices (See, e.g., 2017-2018 *Burley and Dark Tobacco Production Guide* (B. Pearce ed., (2017)). Tobacco included in smokeless product prototypes is aged for 2 years, processed, blended, fermented over three cures, and finished similar to the CRP2 standard moist snuff reference product.

Figure 6:
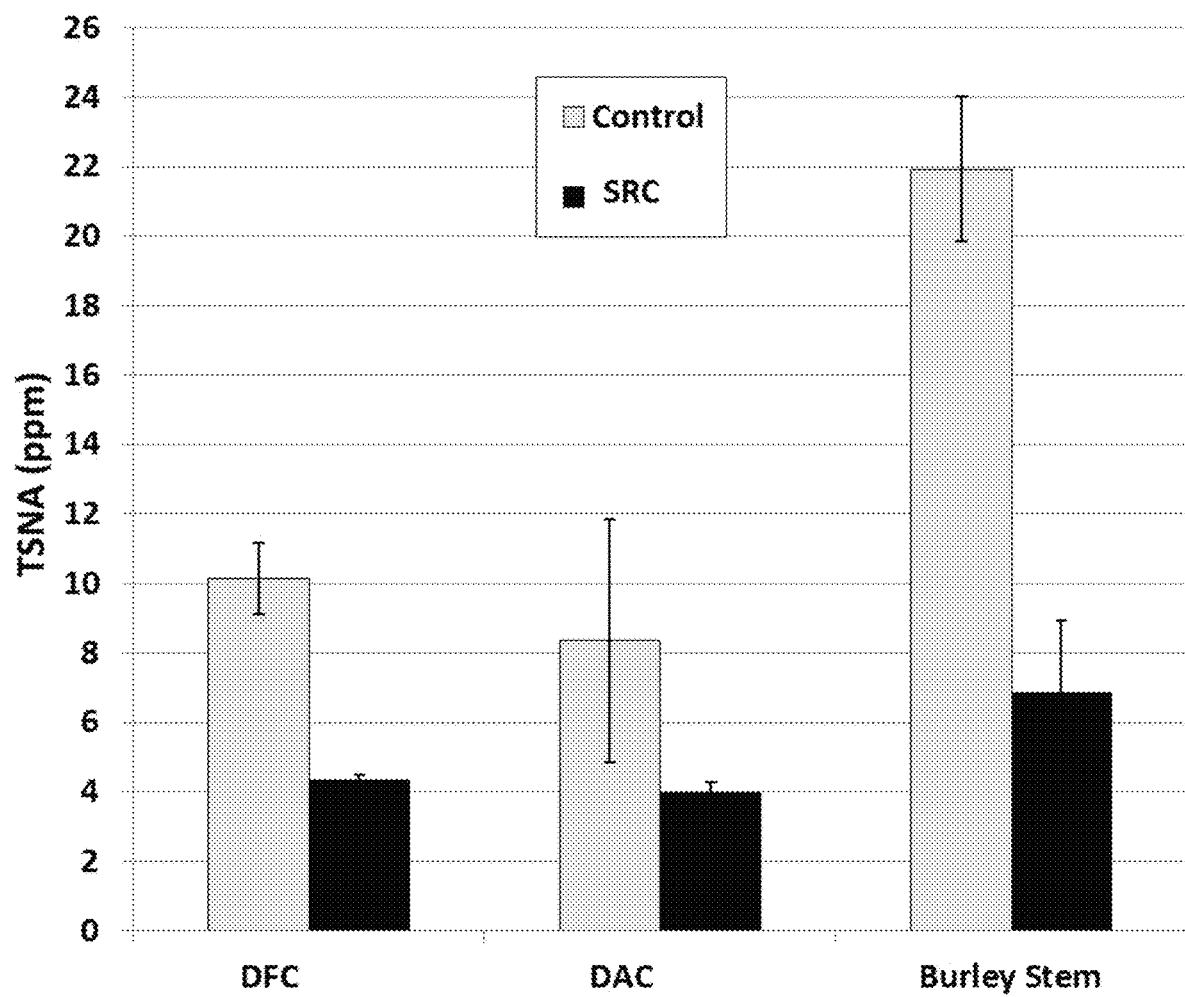
FIG. 6 depicts the total TSNA amounts, in parts per million, detected in the various component tobaccos used to create dark tobacco blends for smokeless products prototypes including both LC (control) and SRC varieties of dark-fired cured tobacco (DFC), dark air-cured tobacco (DAC), and Burley stems.
Figure 7:
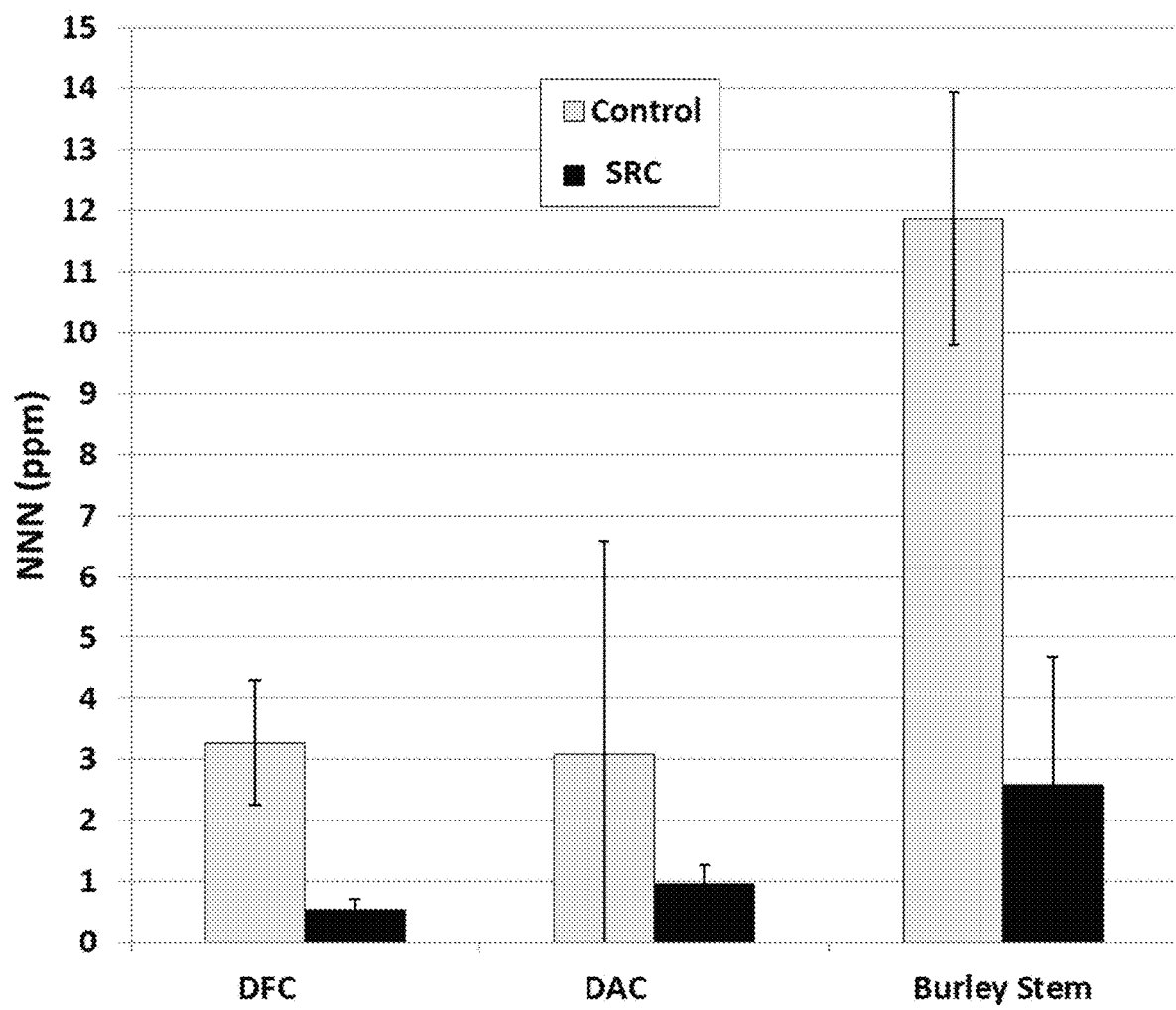
FIG. 7 depicts the NNN amounts, in parts per million, detected in the various component tobaccos used to create dark tobacco blends for smokeless products prototypes including both LC (control) and SRC varieties of dark-fired cured tobacco (DFC), dark air-cured tobacco (DAC), and Burley stems.

Total TSNA and NNN amounts are determined for each blend component (dark fire-cured tobacco, dark air-cured tobacco, and burley stems) using techniques described in Example 5. Both TSNA and NNN amounts are lower in each blend component comprising SRC technology as compared to the LC variety controls grown and cured using the same conditions (FIGS. 6 and 7). Total TSNA and NNN amounts are also determined at the blending stage, once out of cure, and as finished products (FIGS. 8 and 9). Both TSNA and NNN amounts are lower at each step of the production process in tobacco comprising SRC technology as compared to the LC variety control undergoing the same processing steps. The reduction in total TSNA and NNN amounts in the finished smokeless product prototypes created using tobacco comprising SRC technology is consistent with the reductions seen in the raw materials.

TABLE 2

Means for field test of SRC dark tobacco hybrids in three locations in 2015.

| Genotype | Yield (lbs/A) | Grade Index | Nicotine (%) | Nornicotine (%) | % Nicotine Conversion | NNN |
|---|---|---|---|---|---|---|
| PD7305 LC | 2974 | 58 | 5.74 | 0.124 | 2.21 | 3.29* |
| PD7305 SRC | 2900 | 55 | 5.78 | 0.019 | 0.33 | 0.52* |
| PD7309 LC | 3030 | 63 | 6.66 | 0.087* | 1.31* | 2.07* |
| PD7309 SRC | 2948 | 69 | 6.69 | 0.023* | 0.33* | 0.47* |
| PD7312 LC | 3069 | 63 | 7.06 | 0.104* | 1.38* | 2.13* |
| PD7312 SRC | 3069 | 63 | 7.55 | 0.024* | 0.30* | 0.60* |
| PD7318 LC | 3001 | 67 | 6.49 | 0.075* | 1.14* | 1.87* |
| PD7318 SRC | 2971 | 67 | 6.94 | 0.022* | 0.30* | 0.54* |
| PD7319 LC | 3077 | 63 | 6.44 | 0.065* | 0.97* | 1.65* |
| PD7319 SRC | 3034 | 68 | 6.89 | 0.021* | 0.30* | 0.58* |

*Statistical difference between LC and SRC dark tobacco hybrids based on Student's t test with alpha = 0.05

PD7305 LC is a hybrid variety generated by pollinating plants of a male-sterile breeding line CMS TND950 with pollen produced by fertile breeding line TND950 (phph).

PD7305 SRC tobacco hybrid is a backcross-derived version of dark tobacco hybrid PD7305 LC carrying introduced deleterious mutations in three genes (cyp82e4 W329Stop, cyp82e5v2 W422 Stop, and cyp82e10 P381S).

PD7309 LC is a hybrid variety generated by pollinating plants of a male-sterile breeding line CMS Narrow Leaf Madole with pollen produced by fertile breeding line Narrow Leaf Madole (phph).

PD7309 SRC tobacco hybrid is a backcross-derived version of dark tobacco hybrid PD7309 LC carrying introduced deleterious mutations in three genes (cyp82e4 W329Stop, cyp82e5v2 W422Stop, and cyp82e10 P381S).

PD7312 LC is a hybrid variety generated by pollinating plants of a male-sterile breeding line CMS KY171 with pollen produced by fertile breeding line Narrow Leaf Madole.

PD7312 SRC tobacco hybrid is a backcross-derived version of dark tobacco hybrid PD7312 LC carrying introduced deleterious mutations in three genes (cyp82e4 W329Stop, cyp82e5v2 W422Stop, and cyp82e10 P381S).

PD7318 LC is a hybrid variety generated by pollinating plants of a male-sterile breeding line CMS KY171 with pollen produced by fertile breeding line Narrow Leaf Madole (phph).

PD7318 SRC tobacco hybrid is a backcross-derived version of dark tobacco hybrid PD7318 LC carrying introduced deleterious mutations in three genes (cyp82e4 W329Stop, cyp82e5v2 W422 Stop, and cyp82e10 P381S).

PD7319 LC is a hybrid variety generated by pollinating plants of a male-sterile breeding line CMS TND950 with pollen produced by fertile breeding line Narrow Leaf Madole (phph).

PD7319 SRC tobacco hybrid is a backcross-derived version of dark tobacco hybrid PD7319 LC carrying introduced deleterious mutations in three genes (cyp82e4 W329Stop, cyp82e5v2 W422 Stop, and cyp82e10 P381S).

Deposit Information

A deposit of the proprietary inbred plant lines disclosed above and recited in the appended claims have been made with American Type Culture Collection (ATCC), 10801 University Boulevard, Manassas, Va. 20110. The date of deposit for TND950 (phph) SRC, Narrow Leaf Madole (phph) SRC, Narrow Leaf Madole SRC, CMS TND950 SRC, CMS Narrow Leaf Madole SRC, CMS KY171 SRC was Nov. 22, 2016. The deposits of 2500 seeds for each variety was taken from the same deposits maintained since prior to the filing date of this application. Upon issuance of a patent, all restrictions upon the deposits will be irrevocably removed, and the deposits are intended by Applicant to meet all of the requirements of 37 C.F.R. § 1.801-1.809. The ATCC has issued the following accession numbers: ATCC Accession No. PTA-123665 for TND950 (phph) SRC; ATCC Accession No. PTA-123664 for Narrow Leaf Madole (phph) SRC; ATCC Accession No. PTA-123663 for Narrow Leaf Madole SRC, ATCC Accession No. PTA-123662 for CMS TND950 SRC, ATCC Accession No. PTA-123661 for CMS Narrow Leaf Madole SRC, and ATCC Accession No. PTA-123660 for CMS KY171 SRC. These deposits will be maintained in the depository for a period of 30 years, or 5 years after the last request, or for the effective life of the patent, whichever is longer, and will be replaced as necessary during that period. Applicants do not waive any infringement of their rights granted under this patent or under the Plant Variety Protection Act (7 U.S.C. 2321 et seq.).

What is claimed is:

1. Cured tobacco material or a tobacco product prepared therefrom, wherein said cured tobacco material is from a tobacco plant, or part thereof, of a cultivar, or a progeny hybrid having a first parent cultivar, wherein said cultivar and said first parent cultivar, but not a second parent cultivar, are selected from the group consisting of TND950 (phph) SRC, Narrow Leaf Madole (phph) SRC, Narrow Leaf Madole SRC, CMS TND950 SRC, CMS Narrow Leaf Madole SRC, and CMS KY171 SRC; a representative sample seed of said TND950 (phph) SRC, Narrow Leaf Madole (phph) SRC, Narrow Leaf Madole SRC, CMS TND950 SRC, CMS Narrow Leaf Madole SRC, CMS KY171 SRC having been deposited with the ATCC under ATCC Accession Nos. PTA-123665, PTA-123664, PTA-123663, PTA-123662, PTA-123661, and PTA-123660, respectively.

2. The tobacco product of claim 1, wherein said tobacco product is selected from the group consisting of a pipe tobacco, cigar tobacco, cigarette tobacco, cigarette, chewing tobacco, leaf tobacco, shredded tobacco, hookah tobacco, cut tobacco, cigarillo, non-ventilated recess filter cigarette, vented recess filter cigarette, cigar, moist snuff, nasal snuff, snuff, loose leaf chewing tobacco, plug chewing tobacco, and chewing tobacco.

3. The tobacco product of claim 1, wherein said tobacco product has an amount of nornicotine between about 3 mg/g and 0.01 pg/g.

4. The tobacco product of claim 1, wherein said tobacco product has an amount of N'-nitrosonornicotine (NNN) of between about 10 pg/g and 0.01 pg/g.

5. The tobacco product of claim 1, wherein said cured tobacco material is at least about 5% by dry weight of the total tobacco material in said tobacco product.

6. The tobacco product of claim 5, wherein said cured tobacco material has a dry weight percentage of said total tobacco material of at least about 10%.

7. The tobacco product of claim 1, wherein said tobacco plant has a percent conversion to nornicotine of less than 2.0%.

8. A method of producing a tobacco product, comprising:
a. providing cured tobacco material from a tobacco plant, or part thereof, wherein said tobacco plant is a progeny hybrid having a first parent cultivar selected from the group consisting of TND950 (phph) SRC, Narrow Leaf Madole (phph) SRC, Narrow Leaf Madole SRC, CMS TND950 SRC, CMS Narrow Leaf Madole SRC, and CMS KY171 SRC; a representative sample seed of said TND950 (phph) SRC, Narrow Leaf Madole (phph) SRC, Narrow Leaf Madole SRC, CMS TND950 SRC, CMS Narrow Leaf Madole SRC, and CMS KY171 SRC tobacco cultivars having been deposited with the ATCC under ATCC Accession Nos. PTA-123665, PTA-123664, PTA-123663, PTA-123662, PTA-123661, and PTA-123660, respectively; wherein a second parent cultivar is not selected from the group consisting of TND950 (phph) SRC, Narrow Leaf Madole (phph) SRC, Narrow Leaf Madole SRC, CMS TND950 SRC, CMS Narrow Leaf Madole SRC, and CMS KY171 SRC; a representative sample seed of said TND950 (phph) SRC, Narrow Leaf Madole (phph) SRC, Narrow Leaf Madole SRC, CMS TND950 SRC, CMS Narrow Leaf Madole SRC, and CMS KY171 SRC tobacco cultivars having been deposited with the ATCC under ATCC Accession Nos. PTA-123665, PTA-123664, PTA-123663, PTA-123662, PTA-123661, and PTA-123660, respectively; and
b. preparing a tobacco product from said cured tobacco material.

9. The tobacco product of claim 8, wherein said tobacco product is selected from the group consisting of a pipe tobacco, cigar tobacco, cigarette tobacco, cigarette, chewing tobacco, leaf tobacco, shredded tobacco, hookah tobacco, cut tobacco, cigarillo, non-ventilated recess filter cigarette, vented recess filter cigarette, cigar, moist snuff, nasal snuff, snuff, loose leaf chewing tobacco, plug chewing tobacco, and chewing tobacco.

10. The tobacco product of claim 8, wherein said tobacco product has an amount of nornicotine between about 3 mg/g and 0.01 pg/g.

11. The tobacco product of claim 8, wherein said tobacco product has an amount of N'-nitrosonornicotine (NNN) of between about 10 pg/g and 0.01 pg/g.

12. The tobacco product of claim 8, wherein said cured tobacco material is at least about 5% by dry weight of the total tobacco material in said tobacco product.

13. The tobacco product of claim 12, wherein said cured tobacco material has a dry weight percentage of said total tobacco material of at least about 10%.

14. The method of claim 8, wherein said tobacco plant has a percent conversion to nornicotine of less than 2.0%.

15. The method of claim 8; wherein said tobacco product comprises cured tobacco material from a progeny hybrid selected from the group consisting of PD7305 SRC, PD7309 SRC, PD7312 SRC, PD7318 SRC, and PD7319 SRC; wherein:
PD7305 SRC has two parent cultivars CMS TND950 SRC and TND950 (phph) SRC;
PD7309 SRC has two parent cultivars CMS Narrow Leaf Madole SRC and Narrow Leaf Madole (phph) SRC;
PD7312 SRC has two parent cultivars CMS KY171 SRC and Narrow Leaf Madole SRC;
PD7318 SRC has two parent cultivars CMS KY171 SRC and Narrow Leaf Madole (phph) SRC; and
PD7319 SRC has two parent cultivars CMS TND950 SRC and Narrow Leaf Madole (phph) SRC.

16. An $F_1$ progeny plant having one parent tobacco cultivar selected from the group consisting of TND950 (phph) SRC, Narrow Leaf Madole (phph) SRC, Narrow Leaf Madole SRC, CMS TND950 SRC, CMS Narrow Leaf Madole SRC, and CMS KY171 SRC; a representative sample seed of said TND950 (phph) SRC, Narrow Leaf Madole (phph) SRC, Narrow Leaf Madole SRC, CMS TND950 SRC, CMS Narrow Leaf Madole SRC, and CMS KY171 SRC tobacco cultivars having been deposited with the ATCC under ATCC Accession Nos. PTA-123665, PTA-123664, PTA-123663, PTA-123662, PTA-123661, and PTA-123660, respectively.

17. The $F_1$ progeny plant of claim 16, wherein said $F_1$ plant is male sterile.

18. The $F_1$ progeny plant of claim 16, wherein said $F_1$ plant has a percent conversion to nornicotine of less than 2.0%.

* * * * *